US012392784B2

(12) United States Patent
Bloomgren et al.

(10) Patent No.: US 12,392,784 B2
(45) Date of Patent: *Aug. 19, 2025

(54) METHOD OF ASSESSING RISK OF PML

(71) Applicant: BIOGEN MA INC., Cambridge, MA (US)

(72) Inventors: Gary Lewis Bloomgren, Concord, MA (US); Carmen Bozic, Newton, MA (US); Sophia Lee, Waltham, MA (US); Amy Pace, Brookline, MA (US); Tatiana Plavina, North Reading, MA (US); Meena Subramanyam, Stoneham, MA (US)

(73) Assignee: Biogen MA Inc., Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 18/731,059

(22) Filed: May 31, 2024

(65) Prior Publication Data
US 2025/0003983 A1 Jan. 2, 2025

Related U.S. Application Data

(63) Continuation of application No. 17/700,250, filed on Mar. 21, 2022, now Pat. No. 12,031,990, which is a continuation of application No. 16/896,074, filed on Jun. 8, 2020, now Pat. No. 11,280,794, which is a continuation of application No. 16/115,350, filed on Aug. 28, 2018, now Pat. No. 10,677,803, which is a continuation of application No. 14/893,989, filed as application No. PCT/US2014/039525 on May 27, 2014, now Pat. No. 10,119,976.

(60) Provisional application No. 61/828,021, filed on May 28, 2013.

(51) Int. Cl.
G01N 33/569 (2006.01)
C07K 16/08 (2006.01)
C07K 16/28 (2006.01)
C12N 7/00 (2006.01)
G01N 33/53 (2006.01)
G01N 33/68 (2006.01)
C12Q 1/70 (2006.01)

(52) U.S. Cl.
CPC ..... G01N 33/6854 (2013.01); C07K 16/2842 (2013.01); C12N 7/00 (2013.01); G01N 33/56983 (2013.01); C07K 2317/24 (2013.01); C12N 2710/22011 (2013.01); C12Q 1/70 (2013.01); G01N 2333/025 (2013.01); G01N 2469/20 (2013.01); G01N 2800/24 (2013.01); G01N 2800/28 (2013.01); G01N 2800/50 (2013.01)

(58) Field of Classification Search
CPC ............ C12N 2710/22011; C12N 7/00; C12N 2710/22033; G01N 2333/025; G01N 2469/20
See application file for complete search history.

(56) References Cited

U.S. PATENT DOCUMENTS

| | | |
|---|---|---|
| 3,817,837 A | 6/1974 | Rubenstein et al. |
| 3,850,752 A | 11/1974 | Schuurs et al. |
| 3,939,350 A | 2/1976 | Kronick et al. |
| 3,996,345 A | 12/1976 | Ullman et al. |
| 4,235,601 A | 11/1980 | Deutsch et al. |
| 4,275,149 A | 6/1981 | Deutsch et al. |
| 4,277,437 A | 7/1981 | Maggio |
| 4,366,241 A | 12/1982 | Tom et al. |
| 4,376,110 A | 3/1983 | David et al. |
| 4,391,904 A | 7/1983 | Litman et al. |
| 4,517,288 A | 5/1985 | Giegel et al. |
| 4,703,017 A | 10/1987 | Campbell et al. |
| 4,818,677 A | 4/1989 | Hay-Kaufman et al. |
| 4,837,168 A | 6/1989 | de Jaeger et al. |
| 4,943,522 A | 7/1990 | Eisinger et al. |
| 5,096,837 A | 3/1992 | Fan et al. |
| 5,118,428 A | 6/1992 | Sand et al. |
| 5,118,630 A | 6/1992 | Glaze |
| 5,221,616 A | 6/1993 | Kolb et al. |
| 5,223,220 A | 6/1993 | Fan et al. |
| 5,225,328 A | 7/1993 | Chang |
| 5,329,459 A | 7/1994 | Kaufman et al. |
| 5,415,994 A | 5/1995 | Imrich et al. |
| 5,434,057 A | 7/1995 | Dorian |
| 5,521,102 A | 5/1996 | Boehringer et al. |
| 5,536,646 A | 7/1996 | Sand et al. |
| 5,541,069 A | 7/1996 | Mortensen et al. |
| 5,559,041 A | 9/1996 | Kang et al. |
| 5,686,315 A | 11/1997 | Pronovost et al. |
| 5,712,172 A | 1/1998 | Huang et al. |
| 5,763,262 A | 6/1998 | Wong et al. |
| 5,766,961 A | 6/1998 | Pawlak et al. |
| 5,770,460 A | 6/1998 | Pawlak et al. |
| 5,773,234 A | 6/1998 | Pronovost et al. |

(Continued)

FOREIGN PATENT DOCUMENTS

| | | |
|---|---|---|
| EP | 1712913 A1 | 10/2006 |
| EP | 1933140 A1 | 6/2008 |

(Continued)

OTHER PUBLICATIONS

Aalberse et al., "IgG4 breaking the rules", Immunology, vol. 105, No. 1, pp. 9-19 (2002).
Abbing et al., "Efficient Intracellular Delivery of a Protein and a Low Molecular Weight Substance via Recombinant Particles", The Journal of Biological Chemistry, vol. 279, No. 25, pp. 27410-27421, (2004).

(Continued)

Primary Examiner — Barry A Chestnut
(74) Attorney, Agent, or Firm — Todd Lorenz

(57) ABSTRACT

The invention relates to methods of assessing a patient's risk of developing Progressive multifocal leukoencephalopathy (PML).

26 Claims, 3 Drawing Sheets

(56) References Cited

U.S. PATENT DOCUMENTS

| | | |
|---|---|---|
| 5,786,220 A | 7/1998 | Pronovost et al. |
| 5,804,452 A | 9/1998 | Pronovost et al. |
| 5,814,455 A | 9/1998 | Pronovost et al. |
| 5,840,299 A | 11/1998 | Bendig et al. |
| 5,845,255 A | 12/1998 | Mayaud |
| 5,939,331 A | 8/1999 | Burd et al. |
| 6,014,631 A | 1/2000 | Teagarden et al. |
| 6,033,665 A | 3/2000 | Yednock |
| 6,187,598 B1 | 2/2001 | May et al. |
| 6,229,011 B1 | 5/2001 | Chen et al. |
| 6,238,859 B1 | 5/2001 | Luke et al. |
| 6,305,377 B1 | 10/2001 | Portwood et al. |
| 6,306,642 B1 | 10/2001 | Nelson et al. |
| 6,352,862 B1 | 3/2002 | Davis et al. |
| 6,388,084 B1 | 5/2002 | Kaplan et al. |
| 6,485,982 B1 | 11/2002 | Charlton |
| 6,534,320 B2 | 3/2003 | Ching et al. |
| 6,551,593 B1 | 4/2003 | Ringler et al. |
| 6,602,503 B1 | 8/2003 | Lobb et al. |
| 6,605,602 B1 | 8/2003 | Vats |
| 6,620,626 B1 | 9/2003 | Bodily |
| 6,623,981 B2 | 9/2003 | Billheimer et al. |
| 6,767,714 B2 | 7/2004 | Nazareth et al. |
| 6,790,611 B2 | 9/2004 | Lassen et al. |
| 7,008,949 B2 | 3/2006 | Konradi et al. |
| 7,026,328 B2 | 4/2006 | Konradi et al. |
| 7,026,501 B2 | 4/2006 | Kawaguchi et al. |
| 7,101,855 B2 | 9/2006 | Dressen et al. |
| 7,129,053 B1 | 10/2006 | Reiter et al. |
| 7,419,666 B1 | 9/2008 | Iliaki et al. |
| 7,718,444 B2 | 5/2010 | Takizawa et al. |
| 7,807,167 B2 | 10/2010 | Taylor et al. |
| 8,410,115 B2 | 4/2013 | Lieberburg |
| 9,316,641 B2 | 4/2016 | Gorelik |
| 9,493,567 B2 | 11/2016 | Lieburgurg |
| 10,119,976 B2 | 11/2018 | Bloomgren et al. |
| 10,233,245 B2 | 3/2019 | Lieberburg |
| 10,444,234 B2 | 10/2019 | Gorelik |
| 10,677,803 B2 | 6/2020 | Bloomgren et al. |
| 2001/0021910 A1 | 9/2001 | Goldstein |
| 2002/0052543 A1 | 5/2002 | Williams et al. |
| 2002/0197233 A1 | 12/2002 | Relton et al. |
| 2003/0032923 A1 | 2/2003 | Eakins et al. |
| 2003/0176498 A1 | 9/2003 | Kawaguchi et al. |
| 2003/0186327 A1 | 10/2003 | Babcook |
| 2004/0009169 A1 | 1/2004 | Taylor et al. |
| 2004/0138243 A1 | 7/2004 | Konradi et al. |
| 2004/0142954 A1 | 7/2004 | Konradi et al. |
| 2004/0248216 A1 | 12/2004 | Seino |
| 2005/0215869 A1 | 9/2005 | Elsayed et al. |
| 2005/0283385 A1 | 12/2005 | Hunkeler et al. |
| 2006/0009385 A1 | 1/2006 | Hoffman et al. |
| 2006/0013799 A1 | 1/2006 | Konradi et al. |
| 2007/0142416 A1 | 6/2007 | Semko et al. |
| 2007/0190667 A1 | 8/2007 | Cole et al. |
| 2007/0207141 A1 | 9/2007 | Lieburgurg |
| 2007/0231319 A1 | 10/2007 | Yednock |
| 2007/0275481 A1 | 11/2007 | Vasilyeva et al. |
| 2008/0044382 A1 | 2/2008 | Lieberburg |
| 2008/0058357 A1 | 3/2008 | Smith et al. |
| 2008/0233150 A1 | 9/2008 | Smith et al. |
| 2009/0010926 A1 | 1/2009 | Panzara et al. |
| 2009/0169477 A1 | 7/2009 | Panzara et al. |
| 2009/0176256 A1 | 7/2009 | Subramanyam et al. |
| 2009/0216107 A1 | 8/2009 | Rubin et al. |
| 2011/0123536 A1 | 5/2011 | Chermann |
| 2012/0177642 A1 | 7/2012 | Yednock |

FOREIGN PATENT DOCUMENTS

| | | |
|---|---|---|
| EP | 1485127 B1 | 6/2011 |
| EP | 2575792 A1 | 4/2013 |
| EP | 2645106 A2 | 10/2013 |
| EP | 2676967 B1 | 8/2019 |
| WO | WO 1992/19774 A1 | 11/1992 |
| WO | WO 1994/16094 A2 | 7/1994 |
| WO | WO 1997/19174 A1 | 5/1997 |
| WO | WO 2003/016902 A1 | 2/2003 |
| WO | WO 2003/072040 A2 | 9/2003 |
| WO | WO 2004/001539 A2 | 12/2003 |
| WO | WO 2006/107962 A2 | 10/2006 |
| WO | WO 2006/112951 A2 | 10/2006 |
| WO | WO 2007/041270 A1 | 4/2007 |
| WO | WO 2007/100763 A2 | 9/2007 |
| WO | WO 2007/100770 A2 | 9/2007 |
| WO | WO 2007/101165 A1 | 9/2007 |
| WO | WO 2007/103112 A2 | 9/2007 |
| WO | WO 2010/090757 A1 | 8/2010 |
| WO | WO 2010/096674 A2 | 8/2010 |
| WO | WO 2011/085369 A1 | 7/2011 |
| WO | WO 2012/166971 A2 | 12/2012 |

OTHER PUBLICATIONS

Abraham et al., "A Small-Molecule, Tight-binding Inhibitor of the Integrin a4131 Blocks Antigen-induced Airway Responses and Inflammation in Experimental Asthma in Sheep," Am. J. Respir. Crit. Care Med., 162:603-611 (2000).

Achiron, et al., "Does the Flap of a Butterfly's Wings in Brazil set off a Tornado in Texas? The JC Virus Story in Multiple Sclerosis", IMAJ, pp. 283-285 (2005).

Agostini et al., "JC Virus (JCV) Genotypes in Brain Tissue from Patients with Progressive Multifocal Leukoencephalopathy (PML) and in Urine from Controls without PML: Increased Frequency of JCV Type 2 in PML", Journal of Infectious Diseases, vol. 176, No. 1, p. 6, (1997).

Agostini et al., "Genotype Profile of Human Polyomavirus JC Excreted in Urine of Immunocompetent Individuals," J. Clin. Microbiol., 34:159-164 (1996).

Ahsan, N, and Shah, KV, "Polyomaviruses and human diseases.—chapter 1", Retinal Degenerative Diseases: Advances in Experimental Medicine and Biology, Springer, US, vol. 577, pp. 1-18, (2006).

Albrecht et al., "Highly active antiretroviral therapy significantly improves the prognosis of patients with HIV-associated progressive multifocal leukoencephalopathy," AIDS, 12:11491154 (1998).

Aly, Lilian, et al. "Central role of JC virus-specific CD4+ lymphocytes in progressive multi-focal leucoencephalopathy-immune reconstitution inflammatory syndrome." Brain 134.9 (2011): 2687-2702.

Anonymous, "Natalizumab in the Treatment of Rheumatoid Arthritis in Subjects Receiving Methotrexate", US National Library of Medicine ClinicalTrials.gov, (2009), pp. 1-10, downloaded from https://clinicaltrials.gov/ct2/show/results/NCT00083759?view=results.

Astrom, K.E., et al. "Progressive multifocal leuko-encephalopathy; a hitherto unrecognized complication of chronic lymphatic leukaemia and Hodgkin's disease." Brain 81 (1958): 93-111.

Attwood, et al. , "The Babel of Bioinformatics," Science, vol. 290, No. 5491, pp. 471-473 (2000).

Baker et al., "Protein Structure Predication and Structural Genomics," Science, vol. 294, No. 5540, pp. 93-96 (2001).

Baron et al., "Surface Expression of a4 Integrin by CD4 T Cells Is Required for Their Entry Into Brain Parenchyma," J. Exp. Med., 177:57-68 (1993).

Behzhad-Behbahani et al., Detection of BK virus and JC virus DNA in urine samples from immunocompromised (HIV-infected) and Immunocometent (HIV-non-Infected) patients using polymerase chain reaction and microplate hybridisation J Clin Virol. Apr. 29, 2004(4), pp. 224-229.

Benedict et al., "Personality Disorder in Myltiple Sclerosis Correlates With Cognitive Impairment", J Neuropsychiatry Clin Neurosci, vol. 13, pp. 70-76 (2001).

Berger et al., "Predictive Factors for Prolonged Survival in Acquired Immunodeficiency Syndrome-Associated Progressive Multifocal Leukoencephalopathy," Ann. Neurol., 44:341349 (1998).

Berger, J.R. and Major, E.O., "Progressive Multifocal Leukoencephalopathy", Seminars in Neurology, vol. 19, No. 2, pp. 193-200 (1999).

(56) References Cited

OTHER PUBLICATIONS

Berger, Jr, Nath, A, Progressive multifocal leukoencephalopathy, Cecil's Textbook of Internal Medicine, 21st Ed., W.B. Saunders, Philadephia, PA, Chapeter 479.4, pp. 2137-2138 (2000).
Berger, Jr. et al.: "Progressive multifocal leukoencephalopathy and natalizumab—Unforseen consequences"; New Egland Journal of Medicine, vol. 353, No. 4, pp. 414-416 (2005).
Berger, Jr. et al.: "Progressive multifocal leukoencephalopathy: lessons from AIDS and natalizumab", Neurological Research, vol. 28, pp. 299-305 (2006).
Berger et al., "Monoclonal antibodies and progressive multifocal leukoencephalopathy", mAbs, vol. 1(6), pp. 583-589 (2009).
Berger, Joseph R. "Too much of a good thing?: IRIS with natalizumab-associated PML." Neurology 77.11 (2011): 1033-1034.
Berger et al., "JC virus antibody status underestimates infection rates : JCV Antibody Status", Annals of Neurology, vol. 74, No. 1, , pp. 84-90 (2013).
Berger, Joseph R., et al. "PML diagnostic criteria: consensus statement from the AAN Neuroinfectious Disease Section." Neurology 80.15 (2013): 1430-1438.
Berger, Joseph R. "The clinical features of PML." Cleveland Clinic Journal of Medicine 78.2 (2011): S8-S12.
Biogen Press Release, Nov. 23, 2004, FDA grants accelerated approval of YSABRI, formerly antegren for the treatment of MS. "Biogen IDEC and ELAN Announce Voluntary Suspension of Tysabri®", Feb. 28, 2005 (Feb. 28, 2005), (//www.biogenidec.com/press_archive.aspx?ID=6015).
Bitsch et al., "Acute axonal injury in multiple sclerosis Correlation with Demyelination and inflammation," Brain, vol. 123, pp. 1174-1183 (2000).
Bjartmar et al., "Axonal pathology in myelin disorders," J. Neurocytol., vol. 28, pp. 383-395 (1999).
Bjartmar, C. and Trapp, B.D., "Axonal and neuronal degeneration in multiple sclerosis: mechanisms and functional consequences," Curr. Opin. Neurol., vol. 14, pp. 171-278 (2001).
Blake, Kim, et al, "JC virus associated meningoencephalitis in an immunocompetent girl." Arch Dis Child. (Jul. 1992) 67(7):956-957.
Bloomgren, G. et al. "Risk of Natalizumab-Associated Progressive Multifocal Leukoencephalopathy", N Engl J Med., vol. 366, pp. 1870-1880 (2012).
Bozic et al., "Anti-John Cunningham virus antibody prevalence in multiple sclerosis patients: baseline results of Stratify-1." Ann Neurol., 70(5):742-50 (2011).
Bozic et al., "JCV Epidemiology in MS (JEMS): prevalence of anti-JC virus antibodies in multiple sclerosis patients", 22nd Annual Meeting of European Neurological Society, Jun. 9-12, 2012.
Braun et al., Oligonucleotide and plasmid DNA packaging into polyoma VP1 virus-like particles expressed in coli Biotechnol. Appl. Biochem. vol. 29, pp. 31-43 (1999).
Brennan, D.C., et al.; "Incidence of BK with tracrolimus versus cyclosporine and impact of preemptive immunosuppression reduction"; American Journal of Transplantation Mar. 2005 DK, vol. 5, No. 3, pp. 582-594 (2005).
Brocke et al., "Antibodies to CD44 and Integrin a4, but not L-selection, Prevent Central Nervous System Inflammation and Experimental Encephalomyelitis by Blocking Secondary Leukocyte Recruitment," Proc. Natl. Acad. Sci., 96:6896-6901 (1999).
Brown, "Natalizumab in the treatment of multiple sclerosis," Therapeutics and clinical Risk Management, vol. 6, pp. 585-594 (2009).
Brück et al., "Inflammatory Central Nervous System Demyelination: Correlation of Magnetic Resonance Imaging Findings with Lesion Pathology," Ann. Neurol., 42:783-793 (1997).
Calabresi et al., The incidence and significance of anti-natalizumab antibodies: results from AFFIRM and Neurology, vol. 69(14), pp. 1391-1403 (2007).
Cannella, B. and Raine, D.S., "The Adhesion Molecule and Cytokine Profile of Multiple Sclerosis Lesions," Ann. Neurol., vol. 37, pp. 424-435 (1995).
Carson et al. "Monoclonal antibody-associate progressive multifocal leucoencephalopathy in patients treated with rituximab, natalizumab, and efalizumab: a Review from the Reasearch on Adverse Drug Events and Reports (RADAR) Project", Lancet Oncol. vol. 10(8), pp. 816-824 (2009).
Carter et al., "Lack of Serologic Evidence for Prevalent Simian Virus 40 Infection in Humans," Journal of the National Cancer Institute, vol. 95(2), pp. 1522-1530 (2003).
Casal J I: "Use of the baculovirus expression system for the generation of virus-like particles.", Biotechnology & Engineering Reviews 2001, vol. 18, pp. 73-87 (2001).
Chabas et al., "The Influence of the Proinflammatry Cytokine, Osteopontin, on Augtoimmune Demyelinating Disease," Science, vol. 294, pp. 1731-1735 (2001).
Chang et al., "Self-assembly of the JC virus major capsid protein, VP1, expressed in insect cells", Journal of Virology, vol. 78, pp. 1435-1439 (1997).
Chang et al., "High incidence of JC viruria in JC-seropositive older individuals," J. Neurovirol., vol. 8, pp. 447-451 (2002).
Chaudhuri, A. "Lessons for clinical trials from natalizumab in multiple sclerosis", BMJ, 332:416419 (2006).
Christensen et al., "α4 Integrin Directs Virus-Activated CD8+ T Cells to Sites of Infection$_1$," J. Immunol., vol. 154, pp. 5293-5301 (1995).
Ciccarelli, O. and Miller, D. H., "Magnetic resonance imaging in multiple sclerosis", Practical Neurology, vol. 2, pp. 103-112 (2002).
Cinque et al., "Progressive Multifocal Leukoencephalopathy Complicating HIV-1 Infection", Lancet Infect. Dis, vol. 9(10), pp. 625-636 (2009).
Clifford et al., "HAART Improves Prognosis in HIV-associated Progressive Multifocal Leukoencephalopathy," Neurology, 52:623-625 (1999).
Clifford, David B., et al. "Rituximab-associated progressive multifocal leukoencephalopathy in rheumatoid arthritis." Archives of neurology 68.9 (2011): 1156-1164.
Cohen et al., "A ohase 2 study of natalizymab in subjects with moderate to severe rheumatoid arthritis." ACR Annual Meetings; 10.-15 Washington. Poster 497 Nov. 2006.
Collazos, "Opportunistic Infections of the CNS in Patients with AIDS," CNS Drugs, 17:869887 (2003).
Crowder et al., "Successful Outcome of Progressive Multifocal Leukoencephalopathy in a Renal Transplant Patient," American Journal of Transplantation, 5:1151-1158 (2005).
Delos et al., "Expression of Polyomavirus Minor Capsid Proteins VP2 and VP3 in Escherichia coli: In Vitro Interactions with Recombinant VP1 Capsomeres," J. of Virology, vol. 69, No. 12, pp. 7734-7742 (1995).
Demeter, "JC, BK, and Other Polyomaviruses; Progressive Multifocal Leukoencephalopathy," Mandell, Douglas and Bennett's Principles and Practice of Infectious Diseases, Mandell et al. Eds., 4th Ed., New York, NY: Churchill Livingstone; 1995:1400-1406.
Dobbs et al., "Performance characteristics of the immunoglobulin G-capture BED-enzyme immunoassay, an assay to detect recent human immunodeficiency virus type 1 seroconversion," Journal of Clinical Microbiology, vol. 42, No. 6, pp. 2623-2628 (2004).
Dore-Duffy et al., "Expression of Endothelial Cell Activation Antigens in Microvessels from Pateints with Multiple Sclerosis," Frontiers in Cerebral Vascular Biology: Transport and Its Regulation, Plenum, pp. 243-248 (1993).
Dörries et al., "Infection of Human Polyomaviruses JC and BK in Peripheral Blood Leukocytes from Immunocompetent Individuals," Virology, 198:59-70 (1994).
Dörries et al., "Association of Human Polyomavirus JC with Peripheral Blood of Immunoimpaired and Healthy Individuals," Journal of NeuroVirology, 9(suppl. 1);81-87 (2003).
Dubois et al., "Detection of JC Virus DNA in the Peripheral Blood Leukocytes of HIV-infected Patients," AIDS 10:353-358 (1996).
Dubois et al., "Prevelance of JC Virus viraemia in HIV-infected patients with or without neurolgoical discorders: a prospective study", J of NeuroVirology, vol. 4, pp. 536-544 (1998).
Durez et al., Arthiritis Rheum., "Safety of Combination of Methotrexate (MTX) and Inflizimab (IFX) in a Large Legian Observational Patient Cohort with Refractory Rheumatoid Arthritis," vol. 46, No. 9S, p. 536 (2002).

(56) References Cited

OTHER PUBLICATIONS

Dworkin, "A Review of Progressive Multifocal Leukoencephalopathy in Persons With and Without AIDS," Curr. Clin. Top. Infect. Dis. 22:181-195 (2002).
Egli et al., "Prevalence of polyomavirus BK and JC infection and replication in 400 healthy blood donors", J. Infect 199:837-846, (2009).
Elices et al., "VCAM-1 on Activated Endothelium Interacts with the Leukocyte Integrin VLA-4 at a Site Distinct from the VLA-4/Fibronectin Binding Site," Cell, vol. 60, pp. 577-584 (1990).
Elphick et al., "The Human Polyomavirus, JCV, Uses Serotonin Receptors to Infect Cells," Science, vol. 306, pp. 1380-1383 (2004).
"The Encyclopedia of Blindness and vision impairment", 2nd Edition, 2002, Sardgna, Jill, and Otis, T. Paul, (2002).
Engelhardt, et al. "Therapeutic targeting of a4-integrins in chronic inflammatory diseases: tipping the scales of risk towards benefit?" Eur. J. Immunol., 35:2268-2273 (2005).
Engels et al., "Antibodies to JC and BK viruses among persons with non-Hodgkin lymphoma." Int. J. Cancer, vol. 117, pp. 1013-1019 (2005).
Enns et al., "Safety, Tolerability and Immunogenicity of Natalizumab in a Phase III Study of Active Crohn's Disease Therapy," Gastroenterology 126 (4, Suppl. 2): pA462 Apr. 2004.
Ernst et al., "Progressive Multifocal Leukoencephalopathy and Human Immunodeficiency Virus-associated White Matter Lesions in AIDS: Magnetization Transfer MR Imaging," Radiology 210:539-543 (1999).
Fedele et al., "Identical rearranged forms of JC polyomavirus transcriptionial control region in plasma and cerebrospinal fluid of acquired immunodeficiency syndrome patients with progressive multifocal leukoencephalopathy", J of NeroViology, vol. 9, pp. 551-558 (2003).
Ferguson et al., "Axonal damage in acute multiple sclerosis lesions," Brain, vol. 120, pp. 393-399 (1997).
Ferrante et al., "Detection of JC Virus DNA in Cerebrospinal Fluid from Multiple Sclerosis Patients," Multiple Sclerosis, 4:49-54 (1998).
Food and Drug Administration Label for Tysabri®—Revised May 24, 2013.
Foley, J., "Central Visual Disturbances", Developmental Medicine and Child Neurology, vol. 29, pp. 110-112—(1987).
Fox et al., "Advances in the management of PML: Focue on natalizumab," Cleveland clinic J. of Med., vol. 78(2), S33-S37 (2011).
Fox et al., "Risk stratification and patient counseling for natalizumab in multiple sclerosis", Neurology, vol. 78(6), pp. 436-437 (2012).
Frisque, Richard J., and White, Frank A.. "The molecular biology of JC virus, causative agent of progressive multifocal leukoencephalopathy." Molecular neurovirology. Humana Press, Totowa, NJ, (1992): 25-158.
Garrels et al., "Progressive Multifocal Leukoencephalopathy: Clinical and MR Response to Treatment," Am. J. Neuroradiol., vol. 17, pp. 597-600 (1996).
Geschwind et al., "The Relative Contributions of HAART and Alpha-interferon for Therapy of Progressive Multifocal Leukoencephalopathy in AIDS," J. Neurovirol. 7:353-357 (2001).
Gibson et al., "Detection of JC Virus DNA in the Cerebrospinal Fluid of Patients With Progressive Multifocal Leukoencephalopathy," J. Med. Virol. 39:278-281 (1993).
Gillespie et al., Progressive Multifocal Leukoencephalopathy in Persons Infected with Human Immunodeficiency Virus, San Francisco, 1981-1989, Annals of Neurology, vol. 30, No. 4, pp. 597-604 (1991).
Goelz et al., "Assay design and sample collection can affect anti-John Cunningham virus antibody detection." Ann. Neurol., vol. 69, No. 2 pp. 429-431 (2011).
Gold et al., "Expert opinion: Guidelines for the use of natalizumab in multiple sclerosis patients previously treated with immunomodulating therapies," J. of Neuroimmunology, vol. 187, pp. 156-158 (2007).
Goldenberg, Marvin M. "Multiple sclerosis review." Pharmacy and therapeutics 37.3 (2012): 175.
Goldman, et al., "Molecular cloning and expression of major structural protein VP1 of the human polyomavirus JC virus: formation of virus-like particles useful for immunological and therapeutic studies" Journal of Virology, vol. 73, No. 5, pp. 4465-4469 (1999).
Gorelik et al., "Anti-JC virus antibodies: implications for PML risk stratification." Am. Neurol. Assoc. 2010, vol. 68, pp. 295-303.
Harlow, et al., Using Antibodies: A Laboratory Manual: Portable Protocol I. Cold Spring Harbor Laboratory, Chapter p. 567-569 (Dec. 1, 1998).
Hemler et al., "VLA Proteins in the Integrin Famiy: Structures, Functions, and Their Role on Leukocytes," Annu. Rev. Immunol., vol. 8, pp. 365-400 (1990).
Henson et al., "Amplification of JC Virus DNA from Brain and Cerebrospinal Fluid of Patients with Progressive Multifocal Leukoencephalopathy," Neurology 41: 1967-1971 (1991).
Hernandez et al., "Treatment options for AIDS patients with progressive multifocal leukoencephalopathy", Expert Opin. Pharmacother. vol. 10(3), pp. 403-416 (2009).
Herndon, Robert M. "Natalizumab Returns." International Journal of MS Care 8.1 (2006): 31.
Hijazi et al., "Pharmacokinetics, Safety, and Tolerability of R411, a Dual a4131-a4137 Integrin Antagonist After Oral Administration at Single and Multiple Once-Daily Ascending Doses in Healthy Volunteers," J. Clin. Pharmacol., 44:1368-1378 (2004).
Hochberg, "A Sharper Bonferroni Procedure for Multiple Tests of Significance," Biometrika 75:800-802 (1988).
Hoe et al., "JC Virus Can Infect Human Immune and Nervous System Progenitor Cells: Inprications for Pathogenesis", Polyomaviruses and Human Diseases, Chapter 19, edited by Ahsan, Nasimul, pp. 266-273 (2006).
Hoffmann et al., "Progressive Multifocal Leucoencephalopathy with Unusual Inflammatory Response During Antiretroviral Treatment," J. Neurol. Neurosurg. Psychiatry 74:1142-1144 (2003).
Hoffman et al., PML-Falle unter Natalizumab (Tysabri)—(2005).
Hohlfeld et al., "Basic Principles of Immunotherapy for Neurologic Diseases," Seminars in Neurology, vol. 23, pp. 121-131 (2003).
Holman et al., Progressive Muutifocal Leukoencephalopathy in the United States, 1979-1994: Increased Mortality Associates with HIV Infection, Neuroepidemiology, vol. 17, pp. 303-309 (1998).
Hong et al., "Simple quantitative live cell and anti-idiotypic antibody based ELISA for humanized antibody directed to cell surface protein CD20", J of Immunol. Methods, vol. 294, pp. 189-197 (2004).
Hou et al., "JC Virus Can Infect Human Immune and Nervous System Progenitor Cells: Implications for Pathogensis", Polymaviruses and Human Diseases, Retinal Degenerative Diseases: Advances in Experimental Medicine and Biology, Ch. 19, vol. 577, pp. 266-273 (2006).
Hunt et al., "Natalizumab-associated progressive multifocal leucoencephalopathy: a practical approach to risk profiling and monitoring", Pract Neurol., vol. 12(1), pp. 25-35 (2012).
Huppke, Peter, et al. "Natalizumab use in pediatric multiple sclerosis." Archives of neurology 65.12 (2008): 1655-1658.
Hurley et al., "Identification of HIV-Associated Progressive Multifocal Leukoencephalopathy: Magnetic Resonance Imaging and Spectroscopy," J. Neuropsychiatry Clin. Neurosci. 15:1-6 (2003).
Hutchinson, "Natalizumab: A new treatment for relapsing remitting multiple sclerosis", Therapeutics and Clinical Risk Management, vol. 3, No. 2, pp. 259-268 (2007).
IFNB Multiple Sclerosis Study Group, "Interferon Beta-Ib is Effective in Relapsing-Remitting Multiple Sclerosis. I. Clinical Results of a Multicenter, Randomized, Double-blind, Placebo-controlled Trial," Neurology 43:655-661 (1993).
IFNB MS Study Group, Neutralizing antiodies during treatment of multiple sclerosis with interferon beta-1b: Experience during the first three years, Neurology, vol. 47, pp. 889-894 (1996).
Isaac et al., "Multiple Sclerosis: A Serial Study Using MRI in Relapsing Patients," Neurology 38:1511-1515 (1988).
Issekutz, Thomas B., "Lymphoctye homing to sites of inflammation," Curr. Opin. Immunol., vol. 4, pp. 287-293 (1992).

(56) References Cited

OTHER PUBLICATIONS

Jacobs et al., "Intramuscular Interferon Beta-Ia for Disease Progression in Relapsing Multiple Sclerosis," Annals of Neurology, 39:285-294 (1996).
Jilek at al.: "Immune responses to JC virus in patients with multiple sclerosis treated with natalizumab: a cross-sectional and longitudinal study", Lancet Neurology, vol. 9, pp. 264-272 (2010).
Johnson et al., "Copolymer 1 Reduces Relapse Rate and Improves Disability in Relapsimg-Remitting Multiple Sclerosis: Results of a Phase III Multicenter, Double-blind, Placebo-controlled Trial", Neurology 45:1268-1276 (1995).
Kannel et al., "Risk stratification of obesity as a coronary risk factor", Am. J. Cardiol., vol. 90, pp. 697-701 (2002).
Kappos et al., "Predictive Value of Gadolinium-enhanced Magentic Resonance Imaging for Relapse Rate and Changes in Disability or Impairment in Multiple Sclerosis: A Meta-analysis," Lancet, 353:964-969 (1999).
Kappos et al., "Neutralizing antidobies and efficacy of interferon β-1a", Neurology, vol. 65, pp. 40-47 (2005).
Kappos, Ludwig, et al. "Natalizumab treatment for multiple sclerosis: recommendations for patient selection and monitoring." The Lancet Neurology 6.5 (2007): 431-441.
Kean et al., "Seroepidemiology of Human Polyomaviruses", PLoS Pathogens, vol. 5, Issue 3 pp. 1-10 (2009).
Kent et al., "A Monoclonal Antibody to a4 Integrin Suppresses and Reverses Active Experimental Allergic Encephalomyelitis," J. Neuroimmunol. 58:1-10 (1995).
Khalili et al., "The Polyomavirus, JCV, and Its Involvement in Human Disease", Polyomaviruses and Human Diseases (2006).
Khanna, Nina, et al. "JC virus-specific immune responses in human immunodeficiency virus type 1 patients with progressive multifocal leukoencephalopathy." J Virol. (May 2009) 83(9):4404-11.
Khatri et al., ""Plasma Exchange Accelerates the Decline of Serum Natalizumab Concentration in Patients with Multiple Results of the Natalizumab PLEX Study"", Neurology, 70, pp. A227-A228, (2008).
Khatri, et al., 60th Annual Meeting of American Academy of Neurology, Chicago, Apr. 2008.
Khatri, et al., "Effect of plasma exchange in accelerating natalizumab clearance and restoring leukocyte function", vol. 72. No. 5, pp. 402-409 (2009).
Khoury et al., "Longitudinal MRI in Multiple Sclerosis: Correlation Between Disability and Lesion Burden," Neurology 44:2120-2124 (1994).
Kieseier et al., "Current disease-modifying therapies in multiple sclerosis," Seminars in Neurology, vol. 23, pp. 133-146 (2003).
Kitamura et al., "High Incidence of Urinary JC Virus Excretion in Nonimmunosuppressed Older Patients," J. Infect. Dis. 161:1128-1133 (1990).
King, David J. "Applications and engineering of monoclonal antibodies." CRC Press, 1998.
Kleinschmidt-Demasters et al., "Progressive Multifocal Leukoencephalopathy Complicationg Treatment with Natalizumab and Interferon Beta-Ia for Multiple Sclerosis," N. Engl. J. Med. 353:369-374 (2005).
Kleinschmidt-Demasters, B.K., et al. "Update on PML and PML-IRIS occurring in multiple sclerosis patients treated with natalizumab." J Neuropathol Exp Neurol. 71(7) (Jul. 2012):604-617.
Knowles et al., "The JC Virus Antibody Response in Serum and Cerebrospinal Fluid in Progressive Multifocal Leucoencephalophy," Journal of Clinical and Diagnostic Virology, 4:183-194 (1995).
Knowles et al., "Prevalence of Long-Term BK and JC Excretion in HIV-Infected Adults and Lack of Correlation With Serological Markers," J. Med. Virol. 59:474-479 (1999).
Knowles et al., "Comparison of cell culture-grown JC virus (primary human fetal glial cells and the JCI cell line) and recombinant JCV VP1 as antigen for the detection of anti-JCV antibody by haemagglutination inhibition," J. Virol. Methods, vol. 109, pp. 47-54 (2003).
Knowles et al., "Population-based study of antibody to the human polyomaviruses BKV and JCV and the Simian polyomavirus SV40." J. Med. Virol. , vol. 71, pp. 115-123 (2003).
Knowles, Wendy, "Discovery and Epidemiology of the Human Polyomaviruses BK Virus (BKV) anf JC Virus (JCV)", Polymaviruses and Human Diseases, Ch. 2, pp. 19-45 (2006).
Koralnik, I. J., et al. "JC virus DNA load in patients with and without progressive multifocal leukoencephalopathy." Neurology 52.2 (1999): 253-260.
Koralnik, Igor J., et al. "JC virus-specific cytotoxic T lymphocytes in individuals with progressive multifocal leukoencephalopathy." Journal of virology 75.7 (2001): 3483-3487.
Koralnik, "New Insights Into Progressive Multifocal Leukoencephalopathy," Current Opinion in Neurology, 17:365-370 (2004).
Koren et al., "Recommendations on risk-based strategies for detection and characterization of antibodies biotechnology products" Journal of Immunological Methods, vol. 333,Nr:1-2,pp. 1-9 (2008).
Kornek et al., "Multiple Sclerosis and Chronic Autoimmune Encephalomyelitis—A Comparative Quantitative Study of Aconal Injury in Active, Inactive, and Remyelinated Lesions," Amer. J. Pathalogy, vol. 157, No. 1, pp. 267-276 (2000).
Kozovska et al., "Interferon Beta Induces T-helper 2 Immune Deviation in MS," Neurology 53:1692-1697 (1999).
Kromidas, S., "Validation in analytics," Wiley-VCH Verlag, Apr. 1999, pp. 176-181, 250-251.
Labrijin et al., "Therapeutic IgG4 antibodies engage in Fab-arm exchange with endogenous human IgG4 in vivo", Nature Biotechnology, vol. 27, No. 8, pp. 767-773 (2009).
Langer-Gould et al., "Progressive Multifocal ALeukoencephalopathy in a Patient Treated with Natalizumab," N. Eng. J. Med. 353:375-381 (2005).
Lee et al., "An enhanced ELISA for detection of anti-JC virus antibodies in human serum and plasma to support progressive multifocal leukoencephalopathy risk stratification", Poster, 22nd Meeting of European Neurological Society, p. 467 (2012).
Lee et al., "A second-generation ELISA (Stratify JCV™ DxSelect™) for detection of JC virus antibodies in human serum and plasma to support progressive multifocal leukoencephalopathy risk stratification", Journal of Clinical Virology, vol. 57, pp. 141-146 (2013).
Lima, Marco A. and Koralnik, Igor J., "New features of progressive multifocal leukoencephalopathy in the era of highly active antiretroviral therapy and natalizumab", J of NeuroViorlogy, vol. 11(suppl. 3), pp. 52-57 (2005).
Ling et al., "The dynamics of herpesvirus and polyomavirus reactivation and shedding in healthy adults: a 14-month longitudinal study." J. Infect. Diseases, vol. 187, pp. 1571-1580 (2003).
Lobb, R.R. and Hemler, M.E., "The Pathophysiologic Role of α4 Integrins In Vivo," J. Clin. Invest., vol. 94, pp. 1731-1735 (1994).
Lundstig, Annika, and Dilner, Joakim, et al., "Serological Diagnosis of Human Polymavirus Infection", Polymaviruses and Human Diseases, Ch. 7, pp. 96-101 (2006).
Major, "Progressive Multifocal Leukoencephalopathy in Patients on Immunomodulatory Therapies", Annu. Rev. Med. (2010), Aug. 31, 2009, Epub ahead of print.
Mamidi et al., "Central Nervous System Infections in Individuals with HIV-I Infection," J. Neurovirol. 8:158-167 (2002).
Manji, H. and Miller, R.F., "Progressive multifocal leucoencephalopathy: progress in the AIDS era," J. of Neurosurgery & Psychiatry, vol. 69, pp. 569-571 (2000).
McDonald et al., "Recommended Diagnostic Criteria for Multiple Sclerosis: Guidelines from the International Panel on the Diagnosis of Multiple Sclerosis," Ann. Neurol., 50:121-127 (2001).
McFarland et al., "The Role of MRI as a Surrogate Outcome Measure in Multiple Sclerosis," Multiple Sclerosis 8:40-51 (2002).
McGuire et al., "JC Virus DNA in Cerebrospinal Fluid of Human Immunodeficiency Virus-infected Patients: Predictive Value for Progressive Multifocal Leukoencephalopathy", Annals of Neurology, vol. 37, No. 3, pp. 395-399 (1995).
Miller et al., "A Controlled Trial of Natalizumab for Relapsing Multiple Sclerosis," N. Engl. J. Med. 348:15-23 (2003).

(56) References Cited

OTHER PUBLICATIONS

Miller D H: "Colloquium C15: Natalizumab (anti-VLA4 antibody) in multiple sclerosis", Journal of Neurochemistry, Wiley Interscience, New York, NY, US, vol. 85, No. Suppl. 1, Jan. 1, 2003, p. 96, C15-04.
Millipore, "Short Guide for Developing Immunochromatographic Test Strip", (1996).
Mire-Sluis et al., "Recommendations for the design and optimization of immunassays used in the detection of host antibodies against biotechnology products," Journal of Immunological Methods, vol. 289, pp. 1-16 (2004).
Molyneux et al., "Correlations between Monthly Enhanced MRI Lesion Rate and Changes in T2 Lesion Volume in Multiple Sclerosis," Ann. Neurol., 43:332-339 (1998).
Montross et al.: Nuclear Assembly of Polyomavirus Capsids in Insect Cells Expressing the Major Capsid Protein Journal of Virology (Sep. 1991), vol. 65, No. 9, pp. 4991-4998.
Niino et al., "Natalizumab Effects on Immune Cell Responses in Multiple Sclerosis", Annals of Neurology, vol. 59, No. 5, pp. 748-754 (2006).
Olsen et al., "White Matter Disease in AIDS: Findings at MR Imaging," Radiology 169:445-448 (1988).
Olsson et al., Anti-JCV antibody prevelance in a Swedish cohort of MS pateients and non-MS controls.:, Mult Scler J 16: S38-S39 (2010).
O'Neille, "Expression of vascular addressins and ICAM-1 by endothelial cells in the spinal cord during chronic relapsing experimental allergic encephalomyelitis in the Biozzi AB/H mouse," Immunology, vol. 72, pp. 520-525 (1991).
Oriordan et al., "The prognostic value of brain MRI in clinically isolated syndromes of the CNS," Brain, vol. 121, pp. 495-503 (1998).
Ou et al.: "The major capsid protein, VP1, of human JC virus expressed in *Escherichia coli* is able to self-assemble into a capsid-like particle and deliver exogenous DNA into human kidney cells", Journal of General Virology, vol. 80, pp. 39-46 (1999).
Padgett, B.L., et al. "Cultivation of papova-like virus from human brain with progressive multifocal leucoencephalopathy." Lancet. Jun. 19, 1971;1(7712):1257-60.
Padgett et al., "Prevalence of antibodies in human sera against JC virus, an isolate from a case of progressive leukoencephalopathy", J. Infect. Dis. 127:467-70 (1973).
Padgett et al., "Virologic and Serologic Studies of Progressive Multifocal Leukoencephalopathy," Prog. Clin. Biol. Res. 105:107-117 (1983).
Palkhivala, Alison, "A Case of PML in a Natalizumab-Treated MS Patient", Sep. 22, 2008, downloaded from www.medscape.com on Apr. 2, 2021.
Patton et al., "An acid dissociation bridging ELISA for detection of antibodies directed against therapeutic proteins in the presence of antigen", Journal of Immunological Methods, vol. 304, pp. 189-195 (2005).
Pepio, Anthony M., et al. "Evaluation of the incidence of anti-JC virus antibodies in a cohort of natalizumab-treated patients." Gastroenterology 5.140 (2011): S-768.
Pestalozza et al., "Monthly brain magnetic resonance imaging scans in patients with clinically isolated syndrome," Multiple Sclerosis, vol. 11, pp. 390-394 (2005).
Petterson et al., "VCAM-1-Positive Microglia Target Oligodendrocytes at the Border of Multiple Sclerosis Lesions," J. Neuropathy Exp. Neurol., vol. 61, No. 6, pp. 539-546 (2002).
Piccinni, et al., "Stronger association of drug-induced progressive multifocal leukoencephalopathy (PML) with biological immunomodulating agents", Eur. J. Clin. Pharmacol. 66:199-206 (2010).
Plavina et al., "Multi-site analytical validation of an assay to detect anti-JCV antibodies in human serum and plasma", J. Clinical Viorlogoy, vol. 53, p. 65-71 (2012).
Plavina et al., "Anti-JCV antibody index further defines PML risk in natalizumab-treated MS pateients," The 27th Annual Meeting of the Corsortium of Multiple Sclerosis Centers Acknowledgements, Accessed March Neurology, Wamke C J Neurol Neurosurg Psychiartry Ann Neurol, May 30, 2013, pp. 1736-1742.
Plavina et al., Serum Concentration of Natalizumab, Endogenous IgG4, and sVCAM-1 in Natalizumab-Treated PML Patients (P05.159), Neurology, vol. 80 (7 Supplement), 2013).
Pleasure, S.J. Dangers of stopping natalizumab (Tysabri) (2011), published at boards.medscape.com/forums?128@432.MhQkdtpt HuD@.2a0a4eec!comment=1 _ Jun. 10, 2011.
Polman et al., "A Randomized, Placebo-Controlled Trail of Natalizumab for Relapsing Multiple Sclerosis," N. Engl. J. Med., 354(9):899-910 (2006).
Post et al., "Progressive Multifocal Leukoencephalopathy in AIDS: Are There Any MR Findings Useful to Patient Management and Predictive of Patient Survival?," Am. J. Neuroradiol. 20:1896-1906 (1999).
Prisms Study Group, "Randomised Double-blind Placebo-controlled Study of Interferon 13-Ia in Relapsing/Remitting Multiple Sclerosis," Lancet 352:1498-1504 (1998).
Prisms Study Group, "PRIMSMS-4: Long-term efficacy of interferon-β-1a in relapsing MS," Neurology, vol. 56, pp. 1628-1636, , (2001).
Przepiorka et al., "Successful Treatment of Progressive Multifocal Leukoencephalopathy with Low-Dose Interleukin-2," Bone Marrow Transplant, 20:983-987 (1997).
Public Health Advisory—Suspended Marketing of Tysabri (Natalizumab), Feb. 28, 2005.
Pucci, Eugenio, et al. "Natalizumab for relapsing remitting multiple sclerosis." Cochrane Database of Systematic Reviews 10 (2011):1-44.
Raffel et al, "Assay Selction Affects John Cunningham Virus Serostatus Classification in Multiple Sclerosis," Annals of Neurology vol. 72, No. 2, pp. 295-296 (2012).
Raine et al., "Homing to Central Nervous System Vasculature by Antigen-Specific Lymphocytes—II. Lyphocyte/Endothelical Cell Adhesion during the Intitial Stages of Autoimmune Demyelination," Lab Invest. vol. 63, No. 4, pp. 476-489 (1990).
Rankin et al., "Progressive Multifocal Leukoencephalopathy in a Pateitn with Rheumatoid Arthritis and Polymyositis," J. Rheumatol, vol. 22, pp. 777-779 (1995).
Ransohoff, Richard M. "Natalizumab and PML." Nature neuroscience 8.10 (2005): 1275.
Redington et al., "Viral Infections of the Nervous System, 2002," Arch. Neurol. 59:712-718 (2002).
Rep et al., "Recombinant Interferon-B Blocks Proliferation but Enhances Interleukin-10 Secretion by Activated Human T-Cells," J. Neuroimmunol. 67:111-118 (1996).
Rispens et al., "Measurement of serum levels of natalizumab, an immunoglobulin G4 therapeutic monoclonal antibody", Analytical Biochemistry, vol. 411, pp. 271-276 (2011).
Rollison Dana E et al: "'Prediagnostic circulating antibodies to JC and BK human polyomaviruses and risk of non-Hodgkinlymphoma. '", Cancer Epidemiology, Biomarkers & Prevention: A Publication of the American Association for Cancer Research, Cosponsored by the American Society of Preventive Oncology, vol. 15, No. 3, pp. 543-550 (2006).
Rudick et al., "Incidence and Significance of Neutralizing Antibodies to Interferon Beta-1a in Multiple Sclerosis," Neurology 50:1266-1272 (1998).
Rudick et al., "Natalizumab plus Interferon Beta-1a for Relapsing Multiple Sclerosis," N. Engl. J. Med., 354(9):91 1-923 (2006).
Runmarker, B. and Andersen, O., "Prognostic factors in a multiple sclerosis incidence cohort with twenty-five years of follow-up," Brain, vol. 116, pp. 117-134 (1993).
Ryschkewitsch et al., "JC virus persistence following progressive multifocal leukoencephalopathy in multiple sclerosis patients treated with natalizumab", Ann Neurol., vol. 68(3), pp. 384-391 (2010).
Sadiq et al, "JCV detection in multiple sclerosis patients treated with natalizumab," J Neurol, vol. 257, pp. 954-958 (2010).
Sailer et al., "Quantitative MRI in patients with clinically isolated syndromes suggestive of demyelination," Neurology, vol. 52, pp. 599-606 (1999).

(56) References Cited

OTHER PUBLICATIONS

Salmaggi et al., "Reversal of CSF Positivity for JC Virus Genome by Cidofovir in a Patient with Systemic Lupus Erthematosus and Progressive Multifocal Leukoencephalopathy," Neurol. Sci. 22:17-20 (2001).
Salunke et al., "Polymorphism in the Assembly of Polyomavirus Capsid Protein VP", Biophys Journal, vol. 56, pp. (1989).
Sandborn et al., "Efficacy of Natalizumab in Maintaining Clinical Response and Remission in Crohn's Disease: Comparison of Sustained Response and Remission Rates Through 12 Months Vs Point-In-Time Response and Remission Rates at Month 12," Gastroenterology, vol. 128, No. 4, Suppl. 2, p. A586 (2005).
Sandrock et al.: Risk Stratification for Progressive Multifocal Leukoencephalopathy (PML) in MS Patients: Role of Prior Immunosuppressant Use, Natalizumab-Treatment Duration, and Anti-JCV Antibody Statue, Neurology, vol. No. 9, Suppl. 4, Mar. 2011 (Mar. 2011), p. A248, 63rd Annual Meeting of the American Academy of Neurology; Honolulu, HI, USA; Apr. 9-16, 2011.
Sandrock, et al., "Risk of Natalizumab-Associated Progressive Multifocal Leukoencephalopathy" 25th Annual Meeting the Consortium of Multiple Sclerosis Centers, Jun. 1-4, 2011 Montreal, Quebec, Canada.
Schuurman et al., "Normal human immunoglobulin G4 is bispecific: it has two different antigen-combining sites," Immunology, 97:693-698 (1999).
Selewski, D. T., et al. "Natalizumab (Tysabri)." American journal of neuroradiology 31.9 (2010): 1588-1590.
Seth et al., "Advances in the Biology of JC Virus and Induction of Progressive Multifocal Leukoencephalopathy," J. Neurovirol. 9:236-246 (2003).
Shapiro et al., "Development and validation of immunoassays to quantify the half-antibody exchange of an IgG4 antibody, natalizumab (Tysabri) with endogenous IgG4", J. Pharm and Biomedical Analysis, vol. 55, pp. 168-175 (2011).
Shitrit et al., "Progressive Multifocal Leukoencephalopathy in Transplant Recipients," Transpl. Int. 17:658-665 (2005).
Simon et al., "A Longitudinal Study of T1 Hypointense Lesions in Relapsing MS," Neurology 55:185-192 (2000).
Sospedra, Mireia, and Martin, Roland. "Immunology of multiple sclerosis." Annu. Rev. Immunol. 23(2005): 683-747.
Sponzilli et al., Progressive multifocal leukoencephalopath: A complication of immunosuppressive treatment, Neurology, vol. 25, pp. 664-668 (1975).
Springer, Timothy A., "Traffic Signals for Lymphocyte Recirculation and Leukocyte Emigration: The Multistep Paradigm," Cell, vol. 76, pp. 301-314 (1994).
Stavnezer J. "Antibody class switching." Adv Immunol. (1996); 61:79-146.
Steffen et al., "Evidence for Involvement of ICAM-1 and VCAM-1 in Lymphocyte Interaction with Endothelium in Experimental Autoimmune Encephalomyelitis in the Central Nervous System in the SJL/J Mouse," Amer. J. Pathology, vol. 145, No. 1, pp. 189-201 (1994).
Steinman, Lawrence, "Blocking adhesion molecules as therapy for multiple sclerosis: natalizumab," Nature Reviews. Drug Discovery, Nature Publishing Group, GB, vol. 4, No. 6, pp. 510-518 (2005).
Stolt et al.: "Seroepidemiology of the human polyomaviruses", Journal of General Virology (2003), vol. 84, pp. 1499-1504.
Stone, John H., "IgG4-related disease: pathophysiologic insights drive emerging treatment approaches," Clin. Exp. Rheumatol. vol. (Suppl 98), pp. 1-3 (2016).
Stuve, et al., "Potential Risk of Progressive Multifocal Leukoencephalopathy With Natalizumab Therapy", Arch vol. 64, (Feb. 2007). P9 169-176.
Subramanyam, M., et al. "Factors associated with anti-JCV antibody prevalence in a large cohort of natalizumab-treated MS patients." Mult Scler 16 (2010): S38-S39.
Subramanyam et al.: "Anti-JCV Antibodies Are Consistently Detected Prior to and after PML Diagnosis in Natalizumab-Treated MS Patients", Neurology, vol. 76, No. 9, Suppl. 4, Mar. 2011 (Mar.

2011), pp. A636-A637, 63rd Annual Meeting of the American Academy of Neurology; Honolulu, HI, USA; Apr. 9-16, 2011.
Summary of Product Characteristics (SmPC) Tysabri.
Sundsfjord et al., "BK and JC Viruses in Human Immunodeficiency Virus Type 1-Infected Persons : Prevalence, Excretion, Viremia, and Viral Regulatory Regions," J. Infect. Dis. 169:485-490 (1994).
Takada, et al., "The integrins", Genome Biol. 8:215 (2007).
Tan I.L., et al. "Immune reconstitution inflammatory syndrome in natalizumab-associated PML." Neurology. Sep. 13, 2011;77(11):1061-1067.
Tan & Koralnik, "Beyond progressive multifocal leukoencephalopathy: expanded pathogensis of JC virus infection in the central nervous system", Lancet Neurol., vol. 9(4), pp. 425-437 (2010).
Tantisiriwat et al., "Progressive Multifocal Leukoencephalopathy in Patients with AIDS Receiving Highly Active Antiretroviral Therapy," Clin. Infect. Dis. 28:1152-1154 (1999).
Tenser, R.B. et al., "Natalizumab for Relapsing Multiple Sclerosis," New Engl. J. Med., 354(22):2387-2389 (2006).
The Immunoassay Handbook, Third Edition (2005).
Thompson et al., "Major Differences in the Dynamics of Primary and Secondary Progressive Multiple Sclerosis," Ann. Neurol. 29:53-62 (1991).
Thompson et al., "Serial Gadolinium-Enhanced MR1 in Relapsing/Remitting Multiple Sclerosis of Varying Disease Duration," Neurology 42:60-63 (1992).
Tornatore et al., "Detection of JC Virus DNA in Peripheral Lymphocytes from Patients with and without Progressive Multifocal Leukoencephalopathy," Ann. Neurol., 31:454-462 (1992).
Trampe et al., "Anti-JC virus antibodies in a large German natalizumab-treated multiple sclerosis cohort," Neurology, vol. 78(22), pp. 1736-1742 (2012).
Trapp et al., "Axonal Transection in the Lesions of Myultiple Sclerosis," N.E. J. of Medicne, vol. 338, pp. 278-285 (1998).
Tur and Montalban, "Natalizumab: Risk Stratification of Individual Patients with Multiple Sclerosis." CNS Drugs, vol. 28, pp. 641-648 (2014).
Tysabri (natalizumab) product label (revised Dec. 2009).
Tyler, Kenneth L. "The uninvited guest: JC virus infection of neurons in PML." Neurology 61.6 (2003): 734-735.
Tyler "Progressive multifocal leukoencephalopathy: can we reduce risk in patients receiving biological immunomodulatory therapies?" Ann Neurol., vol. 68(3), pp. 271-274 (2010).
Vago et al., "JCV-DNA and BKV-DNA in the CNS Tissue and CSF of AIDS Patients and Normal Subjects. Study of 41 Cases and Review of the Literature," J. Acquir. Imm. Defic. Syndr. Hum. Retrovirol. 12:139-146 (1996).
Van Assche et al., "Physiological Basis for Novel Drug Therapies Used to Treat the Inflammatory Bowel Diseases: I. Immunology and therapeutic potential of antiadhesion molecule therapy in inflammatory bowel disease," Am. J. Physiol. Gastrointest. Liver Physiol., 288:G169-G174 (2005).
Van Assche, "Progressive Multifocal Leukoencephalopathy After Natalizumab Therapy for Crohn's Disease", The New England Journal of Medicine, vol. 353, No. 4, pp. 362-368, (2005).
Verbeeck J et al: "JC viral loads in patients with Crohn's disease treated with immunosuppression: can we screen for elevated risk of progressive multifocal leukoencephalopathy?", Gut vol. 57, No. 10, Oct. 2008.
Viscidi, "Serological Cross-Reactivities between Antibodies to Simian Virus 40, BK Virus, and JC Virus Assessed by Virus-Like-Particle-Based Enzyme Immunoassays", Clinical and Diagnostic Laboratory Immunology, vol. 10, No. 2, pp. 278-285, (2003).
Viscidi, Raphael P, et al. "Serological Cross Reactivity between Polyomavirus Capsids", Advances in Experimental Medicine and Biology, vol. 577, chapter 5, pp. 73-84 (2006).
Viscidi, Raphael P, et al. "JC virus antibody and viremia as predictors of progressive multifocal leukoencephalopathy in human immunodeficiency virus-1-infected individuals." Clin Infect Dis. (Oct. 2011) 53(7):711-715.
Von Andrian et al., "α4 Integrins as Therapeutic Targets in Autoimmune Disease" N. Engl. J. Med., 348(1):68-72 (2003).
Waknine, Yael, "Tysabri Suspended From U.S. Market", Feb. 28, 2005, downloaded from www.medscape.com on Apr. 6, 2021.

(56) References Cited

OTHER PUBLICATIONS

Warnke et al.: "Natalizumab and progressive multifocal leukoencephalopathy: what are the causal factors and can it be avoided?", Archives of Neurology, vol. 67, No. 8, Aug. 1, 2010 (Aug. 1, 2010), pp. 923-930.

Washington et al., "Expression of Immunologically Relevant Endothelial Cell Activation Antigens on Isolated Central Nervous System Microvessels from Patients with Multiple Sclerosis," Ann. Neurol., vol. 35, pp. 89-97 (1994).

Weber et al., "Progressive Multifocal Leukoencephalopathy Disgnosed by Amplification of JC Virus-specific DNA from Cerebrospinal Fluid," AIDS 8:49-57 (1994).

Weber et al., "Specific Diagnosis of Progressive Multifocal Leukoencephalopathy by Polymerase Chain Reaction," J. Infect. Dis. 169:1138-1141 (1994).

Weber T et al: "Analysis of the systemic and intrathecal humoral immune response in progressive multifocal leukoencephalopathy.", The Journal of Infectious Diseases vol. 176, No. 1, Jul. 1997 pp. 250-254.

Weber et al., "Immune response in progressive multifocal leukoenecphalopathy: an overview,.", Journal of neurovirology 7/4, pp. 3111-3317 (2001).

Wenning, et al., Treatment of Progressive Multifocal Leukoencephalopathy Associated with Natalizumab, N Engl J Med, vol. 361. No. 11. (Sep. 10, 2009), p. 1075-1080.

Whitaker et al., "Outcomes Assessment in Multiple Sclerosis Clinical Trials: a Critical Analysis," Multiple Sclerosis, 1:37-47 (1995).

Willoughby et al., "Serial Magnetic Resonance Scanning in Multiple Sclerosis: A Second Prospective Study in Relapsing Patients," Ann. Neurol., 25:43-49 (1989).

Wright et al., "Standardisation and validation of enzyme-linked immunosorbent assay techniques for the detection of antibody in infections disease diagnosis," Rev. Sci. Tech. Off. Int. Epiz., vol. 12(2), pp. 435-450 (1993).

Yednock et al., "Prevention of Experimental Autoimmune Encephalomyelitis by Antibodies Against a4131 Integrin," Nature 356:63-66 (1992).

Yednock—Internet disclosure of Matthew Harper in the Forbes Magazine entitled "reviving Tysabri" published on Oct. 27, 2009 (interview with Ted Yednock); https://www.forbes.com/2009/10/27/ms-crohn-elan-business-healtcare-tysabri-html?sh=7ae482d13606.

Yousry et al., "Evaluation of Patients Treated with Natalizumab for Progressive Multifocal Leukoencephalopathy," New England Journal of Medicine, vol. 354: 924-933 (2006).

Yu et al., "How Natalizumab Binds and Antagones a4 Integrins*", J of Bioglogical Chemistry, vol. 288, No. 45, pp. 32314-32325 (2013).

Zang et al., "Regulation of Chemokine Receptor CCR5 and Production of RANTES and MIP-la by Interferon-B," J. Neuroimmunol. 112:174-180 (2001).

Zu Rhein, G. M., and Chou, S.M. "Particles resembling papova viruses in human cerebral demyelinating disease." Science 148. 3676 (1965): 1477-1479.

METHOD OF ASSESSING RISK OF PML

CROSS-REFERENCE TO RELATED APPLICATIONS

This application claims the benefit of U.S. Provisional Application No. 61/828,021, filed May 28, 2013, the entire contents of which are incorporated herein by reference.

FIELD OF THE INVENTION

The invention relates to methods of assessing a patient's risk of developing Progressive multifocal leukoencephalopathy (PML).

BACKGROUND OF INVENTION

The anti-VLA-4 (Very Late Antigen 4) antibody therapeutic natalizumab is indicated to treat relapsing forms of multiple sclerosis (MS) and moderate-to-severe Crohn's Disease. Natalizumab treatment, however, is associated with an increased risk of progressive multifocal leukoencephalopathy (PML), an opportunistic brain infection caused by the JC virus (JCV). PML occurs primarily in immunocompromised individuals and in patients receiving certain immunomodulatory therapies, including natalizumab. PML is hypothesized to be the result of a complex interaction between host and viral factors, leading to reactivation and mutation of latent archetype JCV to a neurotrophic form which can infect oligodendrocytes in the central nervous system.

SUMMARY OF INVENTION

The invention relates, inter alia, to an optimized analytically validated, sensitive assay for detecting the presence of JCV antibodies in a biological fluid, e.g., serum or plasma and to various other methods, including methods of evaluating and/or treating patients.

Accordingly, in one aspect, the invention features, a method of evaluating a patient's risk of developing Progressive Multifocal Leukoencephalopathy (PML), the method comprising: determining a JC virus (JCV) antibody titer in a biological sample from the patient (e.g., by a method described herein), wherein the patient has a negative prior immunosuppressant exposure classification; wherein if the titer is determined to be above a pre-determined level, e.g., above an index level of 0.7, 0.8, 0.9, 1.0, 1.1, 1.2, 1.3, 1.4, or 1.5, the patient is determined to be at a higher risk of developing PML, and wherein if the titer is determined to be at or below a pre-determined level, e.g., at or below an index level of 1.5, 1.4, 1.3, 1.2, 1.1, 1.0, 0.9, 0.8, or 0.7, the patient is determined to be at a lower risk of developing PML. In some embodiments, the pre-determined level is 0.9. In some embodiments, the pre-determined level is 1.2. In some embodiments, the pre-determined level is 1.5.

In some embodiments, the patient has been free of a non-anti-VLA-4 immunosuppresant therapy for a period within 1, 3, or 5 years. In some embodiments, the patient has been free of a non-anti-VLA-4 immunosuppressant therapy for the patient's lifetime, or since diagnosis with multiple sclerosis (e.g., relapsing, remitting multiple sclerosis).

In some embodiments, the patient has multiple sclerosis (e.g., relapsing, remitting multiple sclerosis).

In another aspect, the present invention provides a method of evaluating a patient's risk of developing PML, the method comprising: determining a JC virus (JCV) antibody titer (e.g., by a method described herein) in two or more biological samples obtained from the patient over a period of time (e.g., 2, 3, 4, 5, 6, 7, 8, 9, 10, 11, 12, 13, 14, 15, 16, 17, 18, 19, 20, 21, 22, 23, 24 or more months); wherein if the titer is determined to be above zero, but at or below a pre-determined level, e.g., at or below an index level of 1.5, 1.4, 1.3, 1.2, 1.1, 1.0, 0.9, 0.8, or 0.7, in the two or more samples, the patient is determined to be at a lower risk of developing PML, and wherein if the titer is determined to be above a pre-determined level, e.g., above an index level of 0.7, 0.8, 0.9. 1.0, 1.1, 1.2, 1.3, 1.4, or 1.5, in the two or more samples, the patient is determined to be at a higher risk of developing PML. In some embodiments, the pre-determined level is an index level of 0.9. In some embodiments, the pre-determined level is an index level of 1.2. In some embodiments, the pre-determined level is an index level of 1.5.

In various embodiments, the period of time is 6 months. In various embodiments, the period of time is 12 months. In various embodiments, the period of time is 18 months. In some embodiments, the patient has received an anti-VLA4 during the period of time.

In certain embodiments, the two or more samples are consecutive samples. In some embodiments, the titer in every sample obtained from the patient over a period of time is determined to be at or below a pre-determined level. In some embodiments, the titer in every sample obtained from the patient over a period of time is determined to be above a pre-determined level.

In some embodiments, the patient has a negative prior immunosuppressant exposure classification. In some embodiments, the patient has been free of a non-anti-VLA-4 immunosuppresant therapy (e.g., immunosuppressant therapy) for a period within 1, 3, or 5 years. In some embodiments, the patient has been free of a non-anti-VLA-4 immunosuppressant therapy (e.g., immunosuppressive therapy) for the patient's lifetime, or since diagnosis with multiple sclerosis (e.g., relapsing, remitting multiple sclerosis).

In some embodiments, the patient has multiple sclerosis (e.g., relapsing, remitting multiple sclerosis).

In some embodiments, if the patient is determined to be at lower risk of developing PML, then the patient is classified as being suitable for treatment with an anti-VLA4 therapy. In particular embodiments, the method further includes administering an anti-VLA4 therapy to the patient. In certain embodiments, the anti-VLA4 therapy is a natalizumab therapy. In some embodiments, the patient has previously received an anti-VLA4 therapy.

In some embodiments, the method further comprises providing information regarding the patient's classification, e.g., the patient's JCV titer, and, optionally, the patient's immunosuppressant exposure classification to another party, e.g., a health care provider or reimbursement decider (e.g., an insurance or government agency).

In one embodiment, the patient's JCV antibody titer is above a predetermined level in a sample, and below a predetermined level in a second subsequent sample, and, e.g., the patient is classified as being suitable for treatment with an anti-VLA4 therapy (e.g., natalizumab). In one embodiment, the patient's JCV antibody titer is below a predetermined in level in two or more samples, and, e.g., the patient is classified as suitable for treatment with an anti-VLA4 antibody (e.g., natalizumab). In one embodiment, the patient's JCV antibody titer is above at predetermined level in a sample, and is above a predetermined level in a second subsequent sample, and, e.g., the patient is classified as not being suitable for treatment with an anti-VLA4 therapy (e.g., natalizumab).

In another aspect, the invention features a method of evaluating the level of anti-JCV antibody in a sample. The method comprises one or more or all of the following steps:

(a) forming a first reaction mixture comprising a first aliquot of sample and a substrate on which is disposed HPVLP (Highly Purified Viral-Like Particle, e.g., Highly Purified VP1 Particle), e.g., a high signal-to-noise HPVLP substrate;

(b) detecting the level of anti-JCV antibody bound to said substrate on which is disposed HPVLP, e.g., a high signal-to-noise HPVLP substrate, e.g., by detecting a labeled detection reagent, e.g., an enzyme labeled anti-IgG antibody, bound to anti-JCV antibody bound to said substrate; thereby evaluating the level of anti-JCV antibody in a sample (as is discussed herein, the method can comprise classifying, or assigning, to the sample, a value indicative of the level of anti-JCV antibody, which value is sometimes referred to herein as an index value. The value can be used to evaluate the sample or a patient and in embodiments, to determine whether to proceed to an additional step of the method, e.g., step (c) below); and (c) forming a second reaction mixture containing a second aliquot of sample and solution-phase HPVLP, and detecting the level of unbound anti-JCV antibody in said second reaction mixture, such as by detecting anti-JCV antibody capable of binding with a substrate on which is disposed HPVLP, e.g., a high signal-to-noise HPVLP substrate (as is discussed herein, the method can comprise classifying, or assigning, to the sample, a value indicative of the degree to which incubation with the soluble-phase HPVLP reduces the level of unbound anti-JCV antibody in the second reaction mixture, which value is sometimes referred to herein as inhibition, % inhibition, or the like. This value can be used to evaluate the sample or a patient), thereby evaluating the level of anti-JCV antibody in a sample.

In an embodiment the method further comprises:

(d) forming a third reaction mixture containing a third aliquot under conditions where anti-JCV antibodies in the sample are not bound by HPVLP or other antigen, and detecting the level of anti-JCV antibody in the third reaction mixture, such as by detecting anti-JCV antibody capable of binding with a substrate on which is disposed HPVLP, e.g., a high signal-to-noise HPVLP substrate. The inhibition or % inhibition can be calculated as a function of the degree that incubation with soluble-phase HPVLP (step (c)) reduces the amount of unbound anti-JCV antibody, as compared to the result in step (d).

In an embodiment the method comprises steps (a) and (b), and optionally, providing the results to another entity, e.g., a healthcare provider.

In an embodiment the method comprises steps (a), (b), and (c), and optionally, providing the results to another entity, e.g., a healthcare provider.

In an embodiment the method comprises steps (a), (b), (c), and (d), and optionally, providing the results to another entity, e.g., a healthcare provider.

In an embodiment the method comprises step (c) and optionally providing the results to another entity, e.g., a healthcare provider.

In an embodiment the method comprises step (c) and (d), and optionally, providing the results to another entity, e.g., a healthcare provider.

Methods described herein use optimized levels and amounts of reagents, allowing for improved performance. Thus, in an embodiment, for the first reaction mixture, 20 ngs to 60 ngs, 30 ngs to 50 ngs, 20 ngs to 40 ngs, 35 ngs to 45 ngs of HPVLP are disposed on said substrate. In an embodiment about 20 ngs, 30 ngs, 40 ngs, 50 ngs or 60 ngs of HPVLP are disposed on said substrate. Typically, a multi-substrate device, e.g., a multi-well plate, e.g., a polystyrene multi-well plate, will have an amount of HPVLP specified herein on each of a plurality of substrates. A typical substrate is the interior of a well on a multi-well plate.

Methods described herein use optimized ratios of reagents and sample, allowing for improved performance. In an embodiment the ratio of µl of sample (this refers to undiluted sample, or the amount of sample in a dilution, so 100 µl of a 1 µl:100 µl dilution would be 1 µl of sample), e.g., serum or plasma, to ngs of HPVLP disposed on the substrate in the first reaction is: between 1:100 and 1:20; 1:80 and 1:30; 1:60 and 1:20; 1:20 and 1:60; 1:30 and 1:50. In an embodiment the ratio of µl of sample, e.g., serum or plasma, to ngs of HPVLP disposed on the substrate is about: 1:30, 1:40, or 1:50. In an embodiment the ratio of µl of sample, e.g., serum or plasma, to ngs of HPVLP disposed on the substrate is about: (0.08 to 1.2): 30, (0.08 to 1.2): 40, or (0.08 to 1.2): 50.

In one embodiment, the sample, e.g., serum, for the first reaction is diluted, such as by about 100-fold, in buffer, for example, prior to contact with the substrate on which is disposed HPVLP, e.g., a high signal-to-noise HPVLP substrate. In one embodiment, detection is with an enzyme labeled antibody, e.g., an enzyme labeled IgG, such as an HRP (Horseradish Peroxidase) labeled IgG. In another embodiment, the detection reagent, e.g., an HRP labeled IgG, is added at a concentration of at least 0.01 µg/mL, 0.02 µg/mL, 0.03 µg/mL, 0.04 µg/mL, 0.05 µg/mL, 0.06 µg/mL, or 0.08 µg/ml. In one embodiment, the detection reagent is provided at 10× to 100× excess over antibody bound to the substrate. In an embodiment the detection reagent is provided, in an amount that gives equal to or more than 10×, 20×, 50×, 75× or 100×) excess as compared to the antibody bound to the substrate.

In an embodiment the solution-phase HPVLP in (c) is present at 2× to 100× excess particles over anti-JCV antibody in the second reaction mixture or sample. In an embodiment the excess of particles over the anti-JCV antibody in the second reaction mixture or sample is equal to or greater than 2×, 4×, 5×, 10×, 15×, 20×, 40×, 50×, 70×, 80×, 100× or 110×.

In an embodiment, for the second reaction mixture, 20 ngs to 60 ngs, 30 ngs to 50 ngs, 20 ngs to 40 ngs, 35 ngs to 45 ngs of HPVLP are disposed on said substrate. In an embodiment about 20 ngs, 30 ngs, 40 ngs, 50 ngs or 60 ngs of HPVLP are disposed on said substrate. Typically, a multi-substrate device, e.g., a multi-well plate, e.g., a polystyrene multi-well plate, will have an amount of HPVLP specified herein on each of a plurality of substrates. A typical substrate is the interior of a well on a multi-well plate.

In an embodiment, for the second reaction mixture, the sample is contacted with the soluble-phase HPVLP and then unbound anti-JVC antibody is allowed to bind to a HPVLP disposed on a substrate. In an embodiment, for the second reaction mixture, the sample is in simultaneous contact with the soluble-phase HPVLP and HPVLP disposed on a substrate.

In an embodiment the ratio of μl sample (this refers to undiluted sample, or the amount of sample in a dilution, so 100 μl of a 1 μl:100 μl dilution would be 1 μl of sample), e.g., serum or plasma, to ngs of HPVLP disposed on the substrate is: between 1:100 and 1:20; 1:80 and 1:30; 1:60 and 1:20; 1:20 and 1:60; 1:30 and 1:50. In an embodiment the ratio of μl of sample, e.g., serum or plasma, to ngs of HPVLP disposed on the substrate is about: 1:30, 1:40, or 1:50. In an embodiment the ratio of μl of sample, e.g., serum or plasma, to ngs of HPVLP disposed on the substrate is about: (0.08 to 1.2): 30, (0.08 to 1.2): 40, or (0.08 to 1.2): 50.

In one embodiment, the sample, e.g., serum, is diluted, such as by about 100-fold, in, for example, buffer, prior to contact with the substrate on which is disposed HPVLP, e.g., a high signal-to-noise HPVLP substrate. In one embodiment, detection is with an enzyme labeled antibody, e.g., an enzyme labeled IgG, such as an HRP labeled IgG. In another embodiment, the detection reagent, e.g., an HRP labeled IgG, is added at a concentration of at least 0.01 μg/mL, 0.02 μg/mL, 0.03 μg/mL, 0.04 μg/mL, 0.05 μg/mL, 0.06 μg/mL, or 0.08 μg/ml. In one embodiment, the detection reagent is provided at 10× to 100× excess over antibody bound to the substrate. In an embodiment the detection reagent is provided, in an amount that gives equal to or more than 10×, 20×, 50×, 75× or 100×) excess as compared to the antibody bound to the substrate.

In one embodiment, responsive to the level of anti-JCV antibodies detected in step (b), steps (c) and/or (d) are performed.

In one embodiment, responsive to the level of anti-JCV antibodies detected in step (b), e.g., the index level (nOD) is >0.2 and is <0.4, then steps (c) and (d) are performed.

In one embodiment, the sample, e.g., serum or plasma, is diluted, such as by an amount equal to or greater than about 50, 100, or 150 fold, in, e.g., buffer, prior to forming said second reaction mixture. In another embodiment, the sample, e.g., serum or plasma, is diluted, such as by an amount equal to or greater than about 50-fold, 100-fold, or 150-fold, in, e.g., buffer, prior to forming said third reaction mixture. In another embodiment, detection of one or both of the second and third reaction mixture is with an enzyme labeled antibody, e.g., an enzyme labeled IgG, e.g., an HRP labeled IgG.

Detection of one or both of the second and third reaction mixtures can be with an HRP labeled IgG, added at a concentration of at least 0.01, 0.02, 0.03, 0.04, 0.05, 0.06, or 0.08 g/ml. In one embodiment, the detection reagent is provided at 10× to 100× (e.g., 10×, 20×, 50×, 75× or 100×) excess as compared to the antibody bound to the substrate.

In one embodiment evaluating the level of anti-JCV antibody in a sample further includes evaluating a standard, such as a cut off calibrator, having, e.g., an index of about 1 (e.g., a optical density of 1, where a positive control has an optical density of 1.3, and a negative control has an optical density of 0.1) and a signal-to-noise ratio of equal to or greater than 15× to 20× (e.g., equal to or greater than 16×, 17×, 18×, or 19×), in step b. Another embodiment includes evaluating a standard, e.g., a positive control, having, for example, a score of about 1.3, in step b. In other embodiments, the method further includes evaluating a standard, such as a negative control, having, e.g., a score of about 0.1, in step b.

In an embodiment the method includes determining the amount that binding to said soluble phase HPVLP particles inhibits or reduces binding to substrate disposed HPVLP particles as compared with binding to substrate disposed HPVLP particles in said first aliquot. The results of the first step of the two-step assay (steps (a) and (b) above), are typically expressed as a normalized OD (nOD, or "index") value. The results of the second step of the two-step assay (steps (c) and optionally (d) above), are typically expressed as "percent inhibition." In an embodiment the nOD is $OD_{450}$. In an embodiment said inhibition is less than or equal to a predetermined value, e.g., 45%, and said sample is classified as negative.

In an embodiment said inhibition is greater than a predetermined value, e.g., 45% and said sample is classified as positive.

In one embodiment, a cut-off calibrator (CO) is adjusted to have a reactivity index (nOD) of about 1.0, and a positive control (PC) is adjusted to have a reactivity index of about 1.3. The CO and PC solutions are made by mixing a serum positive for JCV antibodies with a serum that is negative for JCV antibodies. For the negative control (NC), which can be, for example, a bottle of anti-JCV antibody-negative sera, the index (nOD) target is about 0.1.

In one embodiment the JCV antigen is a VLP particle, such as a HPVLP that is chromatographically purified prior to use in an assay featured in the invention.

In certain embodiments, the sample is a serum sample, a urine sample, a plasma sample, a blood sample or a cerebrospinal fluid (CSF) sample. In one embodiment the sample is a serum sample diluted 1:101 prior to forming the first reaction mixture comprising a first aliquot of the sample and the substrate on which is disposed HPVLPs.

In another embodiment, the secondary detection reagent (e.g., an anti-human IgG) is conjugated to a detectable agent, such as a peroxidase, such as HRP. In one embodiment, the secondary detection reagent can be anti-human IgG, wherein the anti-human IgG is conjugated to HRP. In another embodiment, the detection reagent solution containing IgG-HRP is used at 0.04 μg/mL. For example, a 0.8 mg/mL stock solution of IgG-HRP is diluted 1:15,000, 1:20,000, 1:30000 or more, prior to use in the assay to detect the level of anti-JCV antibody bound to HPVLP. In another embodiment, the concentration of the secondary detection reagent is adjusted for new lots to match signal to previous lot and the incubation time with the conjugate is only 30 min. In one embodiment, TMB (tetramethylbenzidine) and hydrogen peroxide in buffer are incubated with the reaction mix containing the HRP IgG mixture bound to anti-JCV antibody for 20 minutes, ±2 minutes.

In an embodiment a decrease in the detected level in the secondary assay sample compared to the sample that was not preincubated indicates the sample is positive for anti-JCV antibody, and a change in the detected level below a specified percentage indicates that there is no JCV-specific antibody present in the sample.

In one embodiment, the sample is determined to have an index value (i.e., nOD value) >0.2 and <0.4 (the "indeterminant zone") after the first step of the assay, which is the formation of a first reaction mixture comprising a first aliquot of sample and a substrate on which is disposed HPVLP, e.g., a high signal-to-noise HPVLP substrate, and detecting the level of anti-JCV antibody bound to said substrate on which is disposed HPVLP, e.g., a high signal-to-noise HPVLP substrate. A second aliquot of the sample can then be tested in the second step of the assay, which comprises formation of a second mixture between the second aliquot and a solution-phase HPVLP prior to detecting unbound anti-JCV antibody in the second mixture by contacting the second mixture with a substrate on which is disposed HPVLP, e.g., a high signal-to-noise HPVLP substrate.

In another embodiment, if the sample is determined to have an index value <0.2 after the first step of the assay, then the sample is determined to be anti-JCV antibody negative. In one embodiment, a sample determined to be anti-JCV antibody negative is not evaluated using the second step of the assay.

In another embodiment, if the sample is determined to have an index value >0.4 after the first step of the assay, then the sample is determined to be anti-JCV antibody positive. In one embodiment, a sample determined to be anti-JCV antibody positive is not evaluated using the second step of the assay.

In one embodiment, the invention comprises obtaining a biological sample from a subject (e.g., plasma, serum, blood, urine, or cerebrospinal fluid (CSF)); and correlating the detected level with a reference, such that the reference is selected to indicate a false negative rate not greater than 3% and minimal cross reactivity to other polyoma viruses, e.g., BK virus (BKV). In some embodiments, the reference, derived from a control sample or set of samples, is processed with the sample from the subject. In some embodiments, the reference is selected such that the false negative rate of the assay is not greater than 1%. The assay can be performed such that the HPVLP is disposed on a solid substrate such as a microtiter plate or slide. In some embodiments, the HPVLP consists essentially of VP1 viral protein. The HPVLP can further include other viral proteins, for example at least one of a VP2, or a VP3. The viral protein(s) in the HPVLP can be recombinantly derived (e.g., a MAD1 VP1) or can be a naturally-occurring viral protein (e.g., derived from a naturally-occurring source). The method can be performed using, for example, a biological sample obtained from a subject currently being treated with an immunomodulatory drug, a subject considering initiating treatment with an immunomodulatory drug, or a subject suspected of having Progressive Multifocal Leukoencephalopathy (PML).

In some embodiments, an nOD level of 1.5, 1.4, 1.3, 1.2, 1.1, 1.0, 0.9, 0.8, or 0.7, a sample indicates that a patient is at a lower risk of developing PML, and an nOD level of 0.7, 0.8, 0.9. 1.0, 1.1, 1.2, 1.3, 1.4, or 1.5 a sample indicates that a patient is at a higher risk of developing PML. In some embodiments, the level is an index level of 0.9. In some embodiments, the pre-determined level is an index level of 1.2. In some embodiments, the pre-determined level is an index level of 1.5.

In another aspect, the invention features, a kit containing a substrate on which is disposed HPVLP, e.g., a high signal-to-noise HPVLP substrate. The substrate can include a multiwall plate, such as a 96 well plate. In one embodiment, the kit includes one or more or all of the following: a substrate, such as a plate with wells coated with JCV antigen substrate, e.g., HPVLP; a JCV antigen, e.g., HPVLP, lyophilized or in solution; a JCV cut-off calibrator, an anti-JCV antibody positive control and a JCV negative control, which are samples of sera, such as human sera. In one embodiment, the kit includes, or further includes one of more reagents for detecting a complex containing anti-JCV antibodies bound to antigen, and the reagents include, for example, a JCV conjugate, a casein sample, a detectable reagent, such as TMB (tetramethylbenzidine), a wash buffer, and a stop reagent.

In another aspect, the invention features, a substrate on which is disposed HPVLP, e.g., a high signal-to-noise HPVLP substrate.

In another aspect, the invention features, a kit comprising an HPVLP and at least one reagent for performing an assay to identify an anti-JCV antibody level in a sample, such as a biological sample.

In other aspects, the invention relates to a solution comprising HPVLP particles, consisting essentially of VP1-containing particles that are greater in size than a VP1 pentamer (capsomere), e.g., containing about 5, 10, 20, 30, 40, 50, 60, 70 or 72 pentamers or containing about 360 VP1 molecules.

Another aspect of the invention is a method of preparing a solution of HPVLPs, the method comprising removing VP1-containing particles from the solution that are the size of a VP1 pentamer or less.

The methods disclosed herein are based at least in part on the discovery that anti-JCV antibody titer and other characteristics such as affinity/avidity can be indicators of a patient's risk of developing Progressive Multifocal Leukoencephalopathy (PML).

accordingly, in another aspect, the invention features, a method of evaluating a patient's risk of developing PML, comprising acquiring knowledge of a JC Virus (JCV) antibody titer (e.g., determined as described herein and expressed as normalized optical density (nOD) or index) or affinity/avidity (e.g., as determined as described herein and expressed percent inhibition in the confirmation step of the assay) in a sample of the patient, and optionally comparing the value or values acquired with a reference disclosed herein, to thereby evaluate risk.

In one embodiment, an anti-JCV antibody titer or percent inhibition is determined in a biological sample from a patient, such as a blood (serum or plasma), or CSF sample.

If the titer or/and percent inhibition, or a function of both values is determined to be below a pre-determined level, the patient is determined to be at a lower risk of developing PML, and if the titer and/or percent inhibition, or a function of both values is determined to be at or above the pre-determined level the patient is determined to be at a higher risk of developing PML.

The method can further provide that determining the anti-JCV antibody titer or percent inhibition in a sample of the patient requires removing a biological sample from the patient's body or analyzing a sample from the patient, or that if the patient is determined to be at a lower risk of developing PML, a therapy, such as immunosuppressant therapy is administered to the patient.

In one embodiment, an anti-JCV antibody titer or percent inhibition is determined in more than one biological sample from a patient, such as one or more of a blood (serum or plasma), or CSF sample.

In one embodiment, the subject has multiple sclerosis, e.g., a multiple sclerosis patient that is already receiving therapy with an anti-VLA-4 antibody, e.g., natalizumab.

In one embodiment, the patient is determined to be at a lower risk of developing PML, and the patient is further administered an anti-VLA-4 therapy, such as an anti-VLA-4 antibody, such as natalizumab, or a fragment thereof (such as an antigen-binding fragment thereof).

In one embodiment, the patient is determined to be at a higher risk of developing PML, and the patient is identified as someone who should receive an alternative therapy, e.g., the patient should stop receiving anti-VLA-4 antibody therapy, e.g., natalizumab, and, e.g., receive an alternative therapy, e.g., an alternative approved multiple sclerosis (MS) therapy such as Avonex®. In another embodiment, the patient is determined to be at a higher risk of developing PML, and the patient is administered an anti-VLA-4 antibody therapy, e.g., natalizumab.

In one embodiment, the patient is determined to be at a higher risk of developing PML based upon anti-JCV antibody titer or percent inhibition, and the patient is identified as someone who should receive additional testing to determine risk of developing PML.

In one embodiment, the patient is determined to have a lower risk of PML if, (i) the anti-JCV antibody titer as indicated by index value or nOD is determined to be <0.5, or (ii) the anti-JCV antibody titer as indicated by index value or nOD is determined to be >0.5 and <3.0, and the percent inhibition is determined to be less than or equal to 70% or 60%. The patient is determined to have an intermediate risk of PML if, (i) the anti-JCV antibody titer as indicated by index value or nOD is determined to be >0.5 and <1.5, and the percent inhibition value is determined to be >70%. The patient is determined to have a higher risk of PML if, (i) the anti-JCV antibody titer as indicated by index value or nOD is determined to be >0.5 and the percent inhibition value is determined to be >70%, or (ii) the patient showed an increase in index, nOD or titer by 2-fold from a previous test. The percent inhibition of anti-JCV antibodies can be measured, for example, by: (i) contacting a biological sample from the subject with HPVLPs in a solution under conditions suitable for binding of an anti-JCV antibody in the sample to an HPVLP; (ii) separating the JCV antibodies bound to HPVLP from the solution to create a secondary sample; (iii) contacting the secondary sample with HPVLP under the same conditions as (i); and (iv) detecting the level of anti-JCV antibody binding to HPVLP in the secondary sample.

In one embodiment, the anti-JCV antibody titer is measured by, e.g., (i) contacting the biological sample with HPVLPs under conditions suitable for binding of an anti-JCV antibody in the sample to an HPVLP; (ii) detecting the level of anti-JCV antibody binding in the sample to HPVLPs; and (iii) correlating the detected level with a reference set. The reference set can be selected to indicate a false negative rate not greater than a predetermined amount, such as 3%. In another embodiment, anti-JCV antibody titer is measured by a commercial platform, such as a VIDAS® assay (bioMérieux), or another alternative platform, such as a solution-phase method or a lateral flow method.

In one embodiment, the assay indicates that the biological sample does not contain JCV antibodies, and the assay then further includes: (iv) contacting a portion of the biological sample from the subject with HPVLP in a solution prior to step (i) and where the HPVLP of step (i) is attached to a solid substrate, such as to provide a secondary sample; (v) contacting the secondary sample with HPVLP under the same conditions as (i); (vi) detecting the level of anti-JCV antibody binding to HPVLP in the secondary sample; and (vii) comparing the detected level of anti-JCV antibody in the secondary sample to the level of binding in the biological sample when incubated with the solution without HPVLP. A decrease in the detected level in the sample pre-incubated with HPVLP compared to the solution-incubated sample indicates that the sample is positive for an anti-JCV antibody, and no change in the detected level indicates that anti-JCV antibody is not present above background levels in the sample.

In one embodiment, the assay indicates that the biological sample contains JCV antibodies, and the patient is determined to be at higher risk for PML.

In yet another embodiment, the patient is determined to have a lower risk of PML if, (i) the anti-JCV antibody titer as indicated by index value or nOD is determined to be <0.5, or (ii) the anti-JCV antibody titer as indicated by index value or nOD is determined to be >0.5 and <3.0, and the percent inhibition is determined to be less than or equal to 70%. The patient is determined to have a higher risk of PML if, (i) the anti-JCV antibody titer as indicated by index value or nOD is determined to be >3 and the percent inhibition value is determined to be >70%, or (ii) the patient showed an increase in index, nOD or titer by 2-fold from a previous test.

In one embodiment, only index value (nOD) or only percent inhibition is used to determine risk of PML. For example, in one embodiment, the patient is determined to have a lower risk of PML if the anti-JCV antibody titer as indicated by index value or nOD is determined to be <0.5, the patient is determined to have a higher risk if the anti-JCV antibody titer as indicated by index value or nOD is determined to be >0.5 and <1.5, or the patient is determined to have an even higher risk if the anti-JCV antibody titer as indicated by index value or nOD is determined to be >1.5.

In one embodiment, the assay indicates that the biological sample does not contain JCV antibodies above a background level, and the patient is determined to be at lower risk for PML.

In another aspect, the invention features, a method for evaluating or testing an assay procedure. An anti-JCV antibody assay can be reevaluated for effectiveness at a predetermined interval, such as every 6 months or every year. In one exemplary proficiency assay, a collection of samples, e.g., 30, 40 or 50 serum samples and 30, 40, or 50 plasma samples are provided such as for evaluation by the current optimized method and a preceding earlier-generation method. The concordance between the results is assessed and if the concordance is found to be greater than, e.g., 90% or 95%, the performance of the assay can be determined to be acceptable. In one embodiment, a panel of samples, e.g., containing 90, 100, 150 or more samples, with known anti-JCV antibody status is utilized to assess consistency of assay performance over time. The concordance between the results is assessed and if the concordance is found to be greater than, for example, 90% or 95%, the performance of the assay can be determined to be acceptable. The panel of samples is patient sera available in sufficient volume to create a sample bank.

In one aspect, an entity, e.g., a healthcare provider, acquires information resulting from an anti-JCV antibody assay described herein, and responsive to the information, administers a treatment described herein to the patient, e.g., a MS patient.

In another aspect, a JCV assay described herein is performed on a patient, and then the patient is treated, e.g., the MS patient is treated, based on the results of the assay.

The anti-JCV antibody titer or percent inhibition in a patient can be reevaluated at regular intervals, such as every 3 months, every 6 months, or every 12 months or at longer intervals or more frequently. An observed increase in antibody titer or percent inhibition can indicate an increase in the patient's risk of developing PML. For example, an increase of 2 fold or 3 fold in antibody titer (nOD or index) can indicate an increased risk of PML. A patient receiving an anti-VLA-4 therapy, such as a natalizumab, may stop therapy with the anti-VLA-4 therapy, and optionally begin therapy with an alternative agent, e.g., an immunosuppressant other than an anti-VLA-4 therapy, or other than natalizumab. An increase in titer may present differently in patients having a high baseline titer (e.g., at a more narrow range in range of titer) than in patients having a low baseline titer.

In one embodiment, a patient receiving an anti-VLA-4 antibody, e.g., natalizumab, can be monitored, e.g., every five, six, seven, eight, nine, ten, eleven, twelve, fifteen, twenty, thirty, forty months, for anti-JCV antibody titer and/or percent inhibition.

In one embodiment, a patient is not re-evaluated for the presence of JCV antibodies, or for anti-JCV antibody titer or percent inhibition within one or two or three weeks after having received plasmapheresis. In another embodiment, a patient is not re-evaluated for the presence of JCV antibodies, or for anti-JCV antibody titer or percent inhibition within one or two or three weeks after having received intravenous immunoglobulin (IVIG) treatment.

The measure of anti-JCV antibody titer can be in terms of nOD or an index value.

Evaluation of a patient as described herein can be conducted prior to administration of an anti-VLA-4 therapy, or after the patient has begun an anti-VLA-4 therapy.

In one embodiment, a patient is determined to be at a lower risk of PML, such as by an assay described herein, and the patient is administered an anti-VLA-4 therapy. In another embodiment, the patient is determined to be at a higher risk of PML and the patient is administered an anti-VLA-4 therapy, e.g., an anti-VLA-4 antibody, such as natalizumab. In yet another embodiment, the patient is determined to be at a higher risk of PML and the patient is administered a therapy other than an anti-VLA-4 therapy, such as an interferon, glatiramer acetate or a corticosteroid.

In one embodiment, the patient is determined to have an increased risk for PML, and the patient accordingly stops receiving an anti-VLA-4 therapy.

The patient can be monitored at regular intervals, e.g., every 3 months, every 6 months, every year, or more or less frequently, for a decrease in anti-JCV antibody titer or a decrease in percent inhibition of JCV antibodies. A decrease in anti-JCV antibody titer or a decrease in percent inhibition of JCV antibodies can indicate that the patient has a lowered risk of developing PML.

In one embodiment, the anti-JCV antibody titer or percent inhibition of JCV antibodies is determined to be decreased below a pre-determined level, even after having been elevated, then the patient can be administered, or determined to be a candidate to receive treatment with, an anti-VLA-4 therapy. If the patient previously received an anti-VLA-4, then the patient's anti-VLA-4 therapy can reinstated. After reinstating the anti-VLA-4 therapy, the patient can be evaluated every 6 months or every year for a decrease in antibody titer or a decrease in percent inhibition of JCV antibodies.

In one embodiment, after a patient is determined to be at a higher risk of PML, e.g., the patient is determined to have an anti-JCV antibody titer as measured by nOD of >0.5, e.g., >1.0 or >1.5, then the patient is not tested for JCV status again. For example, the patient can stop therapy with an anti-VLA-4 therapy such as natalizumab, and not be tested again for anti-JCV antibody status.

In one embodiment, a method of evaluating a patient as described herein, such as to determine an anti-JCV antibody titer or percent inhibition, can further include assessing other measures of risk predictors. For example, a method of evaluating a patient can further include: (a) determining if the patient has received extended treatment with an anti-VLA-4 therapy (e.g., longer than 24 months); or (b) determining if the patient has received a specified non-anti-VLA-4 immunosuppressant therapy (e.g., mitoxantrone or other therapies in the last 2, 3, 5 years or ever in the patient's life). The relative risk of PML for a patient who has an anti-JCV antibody titer or percent inhibition above a pre-determined level but has no specified prior immunosuppressant use and has not had an extended treatment with an anti-VLA-4 therapy is less than the relative risk of a patient who has an anti-JCV antibody titer or percent inhibition below a pre-determined level and has specified prior immunosuppressant use or an extended treatment with an anti-VLA-4 therapy, which is less than the relative risk of a patient who has an anti-JCV antibody titer or percent inhibition above a pre-determined level and has specified prior immunosuppressant use and extended treatment with an anti-VLA-4 therapy.

In one embodiment, the patient previously received an anti-VLA-4 therapy, e.g., natalizumab, and in another embodiment, the patient is administered an anti-VLA-4 therapy, based on an evaluation, e.g., an evaluation of anti-JCV antibody titer or percent inhibition. For example, as a result of the evaluation, the patient can be classified as a candidate for anti-VLA-4 therapy. In one embodiment, a patient classified as a candidate for anti-VLA-4 therapy is further administered the therapy.

In some embodiment, factors to be included in the stratification model are the patient's age or gender.

Method described herein can incorporate one or more factors into the evaluation of the patient. Accordingly, in another aspect, the invention features, a method of evaluating a patient, e.g., as a candidate to receive treatment with an anti-VLA-4 therapy.

The method includes, for example, acquiring or determining a JC Virus (JCV) antibody titer and percent inhibition in a biological sample from the patient, e.g., by a method described herein. If the antibody titer or percent inhibition is determined to be below a pre-determined level, then the patient can be classified as being suitable for treatment with a first category of therapy, such as an anti-VLA-4 therapy, e.g., natalizumab. If the antibody titer or percent inhibition is determined to be at or above the pre-determined level the patient is classified as being suitable for a second category of therapy, e.g., interferon, glatiramer acetate or a corticosteroid. Acquiring an anti-JCV antibody titer and percent inhibition in a sample of a patient may include removing a biological sample from the patient's body or analyzing a sample from the patient. The method of evaluation may also include administering a therapy, such as from the first category (e.g., natalizumab) or the second category (e.g., interferon, glatiramer acetate or a corticosteroid), to the patient.

In yet another embodiment, the patient is determined to have a lower risk of PML if, (i) the anti-JCV antibody titer as indicated by index value or nOD is determined to be <0.5, or (ii) the anti-JCV antibody titer as indicated by index value or nOD is determined to be >0.5 and <3.0, and the percent inhibition is determined to be less than or equal to 70%. The patient is determined to have a higher risk of PML if, (i) the anti-JCV antibody titer as indicated by index value or nOD is determined to be >1.5 and the percent inhibition value is determined to be >70%, or (ii) the patient showed an increase in index, nOD or titer by 2-fold from a previous test. The patient is determined to have an intermediate risk of PML if the anti-JCV antibody titer as indicated by index value or nOD is determined to be >0.5 and <1.5, and the percent inhibition value is determined to be >70%.

As discussed above, methods of evaluating a patient can incorporate more than one consideration or factor. Thus, methods of evaluating a patient can further include:

(aa) determining if the patient has received extended treatment with an anti-VLA-4 therapy (e.g., longer than 24 months) and in embodiments providing a prior anti-VLA-4 therapy exposure classification; or (bb) determining if the patient has received a specified non-anti-VLA-4 immunosuppressant therapy (e.g., in the last 2, 3, 5 years or ever in the patient's life), and in embodiments providing a prior immunosuppressive exposure classification.

Typically, a patient who has an anti-JCV antibody titer or percent inhibition above a pre-determined level but has no specified prior immunosuppressant use and has not had an extended treatment with an anti-VLA-4 therapy is classified as having less risk of developing PML than the relative risk of a patient who has an anti-JCV antibody titer or percent inhibition below a pre-determined level and has specified prior immunosuppressant use or an extended treatment with an anti-VLA-4 therapy, which is less than the relative risk of a patient who has an anti-JCV antibody titer or a percent inhibition above a pre-determined level and has specified prior immunosuppressant use and extended treatment with an anti-VLA-4 therapy.

In one embodiment, the patient has previously received an anti-VLA-4 therapy. In another embodiment, the method includes administering an anti-VLA-4 therapy, e.g., natalizumab to the patient.

In one embodiment, the patient is classified as a candidate for anti-VLA-4 therapy, and the patient is further administered the anti-VLA-4 therapy.

Patients who have received an anti-VLA-4 therapy, such as natalizumab for 24 months or less, who have not previously received an immunosuppressant therapy (other than anti-VLA-4 therapy), and who test negative for exposure to JCV (e.g., negative for JCV antibodies) typically have the lowest risk for developing PML. Conversely, patients who received anti-VLA-4 therapy for longer than 24 months, who have previously received an immunosuppressant therapy (other than an anti-VLA-4 therapy), and who test positive for exposure to JCV (e.g., positive for JCV antibodies) typically have the highest risk for developing PML.

A patient's risk level for PML can be assessed by evaluating one, or any two or all three of the identified risk factors. For example, a patient, e.g., a patient with multiple sclerosis (MS) who tests negative for anti-JCV antibody titer can be determined to be at a lower risk for PML. A patient at a lower risk for PML can have a risk of less than about 0.2/1000 patients, e.g., ≤0.11/1000.

In an embodiment, a patient, e.g., a patient with MS, who has received an anti-VLA-4 therapy, such as natalizumab, for 24 months or less (e.g., for 23 months, 22 months, 20 months, 15 months, 12 months, 6 months, 1 month or less), and who has not previously received an immunosuppressant therapy can be determined to be at a lower risk for PML. For example, the patient can be determined to have a risk of PML of about 0.54/1000 patients. The patient can accordingly be determined to be a candidate to receive further treatment with an anti-VLA-4 therapy, such as natalizumab.

In an embodiment, a patient who has received an anti-VLA-4 therapy, such as natalizumab, for longer than 24 months, such as for about 25 to 48 months or more (e.g., 26, 28, 30, 36, 40, or 48 months or more), and who has not previously received an immunosuppressant therapy can be determined to be at, or classified as having, a higher risk for PML. A patient at a higher risk of PML can have a risk of ≥ about 3.7/1000 patients, e.g., about 1.37/1000 patients. The patient can accordingly be determined to be a candidate to receive further treatment with an anti-VLA-4 therapy, such as natalizumab.

In an embodiment, a patient who has received an anti-VLA-4 therapy, such as natalizumab, for 24 months or less (e.g., for 24 months, 22 months, 20 months, 15 months, 12 months, 6 months, 1 month or less), and who is determined to be negative for anti-JCV antibodies, or JCV nucleic acid, can be determined to be at, or classified as having, a lower risk for PML. For example, the patient can be determined to be at a risk of ≤0.2/1000 patients. The patient can accordingly be determined to be a candidate to receive further treatment with an anti-VLA-4 therapy, such as natalizumab.

In an embodiment, a patient who has not received prior treatment with an immunosuppressant (other than an anti-VLA-4 therapy), and who is determined to be negative for JCV, is determined to be at a lower risk for PML, e.g., ≤0.2/1000 patients. The patient can accordingly be determined to be a candidate to receive further treatment with an anti-VLA-4 therapy, such as natalizumab.

In an embodiment, a patient who has received an anti-VLA-4 therapy, such as natalizumab, for longer than 24 months (e.g., for 25 months, 26 months, 28 months, 30 months, 35 months, 38 months, 40 months, 48 months or longer), and who has previously received an immunosuppressant therapy other than an anti-VLA-4 therapy can be determined to be at a higher risk for PML. A patient at a higher risk for PML can have a risk of about 0.37/1000 or greater, e.g., about 4.3/1000 patients. The patient can accordingly be determined not to be a candidate to receive further treatment with an anti-VLA-4 therapy, such as natalizumab, or can be determined to be a candidate to receive treatment with an anti-VLA-4 therapy accompanied by more frequent monitoring. For example, a patient at higher risk for PML who receives therapy with an anti-VLA-4therapy can receive more frequent monitoring for development of PML, then a patient at lower risk of PML.

In an embodiment, a patient who has received an anti-VLA-4 therapy, such as natalizumab, for 24 months or less (e.g., for 24 months, 22 months, 20 months, 15 months, 12 months, 6 months, 1 month or less), and who has previously received an immunosuppressant therapy other than an anti-VLA-4 therapy can be determined to be at a higher risk for PML. For example, the patient can be determined to have a risk of PML of 0.66/1000 patients. The patient can accordingly be determined not to be a candidate to receive further treatment with an anti-VLA-4 therapy, such as natalizumab, or can be determined to be a candidate to receive treatment with an anti-VLA-4 therapy accompanied by more frequent monitoring. For example, a patient at higher risk for PML who receives therapy with an anti-VLA-4 therapy can receive more frequent monitoring for development of PML, then a patient at lower risk of PML.

In an embodiment, a patient who has received an anti-VLA-4 therapy, such as natalizumab, for longer than 24 months (e.g., for 25 to 48 months, such as 26, 30, 36, 42 or 48 months or longer), and who is determined to be positive for JCV, is determined to be at a higher risk for PML. The patient can accordingly be determined not to be a candidate to receive further treatment with an anti-VLA-4 therapy, or can be determined to be a candidate to receive treatment with an anti-VLA-4 therapy accompanied by more frequent monitoring.

In an embodiment, a patient who has received an anti-VLA-4 therapy, such as natalizumab, for longer than 24 months (e.g., for 25 to 48 months, such as 26, 30, 36, 42 or 48 months or longer), and who has not received prior treatment with an immunosuppressant (other than an anti-VLA-4 therapy), and who is determined to be positive for JCV, and is determined to be at a higher risk for PML. For example, the patient can be determined to have a risk of PML of 4/1000 patients. The patient can accordingly be determined not to be a candidate to receive further treatment with an anti-VLA-4 therapy, or can be determined to be a candidate to receive treatment with an anti-VLA-4 therapy accompanied by more frequent monitoring.

In an embodiment, a patient, e.g., an MS patient, who has received prior treatment with an immunosuppressant other than an anti-VLA-4 therapy, and who is determined to be positive for anti-JCV antibodies, or JCV nucleic acid, can be determined to be at a higher risk for PML. The patient can accordingly be determined not to be a candidate to received further treatment with an anti-VLA-4 therapy, or can be determined to be a candidate to receive treatment with an anti-VLA-4 therapy accompanied by more frequent monitoring.

In an embodiment, a patient who has received prior treatment with an immunosuppressant other than an anti-VLA-4 therapy, and who is determined to be positive for anti-JCV antibodies, or JCV nucleic acid, and who has received an anti-VLA-4 therapy, such as natalizumab, for longer than 24 months (e.g., for 25 to 48 months, such as 26, 30, 36, 42 or 48 months or longer) can be determined to be at a higher risk for PML. For example, the patient can be determined to have a risk of 9.8/1000 patients. The patient can accordingly be determined not to be a candidate to received further treatment with an anti-VLA-4 therapy, or can be determined to be a candidate to receive treatment with an anti-VLA-4 therapy accompanied by more frequent monitoring.

In an embodiment, a patient who has received an anti-VLA-4 therapy, such as natalizumab, for 24 months or less (e.g., for 24 months, 22 months, 20 months, 15 months, 12 months, 6 months, 1 month or less), and who has received prior treatment with an immunosuppressant other than an anti-VLA-4 therapy, and who is determined to be positive for JCV, can be determined to be at a higher risk for PML. For example, the patient can be determined to have a risk of PML of 4.5/1000 patients. The patient can accordingly be determined not to be a candidate to receive further treatment with an anti-VLA-4 therapy, or can be determined to be a candidate to receive treatment with an anti-VLA-4 therapy accompanied by more frequent monitoring.

In an embodiment, a patient who has received an anti-VLA-4 therapy, such as natalizumab, for 24 months or less (e.g., for 24 months, 22 months, 20 months, 15 months, 12 months, 6 months, 1 month or less), and who has not received prior treatment with an immunosuppressant (other than an anti-VLA-4 therapy), and who is determined to be positive for JCV, can be determined to be at a higher risk for PML. For example, the patient can be determined to have a risk of PML of 0.35/1000 patients. The patient can accordingly be determined not to be a candidate to receive further treatment with an anti-VLA-4 therapy, or can be determined to be a candidate to receive treatment with an anti-VLA-4 therapy accompanied by more frequent monitoring.

A patient determined to have a lower risk of developing PML can be determined to have a risk of ≤ about 0.54/1000 patients, e.g., ≤0.25/1000, ≤0.2/1000, 0.19/1000, ≤0.15/1000, ≤0.11/1000, ≤0.1/1000, e.g., 0.3/1000, 0.25/1000, 0.2/1000, 0.19/1000, 0.15/1000, 0.11/1000, or 0.1/1000 or lower. A patient determined to have a higher risk of PML can be determined to have a risk of about 0.54/1000 or greater, e.g., about 0.55/1000, about 0.60/1000, about 0.66/1000, about 1.2/1000, about 1.37/1000, about 2.0/1000, about 2.5/1000, about 3.0/1000, about 4.3/1000, about 5.0/1000, about 7.8/1000, about 8.0/1000, or higher. For example, a patient determined to have a higher risk of PML can be determined to have a risk of 0.3/1000, 0.35/1000, 0.5/1000, 0.66/1000, 1.2/1000, 1.37/1000, 2.0/1000, 2.5/1000, 3.0/1000, 4.3/1000, 5.0/1000, 7.8/1000, 8.0/1000 or higher.

In one embodiment, a patient who has received prior treatment with an anti-VLA-4 therapy for longer than 24 months, and who has not received prior therapy with an immunosuppressant other than anti-VLA-4 therapy, and who is determined to be JCV negative, is determined to be at lower risk of developing PML, and therefore a suitable candidate to receive further treatment with an anti-VLA-4 therapy, such as natalizumab. However, due to having received anti-VLA-4 therapy for longer than 24 months, the risk assessment can include a recommendation to monitor the patient more frequently for the development of adverse symptoms, such as symptoms that may indicate the development of PML.

Enhanced monitoring of patients for the development of PML can include increased frequency of tests to identify the presence of JCV, e.g., increased testing by anti-JCV antibody assays or nucleic acid-based assays. Enhanced monitoring can also include MRI scans to identify brain lesions due to PML.

In one embodiment, a patient who has anti-JCV antibodies at less than a preselected criterion has an undetectable level of anti-JCV antibodies.

In one embodiment, the patient has previously received an anti-VLA-4 therapy, and in another embodiment, the patient has not previously received an anti-VLA-4 therapy.

In yet another embodiment, the patient is classified as a candidate for anti-VLA-4 therapy, and an anti-VLA-4 therapy, e.g., natalizumab, is administered to the patient.

In one embodiment, making a determination, e.g., determining if the patient is negative for JCV, requires providing (e.g., obtaining or receiving) a biological sample from the patient, and performing an immunoassay, such as an ELISA assay to detect JCV antibodies in the sample. In another embodiment, a determination, e.g., determining if the patient is negative for JCV requires providing a biological sample from the patient and performing an assay, such as a PCR-based assay, to detect JCV nucleic acid in the sample.

If the patient is classified as a candidate for anti-VLA-4 therapy, the patient can be further administered an anti-VLA-4 therapy. A patient classified as a candidate for anti-VLA-4 therapy is determined to have a lower risk for developing PML, e.g., a risk of less than about 0.2/1000 patients, e.g., 0.3/1000 patients, or 0.2/1000 patients or 0.19/1000 patients or 0.11/1000 patients. For example, a patient having a lower risk of PML can have a risk of ≤0.2/1000.

A patient not classified as a candidate for anti-VLA-4 therapy, or determined to be a candidate for anti-VLA-4 therapy with enhanced monitoring for development of PML, is determined to have a higher risk for developing PML, e.g., a risk of greater than or equal to about 0.3.7/1000 patients. For example, a patient determined to have a higher risk of PML can have a risk of 0.37/1000, 0.35/1000, 0.66/1000, 1.2/1000, 1.37/1000, 2.5/1000, 4.3/1000, or 7.8/1000 patients.

In an embodiment, a prior immunosuppressant exposure classification, if selected, is one of the following:
 a positive prior immunosuppressant exposure classification that corresponds to having received a non-anti- VLA-4 immunosuppressant therapy within a preselected time period, e.g., within 1, 3, or 5 years, or in the patient's lifetime; and a negative prior immunosuppressant exposure classification that corresponds to being free of a non-anti-VLA-4 immunosuppressant therapy for a preselected time period, e.g., within 1, 3, or 5 years, or in the patient's lifetime.

In an embodiment, a prior VLA-4 therapy exposure classification, if selected, is one of the following:

a positive prior VLA-4 therapy exposure classification that corresponds to having received an anti-VLA-4 therapy for more than a preselected period of time, e.g., as much or more than 1, 2, 3, or 5 years; and a negative prior VLA-4 therapy exposure classification that corresponds to having received an anti-VLA-4 therapy for less than a preselected period of time, e.g., less than 6 months, 1, 2, 3, or 5 years In an embodiment, the method comprises providing a treatment suitability classification, which, e.g., can be selected from one of:

a positive treatment suitability classification that is correlated with suitability of the patient for anti-VLA-4 treatment (the positive treatment suitability classification can be further subdivided into positive treatment suitability classifications that are accompanied by various warnings or requirements for monitoring, such as increased monitoring for development of PML); and a negative treatment suitability classification that is correlated with unsuitability of the patient for anti-VLA-4 treatment, or suitability of the patient for anti-VLA-4 treatment, accompanied by various warnings or requirements for increased monitoring, such for development of PML.

A positive treatment suitability classification correlates with a lower risk of developing PML, and a negative treatment suitability classification correlates with a higher risk of developing PML. A lower risk of developing PML typically corresponds to a risk less than 0.2/1000 patients, and a higher risk of developing PML corresponds to a risk of ≥0.37/1000.

If the patient is assigned a low exposure classification, and a negative JCV status classification, the patient is assigned a positive treatment suitability classification, e.g., a modified positive treatment suitability classification that advises or requires monitoring for development of PML.

If the patient is assigned a negative prior immunosuppressant exposure classification, and a negative anti-JCV antibody status classification, the patient can be assigned a positive treatment suitability classification, e.g., a modified positive treatment suitability classification that advises or requires monitoring for development of PML.

If the patient is assigned a low exposure classification, a negative prior immunosuppressant exposure classification, and a negative JCV antibody classification, the patient is assigned a positive treatment suitability classification.

In one embodiment, the patient is assigned a positive treatment suitability classification, and the patient is further administered an anti-VLA-4 therapy, e.g., natalizumab.

In one aspect, a method of evaluating a patient, e.g., evaluating a patient's risk of developing PML, is also provided. The method includes:

(aaa) determining if the patient is negative or positive for JCV, such as by determining whether the level of anti-JCV antibodies is less than or greater than a preselected criterion, e.g., as determined by a method disclosed herein;

(bbb) determining if the patient has received an anti-VLA-4 therapy for greater than a preselected period of time (e.g., longer than 24 months), or less than a preselected period of time, e.g., 24 months or less, or has not received anti-VLA-4 therapy in a preselected period, e.g., in the last 2, 3, 5 years, or ever in the patient's life;

(ccc) determining if the patient has been free of a non-anti-VLA-4 immunosuppressant therapy for a preselected period of time or has received a non-anti-VLA-4 immunosuppressant therapy for a preselected period of time (a specified time) (e.g., the last 1, 2, 3, 4, 5, or 10 years, or ever in the patient's life); and responsive to the determinations, evaluating the patient.

In an embodiment, the method includes, responsive to a determination that the patient is negative for JCV, determining that a patient is at a lower risk of developing PML.

In an embodiment, the method includes, responsive to a determination that the patient is positive for JCV, determining that the patient has a higher risk of PML.

In an embodiment a determination, e.g., determining that the patient is negative for JCV, comprises or requires removing a sample from the patient's body or analyzing a sample from the patient, or the method further requires administering a therapy to the patient. The therapy can, e.g., in the case of a lower risk patient, be an anti-VLA-4 therapy (e.g., anti-VLA-4 antibody), or, e.g., in the case of a lower risk patient, an alternative (non-anti-VLA-4) therapy, e.g., an interferon, glatiramer acetate or a corticosteroid.

In one aspect, a method of complying with instructions is provided. The instructions may, for example, appear on a government required package insert, e.g., an FDA (Food and Drug Administration) or EMA (European Medicines Agency) mandated package, and provide guidance for the use of an anti-VLA-4 therapy. The method of complying with instructions includes, optionally receiving the instructions; acquiring the results of an evaluative method described herein, and responsive to the acquired result, providing a recommendation for therapy to a patient, and optionally, further administering a therapy to the patient. The instruction can specify an evaluative method as described herein is essential for safely administering the therapy. The therapy may be an anti-VLA-4 therapy, e.g., natalizumab.

A method of evaluating a patient is provided, where the method requires providing a kit for the collection or transport of a patient sample to a healthcare provider; receiving a patient sample from the healthcare provider; performing a method as claimed herein.

A method of treating a patient is also provided. The method requires acquiring the result of a patient or sample evaluation method described herein, and responsive to the acquired result, administering a therapy to the patient. The therapy can be an anti-VLA-4 therapy, such as natalizumab. E.g., For example, responsive to the results of steps (a) and (b), steps (a), (b), and (c), steps (a), (b), (c) and (d), step (c), or steps (c) and (d) administering a therapy, e.g., a therapy described herein, to the patient.

A computerized method of authorizing reimbursement, such as for the cost of an anti-VLA-4 therapy, is also provided. The party to be reimbursed may be a third party payor, such as an insurance company or governmental agency. The method can include (a) acquiring the result of a patient evaluation method described herein, and recording the result on a computer readable medium; (b) acquiring evidence of administration of an anti-VLA-4 therapy to the patient and recording the evidence on a computer readable medium; and (c) if the result is consistent with administration of the anti-VLA-4 therapy, authorizing reimbursement to, or reimbursing, the party.

In one aspect, a method is provided for selecting or classifying a patient as a candidate to receive treatment with an anti-VLA-4 therapy, e.g., natalizumab. For example, the method can include determining that a patient has previously received an anti-VLA-4 therapy for 24 months or less, e.g., for 1 to 24 months, 2 to 20 months, 5 to 15 months, or 10 to 12 months, or that a patient has not previously received treatment with an immunosuppressant, and assessing anti-JCV antibody titers or percent inhibition. In one embodiment, assessing involves analyzing a sample from the patient. The sample can be, for example, a sample of blood, plasma, serum, urine, or cerebrospinal fluid. If the assessment indicates that the patient is positive for JCV, e.g., positive for anti-JCV antibodies or JCV nucleic acid, then the patient is not selected or classified as a candidate for treatment with the anti-VLA-4 therapy. If the assessment indicates that the patient is negative for JCV, e.g., negative for anti-JCV antibodies or JCV nucleic acid, then the patient is selecting or classified as a candidate to receive treatment with the anti-VLA-4 therapy.

An assay for the presence of anti-JCV antibodies can be an immunoassay, such as an ELISA assay. An assay for JCV nucleic acid can be, e.g., a PCR assay or a Next Generation Sequencing (NGS) method.

A patient determined to be at lower risk for PML can further be administered an anti-VLA-4 therapy, such as natalizumab. A patient determined to be at higher risk for PML can further be administered an alternative to an anti-VLA-4 therapy, such as an interferon, glatiramer acetate, a corticosteroid or a TNF agonist. In one embodiment, a patient determined to be at higher risk for PML can be further administered an anti-VLA-4 therapy, and can be required to receive an increased frequency of testing for PML, and where the patient is initially determined to be JCV negative, can also be required to received an increased frequency of testing for JCV.

In one aspect, a method of determining a patient's risk for PML is provided. The method includes (a) determining that a patient has previously received an anti-VLA-4 therapy (e.g., natalizumab) for 24 months or less, or that a patient has not previously received treatment with an immunosuppressant; and (b) assessing a patient's anti-JCV antibody status, where the assessing step includes analyzing a sample from the patient. If the assessment indicates that the patient is JCV negative, then the patient is determined to be at lower risk for PML. If the assessment indicates that the patient is JCV positive, then the patient is determined to be at higher risk for PML.

In another aspect, a method of treating a patient is provided. The treatment method includes, e.g., determining the patient's prior exposure to an anti-VLA-4 therapy, and determining whether the patient previously received treatment with an immunosuppressant. Optionally, the patient's status for JCV can also be determined.

If the patient is determined to have received the anti-VLA-4 therapy for 24 months or less, and not to have previously received treatment with an immunosuppressant, then the patient is determined to be at lower risk for PML, and the patient is administered the anti-VLA-4 therapy. If the patient is determined to have received natalizumab for longer than 24 months (e.g., 25 months or longer), and not to have previously received treatment with an immunosuppressant, then the patient is determined to be at higher risk for PML, and the patient is administered an alternative to anti-VLA-4 therapy, e.g., an interferon, a corticosteroid, a statin or a TNF antagonist.

Determining the patient's prior exposure to an anti-VLA-4 therapy or an immunosuppressant can include asking the patient or a caregiver, e.g., a physician, nurse, parent or other caregiver. In some cases, determining the patient's prior exposure can include accessing the information in a database, e.g., a database of medical records.

Also provided is a method of determining a patient's risk for PML. The method includes determining the patient's previous exposure to an anti-VLA-4 therapy, and determining whether the patient previously received treatment with an immunosuppressant. Optionally, the patient's anti-JCV antibody status may also be determined. If the patient is determined to have received an anti-VLA-4 therapy for 24 months or less, and not to have previously received treatment with an immunosuppressant, then the patient is determined to be at lower risk for PML. If the patient is determined to have received anti-VLA-4 therapy for longer than 24 months, and not to have previously received treatment with an immunosuppressant, then the patient is determined to be at higher risk for PML. A patient determined to be at lower risk for PML may further be administered an anti-VLA-4 therapy, e.g., natalizumab. Conversely, a patient determined to be at higher risk for PML may further be administered an alternative to anti-VLA-4 therapy, e.g., an interferon, a corticosteroid, a statin or a TNF antagonist.

In one embodiment, the patient's JCV status is also determined, and if the patient is determined to be JCV negative, then the patient is determined to be at a lower risk for PML than if the patient was determined to be JCV positive.

Unless otherwise defined, all technical and scientific terms used herein have the same meaning as commonly understood by one of ordinary skill in the art to which this invention belongs. Although methods and materials similar or equivalent to those described herein can be used in the practice or testing of the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DETAILED DESCRIPTION

Figure 1A:
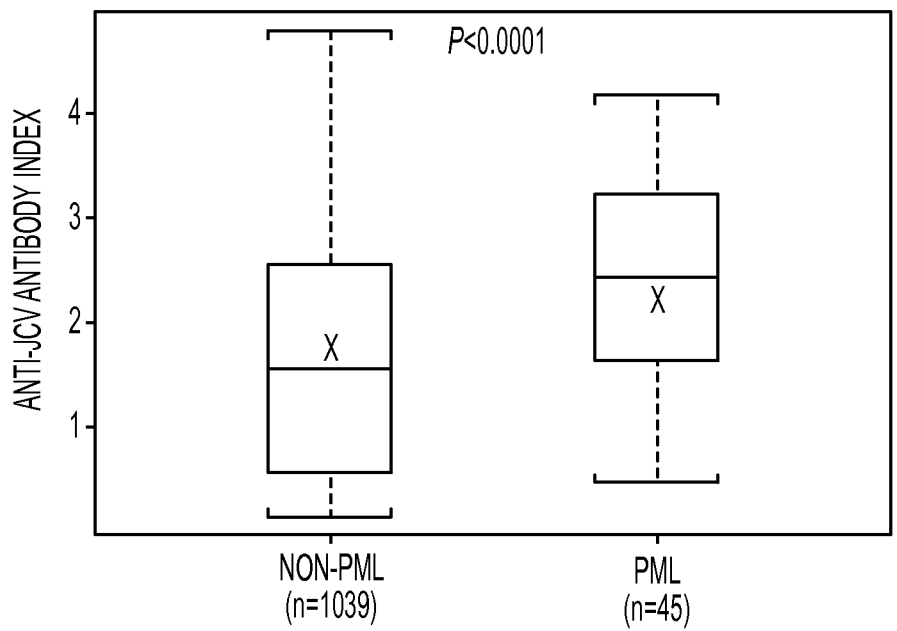
FIGS. 1A and 1B are graphs depicting anti-JCV antibody index in non-PML and PML patients for (A) test data set and (B) validation data set. Lowest index value used for both non-PML patients who tested anti-JCV positive and PML patients with samples available at least 6 months prior to PML diagnosis. In the validation data set, optical densities above 3.0 that were used to calculate anti-JCV antibody index were reported as 3.0 by the testing laboratory. Box represents interquartile range, gray horizontal line=median, horizontal bars=range, x=mean.

The invention is based, at least in part, on the discovery of new and improved methods of assessing the risk of a patient for PML that include assessing anti-JCV antibody titers or percent inhibition. The invention is based at least in part on the discovery that anti-JCV antibody titer and percent antibody inhibition can be an indicator of a patient's risk of developing Progressive Multifocal Leukoencephalopathy (PML).

Applicants have also discovered that in patients who have not received prior immunosupressant (IS) therapy, anti-JCV titer alone can be an indicator of a patient's risk of developing PML. For example, as described in the Example, for anti-JCV antibody positive patients with no prior IS use and an anti-JCV antibody index in the range between 0.9 and 1.5, the risk of PML was lower compared with the total population of anti-JCV antibody positive patients with no prior IS use.

Applicants have also discovered that, in longitudinal studies, pre-PML samples demonstrated consistently positive anti-JCV status and a high anti-JCV index over time. For example, as described in the Example, ninety-six percent of natalizumab-treated MS patients who developed PML had all pre-PML samples with an anti-JCV index above 0.9.

Anti-JCV antibody titer levels may be determined by any available methods. For example, Applicants have developed an optimized assay for determining anti-JCV antibody titer levels in a biological sample, and a method for assaying the antibodies qualitatively by determining percent inhibition values, and using this information to determine the risk of a patient for developing PML (as disclosed in WO2012/166971, the contents of which is incorporated herein by reference in its entirety). The assay includes: (a) forming a first reaction mixture comprising a first aliquot of a sample and a substrate on which is disposed HPVLPs, where, the VLP particles are present at an amount of 0.04 µg, and a concentration of 0.4 µg/mL; b) detecting the level of anti-JCV antibody bound to HPVLP disposed on the substrate, such as by detecting a labeled secondary detection reagent, e.g., an enzyme labeled anti-IgG antibody, bound to anti-JCV antibody bound to said substrate; (c) forming a second reaction mixture comprising a second aliquot of sample with solution-phase HPVLP provided at a concentration of, e.g., 0.4 µg/mL, and a second aliquot of sample provided at, e.g., a 1:100 or 1:101, dilution; (d) forming a third reaction mixture comprising a negative control solution containing no HPVLP, and a third aliquot of sample diluted, e.g., 1:100 or 1:101, or 1:110 in the negative control solution; (e) detecting the level of unbound anti-JCV antibody in the second and third reaction mixtures, such as by detecting JCV capable of binding a substrate on which is disposed HPVLPs, where said HPVLP is present; (f) providing a first value, which corresponds to the level of anti-JCV antibody binding to HPVLP disposed on substrate in the first aliquot of sample, and a second value, which corresponds to the level of unbound anti-JCV antibody in the second reaction mixture, e.g., the level anti-JCV antibody that binds to HPVLP disposed on a substrate from said second reaction mixture; and (g) optionally, comparing the first and second antibody levels.

Applicants have also discovered that a patient has a lower risk of developing PML if, (i) the anti-JCV antibody titer as indicated by index value or nOD is determined to be <0.5, or (ii) the anti-JCV antibody titer as indicated by index value or nOD is determined to be >0.5 and <3.0, and the percent inhibition is determined to be less than or equal to 70%. The patient has a higher risk of PML if, (i) the anti-JCV antibody titer as indicated by index value or nOD is determined to be >3 and the percent inhibition value is determined to be >70%, or (ii) the patient showed an increase in index, nOD or titer by 2-fold from a previous test. In some embodiments, a patient is at lower risk if, (i) the patient has received no prior IS treatment, and (ii) the patient showed an index of 1.5 or less, 1.4 or less, 1.3 or less, 1.2 or less, 1.1 or less, 1.0 or less, 0.9 or less, 0.8 or less, 0.7 or less, or 0.6 or less. In some embodiments, a patient is at lower risk if, (i) the patient has received no prior IS treatment, and (ii) the patient showed an index of less than 0.9.

A patient can be monitored at regular intervals, such as every 1 month, 2 months, 3 months, 4 months, 5 months, 6 months, 7 months, 8 months, 9 months, 10 months, 11 months, every 12 months, or more for a change in anti-JCV antibody titer or percent inhibition. A patient can be monitored over a period of time, such as over a period of 6 months, 7 months, 8 months, 9 months, 10 months, 11 months, 12 months, 13 months, 14 months, 15 months, 16 months, 17 months, 18 months, 19 months, 20 months, 21 months, 22 months, 23 months, 24 months, or more. If the results of a later assay indicate that the patient still has an anti-JCV antibody titer of nOD less than 0.5, and optionally a percent inhibition of <70%, then the patient can be determined to still be at a lower risk for developing PML. If a later assay indicates that the patient's antibody titer is increased by 2 to 3 fold from the initial assay, then the patient can be determined to be at increased or higher risk for developing PML. Applicants observed patients diagnosed with PML tend to demonstrate an increase in antibody titer and nOD by 2 to 3 fold in the six months prior to diagnosis. Furthermore, Applicants observed that patients who have more than one anti-JCV antibody positive sample over time, but the antibody index is consistently below threshold, can be determined to be at lower risk for developing PML. In some embodiments, a patient is at lower risk if the patient is consistently negative for anti-JCV antibodies over a period of time. In some embodiments, a patient is at lower risk if the patient has more than one sample taken over a period of time that is positive for anti-JCV antibodies, where the index level is 1.5 or less. In some embodiments, a patient is at lower risk if the patient has more than one sample taken over a period of time that is positive for anti-JCV antibodies, where the index level is 1.2 or less. In some embodiments, a patient is at lower risk if the patient has more than one sample taken over a period of time that is positive for anti-JCV antibodies, where the index level is 0.9 or less.

A patient has a higher risk of PML if, (i) the anti-JCV antibody titer as indicated by index value or nOD is determined to be >3 and the percent inhibition value is determined to be >70%, or (ii) the patient showed an increase in index, nOD or titer by 2-fold from a previous test. In some embodiments, a patient has a higher risk of PML if the patient is consistently positive for anti-JCV antibodies over a period of time, with an index level above a threshold value, e.g., with an index value of greater than 0.9, greater than 1.0, greater than 1.1, greater than 1.2, greater than 1.3, greater than 1.4, or greater than 1.5. In some embodiments, a patient has a high risk of PML if the patient has more two or more, e.g., 2, 3, 4, 5, 6, or more, consecutive samples over a period of time with an index level above a threshold value, e.g., with an index value of greater than 0.9, greater than 1.0, greater than 1.1, greater than 1.2, greater than 1.3, greater than 1.4, or greater than 1.5.

A patient satisfying these criteria can, optionally, be determined not to be a candidate to receive therapy with an anti-VLA-4 therapy, such as an anti-VLA-4 antibody, e.g., natalizumab, or the patient can further be assessed for other risk factors of developing PML. These risk factors include whether or not the patient has previously received an anti-VLA-4 therapy, such as natalizumab, and for how long the patient has received the therapy; and whether and for how long the patient has previously received an immunosuppressant therapy other than an anti-VLA-4 therapy. A patient's risk of PML may be a combination of each of these factors.

Antibody titer can be measured by "nOD" or "index." "nOD" is the normalized optical density value in a test, such as an ELISA test, for anti-JCV antibody detection. The "index" value is the optical density value for the sample divided by the optical density of the positive control in an immunoassay, such as the ELISA assay.

Applicants previously discovered that patients who received an anti-VLA-4 therapy, such as natalizumab, for 24 months or less, and who have not previously received an immunosuppressant therapy, are at lower risk for developing PML, than patients who do not meet these two criteria. Further, patients who have the lowest risk are those who meet these two criteria, and who are also JCV negative, e.g., patients who do not test positive for anti-JCV antibodies or JCV nucleic acid, e.g., JCV DNA. It was previously unknown that each of these three risk factors ((i) the amount of time the patient has previously received an anti-VLA-4 therapy; (ii) whether or not a patient has previously received treatment with an immunosuppressant other than an anti-VLA-4 therapy; and (iii) JCV status) independently contribute to a patient's risk of PML. The inventions described herein can be used in general for patients treated with a VLA-4 inhibitor. The ability to identify subpopulations of patients at distinctly different PML risks allows for better characterization of risk than previous methods (i.e., overall PML risk) and should assist healthcare professionals and patients in making more informed benefit-risk treatment decisions. These risk assessment criteria are described in co-owned U.S. provisional applications 61/491,810, filed May 31, 2011, and 61/508,584, filed Jul. 15, 2011. The contents of each of these provisional applications is hereby incorporated by reference in its entirety. The risk criteria described herein directed to anti-JCV antibody titer (e.g., as measured by nOD or index level) and, optionally percent inhibition can be considered in combination with the risk factors described in the prior co-owned provisional applications.

The methods for determining PML risk can require acquiring one, two or all three of a JCV classification for a patient (e.g., anti-JCV antibody titer, such as measured by nOD or index level and, optionally percent inhibition), prior anti-VLA-4 therapy history for the patient, and prior immunosuppressant therapy history (other than anti-VLA-4 therapy) for the patient. Responsive to these classifications, a patient can be assigned a treatment suitability classification. Patients who are determined to have low risk of developing PML can be assigned a positive treatment classification, and patients who are determined to have a higher relative risk of developing PML can be assigned a negative treatment classification. A patient who receives a positive treatment classification can receive a recommendation for further treatment or for initiating treatment with an anti-VLA-4 therapy. A patient receiving a negative treatment classification may receive a recommendation to terminate treatment with an anti-VLA-4, a recommendation to initiate treatment with a non-anti-VLA-4 therapy, a recommendation for continuing or initiating anti-VLA4 therapy with increased surveillance for signs and symptoms of PML.

A recommendation for further treatment with an anti-VLA-4 therapy may be accompanied with further instructions or requirements that the patient receive additional or enhanced monitoring, such as if one or more factors indicate that the patient may be at an increased risk of PML, e.g., prior treatment with an anti-VLA-4 therapy for longer than 24 months, e.g., 25 months or longer, or prior treatment with an immunosuppressant other than an anti-VLA-4 therapy.

A patient can be determined to have previously received an anti-VLA-4 therapy or an immunosuppressant therapy other than an anti-VLA-4 therapy through self-reporting by the patient, or through information (verbal or written) provided by a parent, physician, physician's assistant, nurse or other healthcare provider. The information can also be obtained through a database, such as a medical database or a clinical trials database.

Prior immunosuppressant therapies, other than anti-VLA-4 therapy, that will be indicative of an increased risk of PML can include prior treatment with antineoplastics, immunosuppressants or immunomodulators, such as one or more beta-interferon or glatiramer acetate. Exemplary immunosuppressants include, e.g., mitoxantrone, methotrexate, azathioprine, cyclophosphamide, and mycophenolate, anti-CD20 therapy (e.g., rituximab), an anti-CD11a therapy (e.g., efalizumab), or mycophenolate mofetil. Prior treatment with other immunosuppressant therapies as described below will also be predicted to increase a patient's risk of PML following further administration of an anti-VLA-4 therapy. In general, a determination of prior immunosuppressant use is a specified use which can be any prior use of an immunosuppressant that is not a VLA-4 inhibitor (e.g., an anti-VLA-4 antibody) (e.g., in the patient's lifetime) or prior use within a specified period of time, for example, within the previous 1, 2, 3, 5, or 10 years prior to the evaluation of PML risk.

Determining JCV status refers to determining whether a patient has been exposed to JCV and therefore includes direct methods of determining exposure (for example, detecting JCV proteins or JCV DNA) and indirect methods (e.g., detecting antibodies against JCV in a patient sample). Assays for determining JCV status can include assays for detecting JCV nucleic acid (e.g., DNA or RNA), or JCV seroprevalence, or anti-JCV antibodies in a biological sample, such as in plasma, serum, blood or urine sample, or in a sample of peripheral blood mononuclear cells (PBMCs), or cerebrospinal fluid. JCV nucleic acid can be detected using methods known in the art, for example, by an amplification method, e.g., polymerase chain reaction (PCR), or by a Next Generation Sequencing (NGS) method. JCV seroprevalence can be assayed using methods known in the art such as a haemagglutination inhibition (HI) assay. JCV antibodies can be detected by an immunoassay, such as an ELISA assay. In one embodiment, JCV antibodies can be detected by the method described in International Application Number PCT/US2011/20832, which utilizes HPVLPs under conditions suitable for binding of an anti-JCV antibody for detecting the level of anti-JCV antibody binding in a biological sample. Methods of determining JCV status also include methods of determining anti-JCV antibody titer and percent inhibition. Detection of anti-JCV antibody titer and percent inhibition typically include a two-step antibody detection assay as described in International Application Number PCT/US2011/20832.

If the presence of JCV is identified in a biological sample from a patient, e.g., JCV antibodies, proteins, peptides, or nucleic acids, the patient is determined to be "JCV positive." A positive JCV classification corresponds to the presence of JCV antibodies in the biological sample, e.g., JCV antibodies that are equal to or greater than a preselected criterion. The preselected criterion is typically a qualitative value, e.g., a "detectable" amount of antibody according to a particular assay, e.g., an immunoassay.

The methods described herein for determining PML risk can be useful for any human subject, including a subject considering treatment with an immunomodulator, for example an anti-VLA-4 therapy (e.g., natalizumab), an anti-CD20 therapy (e.g., rituximab), an anti-CD11a therapy (e.g., efalizumab), or mycophenolate mofetil; in a subject currently being treated with an immunomodulator; or a subject that has ceased treatment with an immunomodulator. The method may be useful to others who may be susceptible to PML such as individuals having lymphoproliferative disorders, such as multiple myeloma or a lymphoma; individuals infected with human immunodeficiency virus (HIV), or having acquired immune deficiency syndrome (AIDS), hematologic malignancies, or an autoimmune disease such as systemic lupus erythematosus (SLE), an inflammatory bowel disease, such as Crohn's Disease (CD) or ulcerative colitis, multiple sclerosis (MS) or arthritis, e.g., rheumatoid arthritis (RA). The risk-assessment method may also be useful to subjects receiving immunosuppressive or immunomodulatory therapies, such as transplant patients. Exemplary immunosuppressive or immunomodulatory therapies include natalizumab, rituximab, efalizumab, and mycophenolate mofetil. The method can be useful for assessing risk in a subject having a disorder, or being treated with a drug, disclosed in Piccinni et al. "Stronger association of drug-induced progressive multifocal leukoencephalopathy (PML) with biological immunomodulating agents" *Eur. J. Clin. Pharmacol.* 66:199-206, 2010, the contents of which are incorporated herein by reference.

Definitions

As used herein, an "HPVLP" is a highly purified VLP ("virus-like particle") consisting predominantly of the VP1 protein. An "HPVLP" featured in the invention is composed mainly of the major capsid protein "VP1," which can be a naturally-occurring VP1 or a recombinant VP1, from the polyomavirus, JC Virus (JCV). An HPVLP can be composed of, e.g., at least one pentameric subunit, more than one pentameric subunit, up to seventy-two pentameric subunits or more of VP1. An HPVLP of the invention can bind antibodies against naturally-occurring, intact JC virus. In some embodiments, an HPVLP includes a second, and optionally a third, polypeptide that is a minor capsid protein of JC virus, e.g., at least one VP2 or VP3 polypeptide. The VP2 or VP3 can be recombinant or naturally-occurring or naturally-derived polypeptides.

Such "highly purified" particles contain more than one VP1 pentamer, e.g., at least 5, 10, 20, 30, 40, 50, 60, 70, 72 VP1 pentamers, or less than 100 VP1 pentamers. Such highly purified particles can be obtained, for example, by a method that involves double filtration. For example, in one embodiment, a highly purified preparation of VLPs is obtained by purifying the particles at least twice by centrifugation, e.g., through a sucrose cushion. In other embodiments, HPVLPs are prepared using chromatographic methods. In general, an HPVLP preparation can be identified by its activity in an ELISA assay using defined control samples. In some cases, such control samples are negative controls and/or control samples containing low levels of JCV antibodies.

As used herein, a "high signal-to-noise HPVLP substrate" is a substrate on which is disposed HPVLP. It can be used to evaluate the level of free (that is unbound to antigen or other target, e.g., HPVLP, in a sample. The concentration of HPVLP on the substrate is such that, when measuring the amount of anti-JCV antibody present, it provides for a signal-to-noise ratio of 10 to 30, 15 to 30, 15 to 25, 18 to 22. In embodiment the signal-to-noise ratio is at least 10, 15, 18 or 20. In embodiments signal-to-noise ratio is about 10, 15, 18 or 20. The signal-to noise ratio can be determined with a sample, e.g., a calibration control, that gives an optical density of 1.0. In an embodiment the HPVLP is provided on said substrate at a concentration which results from lyophilizing 0.5 ml, 0.8 ml, 1.0 ml, 1.2 ml, or 1.5 ml of 0.4 µg/ml of HPVLP in a well of a 96 well plate. In an embodiment the HPVLP is provided on said substrate at a concentration which results from lyophilizing 1.0 ml of 0.4 µg/ml of HPVLP in a well of a 96 well plate, which as used herein, is equivalent to 30 ng to 50 ng (e.g., 40 ng) HPVLP per well. In an embodiment the HPVLP is provided on said substrate at a concentration which results from lyophilizing 0.05 ml to 0.35 mL or 0.1 ml to 0.2 ml of 0.4 µg/ml of HPVLP in a well of a 96 well plate. The amount of HPVLP disposed on the substrate, or the conditions under which deposition is achieved, can vary as long as the desired signal-to-noise ratio is obtained.

A signal-to-noise ratio is computed by comparing the optical density value of the negative control to the calibrator control to determine the dynamic range of the signal intensity in the assay.

In an embodiment the sample is diluted about 100 fold and the cut off for negative score is a reduction that is less than or equal to 45% and, the cutoff for a positive score is greater than 45%. In embodiments the dilution is other than 100 fold but is less than 200 fold. For example, the dilution is between 50- and 150-fold, 75- and 125-fold, 85- and 115-fold. In embodiments, the dilution is less than 150-fold, 125-fold, 100-fold, or 75-fold. In embodiments where the dilution is other than 100-fold (e.g., 200-fold 400-fold, 500-fold, 800-fold, up to >1,000,000-fold, the cutoff, or other parameters, are adjusted such that a sample would receive the same score (positive or negative) as it would if the dilution was 100-fold and the cut off for negative is less than 45% and the cut off for positive is greater than or equal to 45%.

Anti-JCV Antibody Detection Assay. Assays may be conducted by adding a biological sample to a substrate that has been coated with an HPVLP and detected using methods known in the art. In general, a solid base platform is used such as a microtiter plate (for example, a 96 well plate); although other formats known in the art can be used. In some embodiments, the biological sample is diluted prior to use in an assay.

In certain embodiments, the assay format is an enzyme-linked immunoassay (ELISA). Broadly, the method typically includes coating the substrate with capture antigen such as HPVLP, incubating sample containing binding antibodies directed to capture reagent, washing to remove non-specifically bound species, and detecting the bound immune complexes, e.g., by a chromogenic or chemiluminescent assay. Chromogenic substrates produce a colored end product, which can be detected and measured visually or with the use of a spectrophotometer. Chemiluminescent substrates produce light, which can be measured using a luminometer.

Coating a plate with HPVLP generally includes incubating the solid substrate (such as wells of a microtiter plate) with a solution of HPVLP at a suitable concentration (e.g., 0.4 µg/ml), either overnight or for a specified number of hours. The HPVLP can include VP1 as the only JCV viral component, or the HPVLP can be a heterologous particle, that contains at least one of VP2 or VP3 per particle or at least one each of VP2 and VP3 per particle. After coating with the HPVLP, the wells of the plate are washed. The substrate is then "coated" with a nonspecific protein that is antigenically neutral with regard to the samples to be tested. Suitable coating materials are known in the art and include bovine serum albumin (BSA), casein, sugars or solutions of milk powder. Plates may then be dried and stored for a longer period of time, such as 1 days, 1 month or 1 year prior to proceeding to the next step of the assay.

The sample or reference is incubated on the prepared substrate under conditions effective to permit complex formation (HPVLP/JCV antibody), thus forming a bound complex. Detection of the bound complex is performed using a labeled antibody that can bind to human antibody. In general, the labeled antibody can detect human IgG or human IgG and IgM. In some cases, the assay can be performed using secondary or tertiary detection methods.

A reference sample can be of the same biological material (e.g., plasma, serum, urine, or CSF) isolated from an individual known to be infected with JC virus based on the presence of JCV DNA in urine of the individual (uropositive). A reference sample is used to establish the assay cut-point such that the false negative rate of the assay is not greater than 1%-3%.

"Under conditions effective to permit complex formation" generally means conditions in which the reagents have been diluted to reduce background and provide readouts of results that lie within a specified range. Diluents can include, in non-limiting examples, solutions that include BSA, phosphate buffered saline (PBS), or PBS containing Tween.

"Suitable" conditions also include conditions that are at a temperature and/or for a period of time sufficient to allow effective binding. Incubations are typically from about one to two hours or one to four hours, at temperatures of approximately 25° C. to 27° C., or may be overnight at about 4° C. However, those in the art will understand that other conditions may be suitable.

In general, one or more washes are conducted between the incubations of the assay. Appropriate wash solutions include diluent buffer (e.g., PBS or PBS/Tween) or borate buffer.

In general, the detection of antibody bound to HPVLP is performed using methods well known in the art. In general, such methods are based on the detection of a label or marker, such as a radioactive, fluorescent, biological or enzymatic tag. U.S. patents concerning the use of such labels include, for example, U.S. Pat. Nos. 3,817,837; 3,850,752; 3,939,350; 3,996,345; 4,277,437; 4,275,149 and 4,366,241. In general, the detection of anti-JCV antibody binding is detected using a secondary antibody that is labeled. In general, the secondary antibody is specific for detecting human IgG. Quantification is achieved by measuring the degree of color generated, e.g., using a visible spectra spectrophotometer.

In one embodiment, the assay is performed in a medical office, such as by a healthcare provider, e.g., a doctor, a nurse or a technician, working in a facility where the biological sample is obtained from a patient. In another embodiment, the biological sample obtained from a patient is transported to another facility, e.g., to a third party facility, where the assay is performed. In this latter case, the results of the assay can be reported back to the healthcare provider, such as through a form, which can be submitted by mail or electronically (e.g., through facsimile or e-mail) or through an on-line database. In one embodiment, the results of the assay (including the screening assay and, optionally, a confirmatory assay) can be stored in a database and can be accessed by a healthcare provider, such as through the worldwide web.

Secondary Test. In some cases, for example, when the level of anti-JCV antibody in a sample falls into a designated "equivocal zone" or "indeterminate zone," e.g., where it is determined that there is limited certainty regarding the presence or absence of anti-JCV antibody (such as when the nOD value is determined to be >0.2 and <0.4), a secondary test (also referred to herein as a "confirmatory assay") of the sample is employed. For the secondary test, two aliquots of a biological sample are used. The first is prepared prior to use in the assay by preincubating the sample in the presence of assay buffer in solution for a period of time (e.g., for 30 minutes, one hour, or longer such as overnight at 4° C.). The second aliquot is prepared prior to use in the assay by preincubating the sample in the presence of HPVLP in solution for a period of time (e.g., for 30 minutes, or one hour or longer). The two aliquots are then used in the HPVLP assay as described herein, and the assignment of the sample to anti-JCV antibody positive or antibody negative is made. If the assay results for the aliquot incubated with HPVLP indicate a value of <45% inhibition (i.e., the "cut-point"), then the sample is interpreted to be negative for the presence of JCV-specific antibodies. If the assay results indicate a value of ≥45% inhibition, then the sample is interpreted to have JCV-specific antibodies and therefore as antibody positive.

An assay featured in the invention that utilizes a secondary test is also referred to herein as a "two-step test" or a "two-step assay." An earlier version of the two step assay is described in co-owned International Application No. PCT/US2011/020832, which is incorporated by reference herein in its entirety.

Substrates and Solution Based Methods. Any suitable solid substrate can be used for the HPVLP assay format. In some embodiments, the substrate is a microtiter plate (e.g., a 96-well plate) a slide, a bead, or a column. The substrate can be suitable for chromogenic or chemiluminescent detection methods, or solution based methods such as proximal ligation.

Cut-point. The invention provides methods of analysis that employ "cut-points" to reduce false negative and false positive rates. The cut-points are established based on data from the HPVLP assays (e.g., to detect JCV antibodies in a biological sample), averaged, for example, between duplicate test samples and multiple replicates (for example, at least two, at least four, or at least eight replicates of control samples). Cut-points can also be determined statistically using large panels of non-PML and PML samples. In some embodiments, the cut-point is determined to be an anti-JCV antibody index of 0.7, 0.8, 0.9, 1.0, 1.1, 1.2, 1.3, 1.4, or 1.5.

In one version of an assay according to the present invention, results from initial HPVLP screening assays, e.g., ELISA assays, will cause a test sample to be classified as having or not having JCV-specific antibodies, or, if the sample does not fall under one of these two classifications, then the sample will be subjected to a supplemental confirmation assay. For example, samples that produce a result in an HPVLP ELISA assay featured in the invention less than an established level (e.g., an $nOD_{450}$<0.2) will be classified as lacking JCV-specific antibodies, and samples that provide a result in the ELISA greater than an established level (e.g., an $nOD_{450}$>0.4) will be classified as positive for JCV-specific antibodies. Samples that do not clearly fall into one of these classifications (e.g., 0.2<$OD_{450}$<0.4) can be tested in a confirmatory assay.

In one embodiment, the confirmatory assay requires a pre-incubation step, where the test sample is pre-incubated with buffer (or other suitable solution) control or with HPVLPs (in buffer or other suitable solution) to pre-adsorb JCV-specific antibodies prior to analysis in an HPVLP ELISA, as described in further detail below. After pre-incubation with HPVLP if the reaction in the primary assay decreases by less than 45% compared to buffer control, then the sample is interpreted to be negative for the presence of JCV-specific antibodies. If the results show a ≥45% reduction in reaction compared to buffer control in the primary assay after pre-incubation with HPVLP then the sample is interpreted to contain JCV specific antibodies. In some embodiments, only the confirmatory assay is performed.

VP1. The use of HPVLPs in an assay for JCV antibodies can improve the accuracy of the assay and is useful in an assay suitable for analytic and diagnostic purposes. VP1 for use in producing HPVLPs can be generated using methods known in the art and can be either naturally-occurring VP1 or recombinantly produced VP1, e.g., a VP1 from a JC virus. In general, the VP1 used is VP1 from a MAD1 strain of JCV. In some embodiments, the VP1 used in the assay comprises VP1 from more than one JCV strain, for example, from one or more of strains 1A, 1B, 2A, 2B, 3, 4, and 7. After preparation of VP1, e.g., recombinantly synthesized VP1, the VP1 for use in the assays described herein is then further purified through standard biochemical methods including density-gradient/ultracentrifugation methods, or a series of chemical precipitation steps, concentration/diafiltration and ion-exchange chromatography. The purification methods typically include a step to remove smaller proteins including monomer VP1 polypeptides, or pentamer VP1. The removal of these smaller particles can be done in, for example, in one step or in two steps (e.g., a first filtration step to remove VP1 monomers, and then a second filtration step to remove pentamer VP1 particles). Such biochemical purification methods are known to those in the art. Examples 1 and 7 provide two different methods of JCV VP1-VLP purification.

An HPVLP preparation (HPVLPs) according to one aspect of the present invention does not contain significant amounts of VP1 monomer (e.g., has been purified to remove monomers). An HPVLP preparation according to another aspect of the present invention does not contain significant amounts of VP1 molecules in configurations the size of a VP1 pentamer, or smaller (including monomer). The HPVLP can be prepared from recombinant VP1 or naturally-occurring VP1 (e.g., isolated from virus or virus capsid). In some embodiments, additional JCV components, such as one or both of the minor coat proteins from JC virus, e.g., VP2 or VP3, are included in the HPVLP particle or are associated with the substrate.

In some cases, recombinantly expressed VP1 may not assemble into pentamers or HPVLPs that resemble naturally-occurring viral capsids, for example, recombinantly expressed VP1 may assemble into tubes or other non-spherical geometries. Accordingly, the invention relates to methods of producing HPVLPs that are substantially spherical in geometry. The invention includes HPVLP preparations where at least about 10%, about 15%, about 20%, about 25%, about 50%, about 60%, about 65%, about 70%, about 80%, about 90%, about 95%, or about 99% of the HPVLPs in the preparation resemble the naturally-occurring JCV capsid (e.g., are in an icosahedral or substantially spherical configuration). In some embodiments, an HPVLP preparation contains at least 10%, at least 15%, at least 20%, at least 50%, at least 60%, at least 70%, at least 80%, at least 90%, at least 95%, or at least 99% of the HPVLPs in the preparation resemble the naturally-occurring JCV capsid. Such methods can include expressing viral proteins under conditions that result in such a preparation and/or isolating and purifying expressed viral proteins as described herein to produce such a preparation.

Methods of Making HPVLPs. HPVLPs can be made, for example, by transforming a baculovirus with a vector expressing a VP1 gene, such as a VP1 gene from a JC virus. The baculovirus is used to infect a cell culture, such as an insect cell culture (e.g., SF9 cells) or a mammalian cell culture, and the cells express the VP1 protein. HPVLPs are isolated by lysing the cells, and purifying the particles through a series of centrifugation and ultrafiltration steps. In general, the purification is performed using methods such as sucrose cushion sedimentation, isopycnic ultracentrifugation and extensive ultrafiltration or other methods known to those in the art. In certain embodiments, the purification will include twice centrifuging the particles through a sucrose cushion. In an alternative purification method, cells are lysed, and particles are isolated by a series of precipitation and concentration/diafiltration steps with a final ion-exchange step. In yet another alternative method, the HPVLPs are purified by chromatographic methods, and without centrifugation steps.

Purity can be assessed using any suitable techniques known in the art, for example, analytical ultracentrifugation, electron microscopy, PAGE analysis, mass spectrometry, protein concentration, or activity in an ELISA with control sera. Insufficiently purified VLPs result in a high background yielding falsely high anti-JCV antibody levels or calculated exposure rates.

In some embodiments, the HPVLPs contain VP1 as the sole JC virus protein.

In some embodiments, the HPVLPs are heterogeneous particles, and therefore include VP1 protein, and at least one of the minor coat proteins of JC virus, e.g., VP2 or VP3. In another embodiment, the HPVLP includes VP1, VP2 and VP3 proteins. An HPVLP that includes VP1 and VP2 can be produced using methods known in the art, for example, by transforming a baculovirus with a nucleic acid including a VP1 and a VP2 gene, such as under the control of the same or different promoters. A cell culture is infected with the baculovirus, and the cells express VP1 and VP2, and HPVLPs form which include both types of proteins. In one embodiment, the VP1 and VP2 genes are on different DNA molecules, the DNA molecules are transformed into different baculoviruses and the baculoviruses are used to transfect cells in the same culture. The cells express the VP1 and VP2 proteins, and HPVLPs form which include both types of protein. In some cases, a heterogeneous HPVLP will include, e.g, one or two VP2 polypeptides for every five VP1 polypeptides. In general, an HPVLP will contain more VP1 polypeptides than VP2 polypeptides, as is the case in naturally-occurring JC virus.

An HPVLP that includes both VP1 and VP3 or both VP1 and VP2 molecules can be produced, for example, by transforming a baculovirus with a nucleic acid including a VP1 and a VP3 gene or a VP1 and VP2 gene, respectively, under the control of the same or different promoters. A cell culture is infected with the baculovirus, and the cells express VP1 and VP3 or VP1 and VP2, and HPVLPs form which include both types of proteins. In some embodiments, the VP1 and VP3 or VP1 and VP2 genes are on different DNA molecules, the DNA molecules are transformed into different baculoviruses, and the baculoviruses are used to transfect cells in the same culture. The cells express the VP1 and VP3 proteins or VP1 and VP2 genes, respectively, and HPVLPs form which include both types of protein. HPVLP particles can be isolated from such preparations using methods known in the art such as those used to isolate JCV capsids.

Typically, a VP1 pentamer that is in a heterogeneous HPVLP will include, e.g, five VP1 polypeptides and one VP3 polypeptide and/or one VP2 polypeptide, depending on whether a VP3 gene or VP2 gene was used to make the constructs. There will typically be more VP1 polypeptides than VP3 or VP2 polypeptides in an HPVLP. In some embodiments, the VP2 or VP3 is from a polyoma virus that is not a JC virus, e.g., a BK virus polypeptide.

An HPVLP that includes all three of VP1 and VP2 and VP3 molecules can be produced by transforming a baculovirus with a nucleic acid (e.g., a circular DNA, e.g., <5.5 kb) including a VP1, VP2 and VP3 gene, such as under the control of the same or different promoters. A cell culture, such as a mammalian cell culture, is infected with the baculovirus, and the cells express VP1, VP2 and VP3 proteins. HPVLPs consequently form which include all three types of proteins. In one embodiment, the VP1, and either or both of the VP2 and VP3 genes are on different DNA molecules, the DNA molecules are transformed into the same or different baculovirus, and the baculovirus are used to infect cells in the same or separate cultures. The cells express the VP1, VP2 and VP3 proteins, and HPVLPs form which include both types of protein. A heterogeneous HPVLP can include, e.g, five VP1 polypeptides and one each of VP2 and VP3 polypeptides, although the ratios may vary within a preparation. There will typically be more VP1 polypeptides than VP2 and VP3 polypeptides in an HPVLP.

In some embodiments, the HPVLP will be greater in size than a VP1 pentamer. By greater in size, it is meant that the mass of protein contained in an HPVLP particle is greater than a pentamer containing solely VP1.

In other embodiments, the method of preparing a solution of HPVLP can include removing from the solution particles (e.g., VP1 monomers or small VP1 containing particles) that are the size of a VP1 pentamer or smaller. Methods such as centrifugation and size-exclusion chromatography can be used to perform this purification step. In some embodiments, other methods known in the art, e.g., ion exchange chromatography, can be used in the preparation of HPVLPs that are larger than a VP1 pentamer. In general, an HPVLP preparation suitable for use in an assay will contain at least 20% HPVLPs, at least 25% HPVLPs, at least 40% HPVLPs, at least 60% HPVLPs, at least 65% HPVLPs, at least 70% HPVLPs, at least 80% HPVLPs, at least 85% HPVLPs, at least 90% HPVLPs, at least 95% HPVLPs, or at least 99% HPVLPs compared to non-HLVLP particles (e.g., by percent of pentamers compared to VP1 monomers and aggregates containing fewer than five VP1 molecules).

Methods of Evaluating Samples and/or Subjects. As used herein, methods of evaluating or analyzing a subject or biological sample from a subject include one or more of performing the analysis of the sample, requesting analysis of the sample, requesting results from analysis of the sample, or receiving the results from analysis of the sample. (Generally herein, determination (or determining), analysis or evaluation (or evaluating) can include one or both of performing the underlying method or receiving data from another who has performed the underlying method.)

The analysis or evaluation requires a transformation of material, e.g., biological material or assay components. For example, a biological sample can be evaluated for the presence of anti-JCV antibodies, anti-JCV antibody titer and percent inhibition of JCV antibodies. The evaluation can be performed before or after or at the same time the patient is receiving treatment, such as for MS. The evaluation is based, at least in part, on analysis of a sample from the subject, e.g., a blood, plasma, serum, urine or CSF sample. The presence of anti-JCV antibodies can be determined by contact with a specific binding agent, e.g., a JCV protein, such as VP1. The binding agent can be a JCV protein, e.g., VP1 in the form of a particle, e.g., a HPVLP.

In one embodiment, an assay to detect the presence of anti-JCV antibodies is a two-step assay, such as described herein. The assay utilizes HPVLPs under conditions suitable for binding an anti-JCV antibody. The assay is capable of detecting any isotype of anti-JCV antibody (including IgG, IgM, IgA, and IgE). The assay is also highly sensitive and can detect anti-JCV antibodies at a concentration of, for example, 2.0 µg/mL or less, e.g. 1.5 µg/mL or less, 1.25 µg/mL or less, 1.0 µg/mL or less, 0.5 µg/mL or less, 50 ng/ml or less, 10 ng/ml or less, 5 ng/mL or less, 1.7 ng/ml or less, or 1 ng/ml or less.

In one embodiment, the sample is analyzed for the level of JCV nucleic acid present in the sample. For example, nucleic acids can be isolated from the sample and used for PCR amplification or a Next-Generation (Nex-Gen) Sequencing technique. In one embodiment, a crude lysate of the biological sample is subject to an amplification method, such as PCR, and the amplified product is analyzed by one or more of electrophoresis, restriction fragment mapping, hybridization or sequencing to identify whether JCV DNA or RNA is present in the sample and how much is in the sample.

The biological sample can be removed from the patient and analyzed.

In some embodiments, the patient sample, e.g., a serum or plasma or whole blood sample or CSF, can be stored prior to testing for JCV, e.g., for JCV antibodies or for JCV nucleic acid. The patient sample, e.g., the patient sample containing JCV antibodies or JCV nucleic acid, can be stored for 1-21 days, e.g., 1-14 days or 1-7 days or longer (e.g., one day, two days, three days, five days, seven days, ten days, 14 days, 21 days or longer); for one to six weeks, e.g., one to three weeks or one to two weeks or longer (e.g., up to one week, up to two weeks, up to three weeks, up to six weeks, or longer); or for one to six months, e.g., one to three months or one to two months or longer (e.g., up to one month, up to two months, up to three months, up to six months or longer). The sample can be stored, for example, frozen (e.g., at −80° C. to −20° C.), at 2-8° C., at ambient temperature (18° C.-25° C.) or warmer, e.g., at 37° C.

As used herein, the term "acquire" or "acquiring" refers to obtaining possession of a physical entity, or a value, e.g., a numerical value, by "directly acquiring" or "indirectly acquiring" the physical entity or value, e.g., the status of a patient, such as prior exposure to anti-VLA-4 therapy or other immunosuppressants, or JCV status. "Directly acquiring" means performing a process (e.g., performing a synthetic or analytical method) to obtain the physical entity or value. "Indirectly acquiring" refers to receiving the physical entity or value from another party or source (e.g., a third party laboratory that directly acquired the physical entity or value). Directly acquiring a physical entity includes performing a process that includes a physical change in a physical substance, e.g., a starting material. Exemplary changes include making a physical entity from two or more starting materials, shearing or fragmenting a substance, separating or purifying a substance, combining two or more separate entities into a mixture, performing a chemical reaction that includes breaking or forming a covalent or non-covalent bond. Directly acquiring a value includes performing a process that includes a physical change in a sample or another substance, e.g., performing an analytical process which includes a physical change in a substance, e.g., a sample, analyte, or reagent (sometimes referred to herein as "physical analysis"), performing an analytical method, e.g., a method which includes one or more of the following: separating or purifying a substance, e.g., an analyte, or a fragment or other derivative thereof, from another substance; combining an analyte, or fragment or other derivative thereof, with another substance, e.g., a buffer, solvent, or reactant; or changing the structure of an analyte, or a fragment or other derivative thereof, e.g., by breaking or forming a covalent or non covalent bond, between a first and a second atom of the analyte; or by changing the structure of a reagent, or a fragment or other derivative thereof, e.g., by breaking or forming a covalent or non covalent bond, between a first and a second atom of the reagent.

At least one or both of determining a patient's status (e.g., JCV status), or an activity level, and determining if the status has a preselected relationship with a reference criterion, includes one or more of analyzing a sample, requesting analysis of the sample, requesting results from analysis of the sample, or receiving the results from analysis of the sample. (Generally, analysis can include one or both of performing the underlying method (e.g., an immunoassay) or receiving data from another who has performed the underlying method.)

Anti-VLA-4 therapy. An anti-VLA-4 therapy is a molecule, e.g., a small molecule compound or protein biologic (e.g., an antibody or fragment thereof, such as an antigen-binding fragment thereof) that blocks VLA-4 activity. The molecule that is the anti-VLA-4 therapy is a VLA-4 antagonist. A VLA-4 antagonist includes any compound that inhibits a VLA-4 integrin from binding a ligand and/or receptor. An anti-VLA-4 therapy can be an antibody (e.g., natalizumab (TYSABRI®)) or fragment thereof, or a soluble form of a ligand. Soluble forms of the ligand proteins for α4 integrins include soluble VCAM-I or fibronectin peptides, VCAM-I fusion proteins, or bifunctional VCAM-I/Ig fusion proteins. For example, a soluble form of a VLA-4 ligand or a fragment thereof may be administered to bind to VLA-4, and in some instances, compete for a VLA-4 binding site on cells, thereby leading to effects similar to the administration of antagonists such as anti-VLA-4 antibodies. For example, soluble VLA-4 integrin mutants that bind VLA-4 ligand but do not elicit integrin-dependent signaling are suitable for use in the described methods. Such mutants can act as competitive inhibitors of wild type integrin protein and are considered "antagonists." Other suitable antagonists are "small molecules."

"Small molecules" are agents that mimic the action of peptides to disrupt VLA-4/ligand interactions by, for instance, binding VLA-4 and blocking interaction with a VLA-4 ligand (e.g., VCAM-I or fibronectin), or by binding a VLA-4 ligand and preventing the ligand from interacting with VLA-4. One exemplary small molecule is an oligosaccharide that mimics the binding domain of a VLA-4 ligand (e.g., fibronectin or VCAM-I) and binds the ligand-binding domain of VLA-4. (See, Devlin et al., *Science* 249:400-406 (1990); Scott and Smith, *Science* 249:386-390 (1990); and U.S. Pat. No. 4,833,092 (Geysen), all incorporated herein by reference.)

A "small molecule" may be chemical compound, e.g., an organic compound, or a small peptide, or a larger peptide-containing organic compound or non-peptidic organic compound. A "small molecule" is not intended to encompass an antibody or antibody fragment. Although the molecular weight of small molecules is generally less than 2000 Daltons, this figure is not intended as an absolute upper limit on molecular weight.

Combination Therapy or Alternatives to Anti-VLA-4 Therapy. In some embodiments, the anti-VLA-4 therapy, e.g., natalizumab, is administered with a second agent, or an alternative therapy can be administered instead of the anti-VLA-4 therapy, such as when a patient is determined to be at higher risk for PML.

Non-limiting examples of second agents for treating multiple sclerosis in combination with the anti-VLA-4 therapy, or alternative agents for use instead of the anti-VLA-4 therapy, include: fumaric acid salts, such as dimethyl fumarate; Sphingosine 1-phosphate (S1P)-antagonists, such as the S1B-blocking antibody Sphingomab; interferons, such as human interferon beta-1a (e.g., AVONEX® or Rebif®)) and interferon β-1b (BETASERON® human interferon β substituted at position 17; Berlex/Chiron); glatiramer acetate (also termed Copolymer 1, Cop-1; COPAXONE® Teva Pharmaceutical Industries, Inc.); an antibody or a fragment thereof (such as an antigen-binding fragment thereof), such as an anti-CD20 antibody, e.g., Rituxan® (rituximab), or an antibody or fragment thereof that competes with or binds an overlapping epitope with rituximab; mixtoxantrone (NOVANTRONE®, Lederle); a chemotherapeutic agent, such as clabribine (LEUSTATIN®), azathioprine (IMURAN®), cyclophosphamide (CYTOXAN®), cyclosporine-A, methotrexate, 4-aminopyridine, and tizanidine; a corticosteroid, such as methylprednisolone (MEDRONE®, Pfizer), or prednisone; CTLA4 Ig; alemtuzumab (MabCAMPATH®) or daclizumab (an antibody that binds CD25); statins; and TNF antagonists.

Glatiramer acetate is a protein formed from a random chain of amino acids (glutamic acid, lysine, alanine and tyrosine (hence GLATiramer)). Glatiramer acetate can be synthesized in solution from these amino acids at a ratio of approximately 5 parts alanine to 3 parts lysine, 1.5 parts glutamic acid and 1 part tyrosine using N-carboxyamino acid anhydrides.

Additional second agents, or agents for use in place of the anti-VLA-4 therapy, include antibodies or antagonists of other human cytokines or growth factors, for example, TNF, LT, IL-1, IL-2, IL-6, IL-7, IL-8, IL-12 IL-15, IL-16, IL-18, EMAP-11, GM-CSF, FGF, and PDGF. Still other exemplary second agents include antibodies to cell surface molecules such as CD2, CD3, CD4, CD8, CD25, CD28, CD30, CD40, CD45, CD69, CD80, CD86, CD90 or their ligands. For example, daclizubmab is an anti-CD25 antibody that may ameliorate multiple sclerosis.

Still other exemplary antibodies include antibodies that provide an activity of an agent described herein, such as an antibody that engages an interferon receptor, e.g., an interferon beta receptor. Typically, in implementations in which the second agent includes an antibody, it binds to a target protein other than VLA-4 or other than an α4 integrin, or at least an epitope on VLA-4 other than one recognized by natalizumab.

Still other additional exemplary second agents include: FK506, rapamycin, mycophenolate mofetil, leflunomide, non-steroidal anti-inflammatory drugs (NSAIDs), for example, phosphodiesterase inhibitors, adenosine agonists, antithrombotic agents, complement inhibitors, adrenergic agents, agents that interfere with signaling by proinflammatory cytokines as described herein, IL-1β converting enzyme inhibitors (e.g., Vx740), anti-P7s, PSGL, TACE inhibitors, T-cell signaling inhibitors such as kinase inhibitors, metalloproteinase inhibitors, sulfasalazine, azathloprine, 6-mercaptopurines, angiotensin converting enzyme inhibitors, soluble cytokine receptors and derivatives thereof, as described herein, anti-inflammatory cytokines (e.g. IL-4, IL-10, IL-13 and TGF).

In some embodiments, a second agent may be used to treat one or more symptoms or side effects of MS. Such agents include, e.g., amantadine, baclofen, papaverine, meclizine, hydroxyzine, sulfamethoxazole, ciprofloxacin, docusate, pemoline, dantrolene, desmopressin, dexamethasone, tolterodine, phenytoin, oxybutynin, bisacodyl, venlafaxine, amitriptyline, methenamine, clonazepam, isoniazid, vardenafil, nitrofurantoin, psyllium hydrophilic mucilloid, alprostadil, gabapentin, nortriptyline, paroxetine, propantheline bromide, modafinil, fluoxetine, phenazopyridine, methylprednisolone, carbamazepine, imipramine, diazepam, sildenafil, bupropion, and sertraline. Many second agents that are small molecules have a molecular weight between 150 and 5000 Daltons.

Examples of TNF antagonists include chimeric, humanized, human or in vitro generated antibodies (or antigen-binding fragments thereof) to TNF (e.g., human TNF α), such as D2E7, (human TNFα antibody, U.S. Pat. No. 6,258,562; BASF), CDP-571/CDP-870/BAY-10-3356 (humanized anti-TNFα antibody; Celltech/Pharmacia), cA2 (chimeric anti-TNFα antibody; REMICADE™, Centocor); anti-TNF antibody fragments (e.g., CPD870); soluble fragments of the TNF receptors, e.g., p55 or p75 human TNF receptors or derivatives thereof, e.g., 75 kd TNFR-IgG (75 kD TNF receptor-IgG fusion protein, ENBREL™; Immunex; see, e.g., *Arthritis & Rheumatism* 37:S295, 1994; *J. Invest. Med.* 44:235A, 1996), p55 kdTNFR-IgG (55 kD TNF receptor-IgG fusion protein (LENERCEPT™)); enzyme antagonists, e.g., TNFα converting enzyme (TACE) inhibitors (e.g., an alpha-sulfonyl hydroxamic acid derivative, WO 01/55112, and N-hydroxyformamide TACE inhibitor GW 3333, -005, or -022); and TNF-bp/s-TNFR (soluble TNF binding protein; see, e.g., *Arthritis & Rheumatism* 39:S284, 1996; *Amer. J. Physiol.—Heart and Circulatory Physiology* 268:37-42, 1995).

In one implementation, the anti-VLA-4 therapy and the second agent are provided as a co-formulation, and the co-formulation is administered to the subject. It is further possible, e.g., at least 24 hours before or after administering the co-formulation, to administer separately one dose of the anti-VLA-4 therapy formulation and then one dose of a formulation containing the second agent. In another implementation, the anti-VLA-4 therapy and the second agent are provided as separate formulations, and the step of administering includes sequentially administering the anti-VLA-4 therapy and the second agent. The sequential administrations can be provided on the same day (e.g., within one hour of one another or at least 3, 6, or 12 hours apart) or on different days.

The anti-VLA-4 therapy and the second agent each can be administered as a plurality of doses separately in time. The anti-VLA-4 therapy and the second agent are typically each administered according to a regimen. The regimen for one or both may have a regular periodicity. The regimen for the anti-VLA-4 therapy can have a different periodicity from the regimen for the second agent, e.g., one can be administered more frequently than the other. In one implementation, one of the anti-VLA-4 therapy and the second agent is administered once weekly and the other once monthly. In another implementation, one of the anti-VLA-4 therapy and the second agent is administered continuously, e.g., over a period of more than 30 minutes but less than 1, 2, 4, or 12 hours, and the other is administered as a bolus. The anti-VLA-4 therapy and the second agent can be administered by any appropriate method, e.g., subcutaneously, intramuscularly, or intravenously.

In some embodiments, each of the anti-VLA-4 therapy and the second agent is administered at the same dose as each is prescribed for monotherapy. In other embodiments, the anti-VLA-4 therapy is administered at a dosage that is equal to or less than an amount required for efficacy if administered alone. Likewise, the second agent can be administered at a dosage that is equal to or less than an amount required for efficacy if administered alone.

Kits. Reagents for performing an anti-JCV antibody assay can be provided in the form of a kit. Except for the patient sample, some or all materials required for the assay can be provided in the kit. A kit can include for example, a substrate, such as a plate with wells coated with JCV antigen substrate, e.g., HPVLP. The plate can be for example a 6-well plate, a 12-well plate, a 24-well plate, a 48-well plate, a 96-well plate or a 384 well plate. The plates provided in a kit can be pre-coated with JCV VLP antigen, such as at 0.4 µg/mL. In one embodiment the kit includes materials and reagents for use with high-throughput systems such as SPR (Solid Phase Receptacle) tips for use with bioMerieux systems.

The kit can also include JCV antigen, e.g., HPVLP lyophilized or in solution, such as for use with the confirmation step of the assay. In one embodiment, the kit includes a JCV cut-off calibrator, an anti-JCV antibody positive control and a JCV negative control, which are samples of sera, such as human sera. Solutions containing JCV antigen and sera can include a preservative, such as sodium azide, e.g., 0.05%, 0.1%, 1.5%, and 2% sodium azide. In one embodiment, a kit featured in the invention can include one or more reagents for detecting a complex containing anti-JCV antibodies bound to antigen, such as HPVLP. Reagents for detecting the complex include, for example, a JCV conjugate, a casein sample, a detectable reagent, such as TMB (tetramethylbenzidine), a wash buffer, and a stop reagent.

The JCV substrate can be, for example, an anti-human antibody, such as an enzyme-conjugated anti-human antibody. In one embodiment, the JCV conjugate is an affinity-purified and peroxidase-conjugated donkey anti-human antibody. In another embodiment, the casein solution contains casein, a surfactant and a non-azide preservative in buffer (e.g., phosphate buffered saline (PBS)). In another embodiment, the TMB substrate solution includes TMB and hydrogen peroxide in buffer. In another embodiment, the kit includes a wash buffer, and the wash buffer can contain, for example, surfactant in PBS with non-azide preservatives. The stop reagent can be, for example, an acid, such as sulfuric acid (e.g., 1 M sulfuric acid).

The solutions provided in the kit can be provided at concentrated levels such that dilution is required before use. The HPVLP for use in solution binding to anti-JCV antibody in a biological sample, such as in the confirmation step of the two-step assay, can be provided as a concentration of 2 mg/mL, 1.5 mg/mL, 1 mg/mL, 0.5 mg/mL, for use at, for example, 10 µg/mL, 5 µg/mL, 1 µg/mL, 0.8 µg/mL, 0.4 µg/mL, 0.2 µg/mL The wash buffer, for example, can be provided at 10× concentration. The JCV substrate (such as an affinity-purified and peroxidase-conjugated donkey anti-human antibody) can be provided at, for example, 1 mg/mL, 0.8 mg/mL or 0.6 mg/mL, for dilution by, e.g., 1:40,000, 1:30,000, 1:20,000 or 1:20,000 prior to use in an anti-JCV antibody detection assay.

Materials for sealing the reaction mixes, such as sealing tape, can also be included in the kit.

Reporting of results. The results of the risk-assessment analysis can be reported, such as to a treatment center, or a healthcare provider, or an insurance provider. In one embodiment, the results of the risk-assessment are stored in a database.

In one embodiment, informational material is provided for performing and interpreting the risk assessment. The informational material can provide guidance as to where to report the results of the assessment, such as to a treatment center or healthcare provider or database provider. The informational material can be provided in a kit or a packet, and can include forms for reporting the results of the assessment, including each prong of the assessment (information regarding prior treatment with anti-VLA-4 therapies, prior treatment with immunosuppressants, and JCV status), and address and contact information regarding where to send such forms or other related information; or a URL (Uniform Resource Locator) address for reporting the results in an online database or an online application (e.g., an "app"). In another embodiment, the informational material can include guidance regarding whether a patient should receive treatment with an anti-VLA-4 therapy, depending on the patient's risk of PML according to the results of the risk assessment.

The kit or packet may also include instructions and items for the collection or transport of a patient sample to a healthcare provider, or for receiving a sample from a healthcare provider, or for performing the evaluative methods described herein. For example, besides instructional information, a kit or packet featured in the invention can include one or more of a swab or scraper, or a vessel (e.g., a cup, a test tube, an ampoule, or a bag) for collecting, and storing and transporting a biological sample. The kit or packet may also contain supplies for performing an immunoassay or a sequencing assay for detection of JCV antibodies or nucleic acids, respectively.

A kit can include one or more containers for the reagents required for an assay, e.g., a JCV-detection assay. The reagents can be provided in a concentration suitable for use in the assay or with instructions for dilution for use in the assay. In some embodiments, the kit contains separate containers, dividers or compartments for the assay components, and the informational material. For example, the assay components can be contained in a bottle or vial, and the informational material can be contained in a plastic sleeve or packet. In other embodiments, the separate elements of the kit are contained within a single, undivided container. For example, an assay reagent is contained in a bottle or vial that has attached thereto the informational material in the form of a label. In some embodiments, the kit includes a plurality (e.g., a pack) of individual containers, each containing one or more unit forms (e.g., for use with one assay) of an assay component. For example, the kit includes a plurality of ampoules, foil packets, or blister packs, each containing a single unit of assay reagent for use in a screening or confirmatory assay. The containers of the kits can be air tight and/or waterproof. The container can be labeled for use.

The informational material of a kit or packet is not limited in its form. In many cases, the informational material, e.g., instructions, is provided in printed matter, e.g., a printed text, drawing, and/or photograph, e.g., a label or printed sheet. However, the informational material can also be provided in other formats, such as computer readable material, video recording, or audio recording. In another embodiment, the informational material of the kit is contact information, e.g., a physical address, email address, website, or telephone number, where a user of the kit or packet can obtain substantive information about how to find the information required for the risk assessment analysis, e.g., where and how to identify prior treatments administered to a subject, and how to perform an assay to determine the JCV status of a patient. The informational material can also be provided in any combination of formats.

In some embodiments, a biological sample is provided to an assay provider, e.g., a service provider (such as a third party facility) or a healthcare provider, who evaluates the sample in an assay and provides a read out. For example, in one embodiment, an assay provider receives a biological sample from a subject, such as a plasma, blood or serum sample, and evaluates the sample using an assay described herein, and determines that the sample contains JCV antibodies or nucleic acid. In some embodiments, the assay provider, e.g., a service provider or healthcare provider, can further determine, e.g., by contacting a healthcare provider or a database service provider, the amount of prior anti-VLA-4 therapy that a patient has received or whether a patient has previously received treatment with an immunomodulator. The assay provider can further determine that the subject is not a candidate to receive treatment with an anti-VLA-4 therapy, such as natalizumab, or that the subject is a candidate to receive treatment with an immunomodulator, or that the subject may be a candidate who should have enhanced monitoring as compared to a subject who is determined to have a negative JCV status (e.g., who tests negative for JCV nucleic acid or anti-JCV antibodies). For example, a candidate who has received prior treatment with an anti-VLA-4 therapy for 24 months or less, and who has not received prior therapy with an immunosuppressant, but who is determined to be JCV positive, can be selected as a candidate to receive further anti-VLA-4 therapy, but with a recommendation to monitor the patient more frequently for the development of adverse symptoms, such as symptoms that may indicate the development of PML.

In one embodiment, the assay provider performs an assessment for PML risk as described herein and determines that subject is a candidate to receive treatment with an anti-VLA-4 therapy, such as natalizumab. In one embodiment, the assay provider informs a healthcare provider that the subject is a candidate for treatment with the anti-VLA-4 therapy, and the candidate is administered the anti-VLA-4 therapy. For example, the assay provider may determine that a patient is at a lower risk for PML and subsequently inform the healthcare provider of the determination of the lower risk and that the subject is a candidate for treatment with the anti-VLA-4 therapy.

In another example, the assay provider determines that a patient is at a higher risk for PML and subsequently informs a healthcare provider of the determination of the higher risk, and recommends that the patient is a candidate for treatment with the anti-VLA-4 therapy, but that the patient should undergo increased testing for PML and, optionally, JCV status. In one embodiment, the assay provider informs the healthcare provider that the patient is at higher risk of PML and therefore the patient should receive an alternative to anti-VLA-4 therapy, or the patient is a candidate to receive anti-VLA-4 therapy with increased testing for PML and, optionally, JCV status.

The assay provider can provide the results of the risk assessment, and optionally, conclusions regarding one or more of diagnosis, prognosis, or appropriate therapy options to, for example, a healthcare provider, or patient, or an insurance company, in any suitable format, such as by mail or electronically, or through an online database. The information collected and provided by the assay provider can be stored in a database.

In one embodiment, a healthcare provider or insurance provider or another entity recommends, e.g., to the patient or a second healthcare provider, that a patient undergo a risk assessment for PML as described herein.

PML risk stratification tools are useful as one component in making individual benefit-risk treatment decisions for patients taking or considering taking a VLA4 inhibitor or other therapeutics known to increase risk of developing PML. Quantification of a patient's PML risk can be used, for example, in benefit-risk analysis.

Headings, e.g., (a), (b), (i) etc, are presented merely for ease of reading the specification and claims. The use of headings in the specification or claims does not require the steps or elements be performed in alphabetical or numerical order or the order in which they are presented.

The invention is further illustrated by the following examples, which should not be construed as further limiting.

EXAMPLES

Example 1. Anti-JCV Antibody Index Further Defines PML Risk in Natalizumab-Treated MS Patients In the phase 3 AFFIRM trial, natalizumab (Tysabri®, Biogen Idec) significantly reduced annualized relapse rate and the risk of sustained disability progression over 2 years compared with placebo (Polman C H, O'Connor P W, Havrdova E, et al. A randomized, placebo-controlled trial of natalizumab for relapsing multiple sclerosis. *N Engl J Med* 2006; 354(9): 899-910). The occurrence of progressive multifocal leukoencephalopathy (PML) necessitates an understanding of relative risk for informed benefit-risk evaluation and treatment decisions. The presence of anti-JC virus (JCV) antibodies is a risk factor for PML development in natalizumab-treated patients (Bloomgren G, Richman S, Hotermans C, et al. Risk of natalizumab-associated progressive multifocal leukoencephalopathy. *N Engl J Med* 2012; 366(20): 1870-80). Detection of anti-JCV antibodies has reliably predicted PML risk and affirmed the low risk of PML in anti-JCV antibody negative patients (Biogen Idec Inc. Medical Information Website. medinfo.biogenidec-.com/medinfo. Accessed Mar. 20, 2013). As of May 6, 2013, 147 PML cases had ≥1 sample tested at least 6 months prior to PML diagnosis; 145/147 (99%) tested anti-JCV antibody positive prior to PML (Biogen Idec Inc. Medical Information Website. medinfo.biogenidec.com/medinfo. Accessed Mar. 20, 2013). Results from a large prospective study, STRATIFY-2, validated the lower risk of PML in anti-JCV antibody negative patients with an estimate of 1 per 10,000 patients (Bozic C, Richman S, Plavina T, et al. Neurology 2012; 78 (Meeting Abstracts 1): S41.002). Recently, 3 European studies based on 2-9 natalizumab-treated MS patients who developed PML have reported higher anti-JCV antibody levels in patients who developed PML compared with those who did not develop PML Exteberria A, Outteryck O, Ongagna J C, et al. Presented at: 28th Congress of the European Committee for Treatment and Research in Multiple Sclerosis; Oct. 10-13, 2012; Lyon, France. P996; Trampe A K, Hemmelmann C, Stroet A, et al. *Neurology.* 2012; 78:1736-1742; Warnke C, Ramanujam R, Plavina T, et al. *J Neurol Neurosurg Psychiatry.* 2013 Mar. 5] Epub ahead of print]). We evaluated whether anti-JCV antibody levels may further define PML risks along with other known risk factors in anti-JCV antibody positive patients.

The present example describes examination of the association between anti-JCV antibody index and PML risk in anti-JCV antibody positive natalizumab-treated patients, exploration of PML risk estimates based on different anti-JCV antibody index thresholds in anti-JCV antibody positive patients, and exploration of longitudinal stability of anti-JCV antibody index-based results for patients who maintained or changed serological status over time, including pre-PML analyses performed in patients who developed PML.

Methods

Anti-JCV antibody status and anti-JCV antibody index were determined using the second-generation anti-JCV antibody assay STRATIFY JCV DxSelect™ (Focus Diagnostics, Cypress, California). Index is the sample optical density (OD) value normalized to an assay calibrator. Index is a corollary to antibody titer, which is derived by serially diluting the sample.

Anti-JCV antibody index data were collected from anti-JCV antibody positive patients enrolled in natalizumab clinical studies and from postmarketing data.

To assess the association of anti-JCV antibody index with PML risk, data from 1039 non-PML patients from 2 natalizumab clinical studies, AFFIRM and STRATIFY-1, and 45 pre-PML patients from clinical trials (excluding STRATIFY-2) and postmarketing sources as of September 2012 were evaluated (test data set) (Polman C H, O'Connor P W, Havrdova E, et al. *N Engl J Med.* 2006; 354:899-910; Bozic C, Richman S, Plavina T, et al. *Neurology.* 2012; 78 (Meeting Abstracts 1):S41.002; Bozic C, Richman S, Plavina T, et al. *Ann Neurol.* 2011; 70:742-750). Findings were validated using anti-JCV antibody index data from 1483 non-PML patients (from baseline) and 26 pre-PML patients from STRATIFY-2 (validation data set) (Bozic C, Richman S, Plavina T, et al. *Neurology.* 2012; 78 (Meeting Abstracts 1):S41.002). For both data sets, pre-PML samples were collected at least 6 months prior to PML diagnosis. The predicted probabilities of PML and non-PML patients above and below index thresholds ranging from 0.7 to 1.5 were calculated using all available longitudinal data (total samples=5547) from the combined test and validation data sets.

The probabilities were then applied to the numerators and denominators of anti-JCV antibody positive patients in the current PML risk stratification algorithm (from September 2012) to provide index-based PML risk estimates.

Longitudinal Stability of Anti-JCV Antibody Index

Using combined data from AFFIRM and STRATIFY-1 collected every 6 months over a period of 18 months, the longitudinal stability of index at various thresholds was examined for patients who maintained or changed serostatus from anti-JCV antibody negative at baseline to positive using the following categories: Ever high: ≥1 samples above index threshold; Consistently high: ≥2 consecutive samples above index threshold.

Statistical Analysis

Association of Index and PML

For patients with more than 1 available index sample, the lowest index was used. P values were calculated using a Wilcoxon rank-sum test. A cross-sectional analysis was performed to assess potential relationships between anti-JCV antibody index and current PML risk factors (prior immunosuppressant [IS] use and natalizumab treatment duration ≤24 vs ≥24 months).

Distribution of PML and Non-PML by Index Threshold and PML Risk

A repeated measures analysis was used to estimate predicted probabilities, odds ratios (ORs), and P values from generalized estimating equations with a logit link. An exchangeable correlation structure was assumed.

Results

Anti-JCV Antibody Index and PML

Figure 1B:
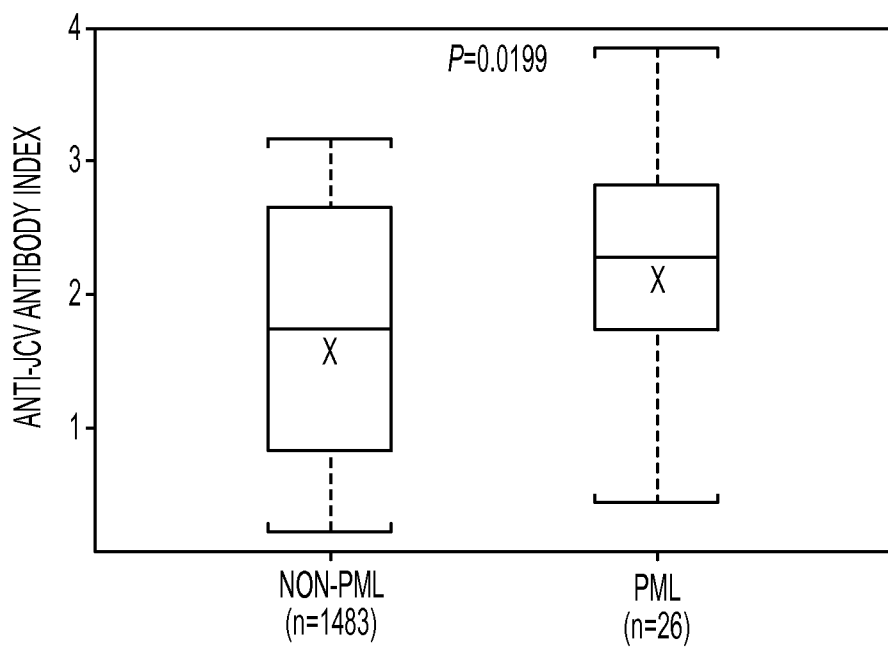

The median anti-JCV antibody index value was significantly higher in PML patients at least 6 months prior to PML diagnosis compared with non-PML patients for the test data set (P<0.0001; FIG. 1A). Results of the association between anti-JCV antibody index and PML for the validation data set confirmed the findings of the test data set (P=0.0199; FIG. 1B).

Figure 2A:
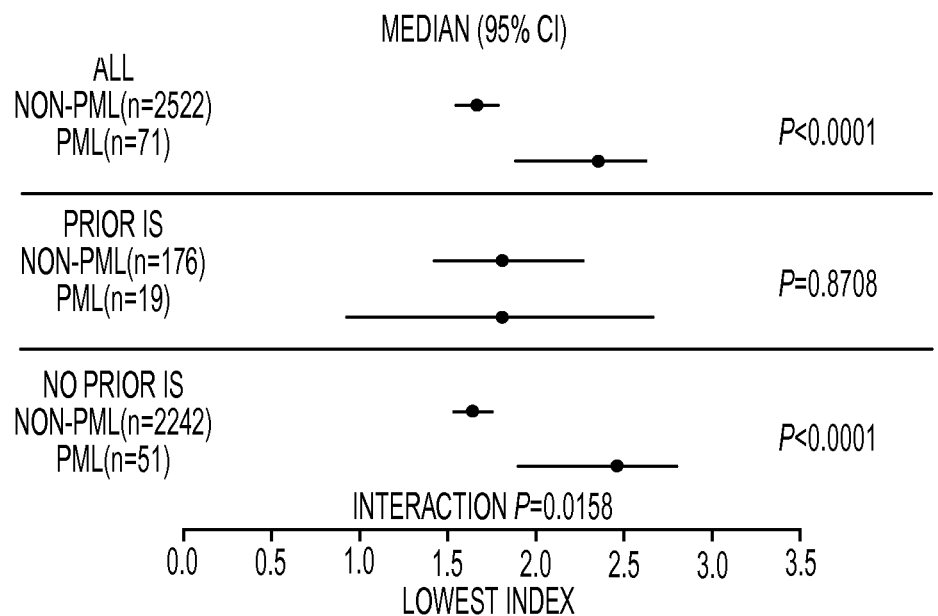
FIGS. 2A and 2B are graphs depicting the approximate incidence of PML stratified by prior immunosuppressant (IS) use and natalizumab treatment duration. (A) median anti-JCV antibody index in anti-JCV antibody positive non- PML and PML patients stratified by prior use of IS; (B) anti-JCV antibody index distribution in anti-JCV antibody positive non-PML and PML patients with no prior IS use.

No association was shown between anti-JCV antibody index and duration of natalizumab treatment (P=0.39) or prior IS use (P=0.51) in the combined population of PML and non-PML patients (data not shown). When the test and validation data sets were combined and stratified by prior IS use, a different relationship between anti-JCV antibody index and PML risk was observed (FIG. 2A). For patients with no prior IS use, the median anti-JCV antibody index was significantly higher in PML patients compared with non-PML patients (P<0.0001). In patients with prior IS use, there was no difference in anti-JCV antibody index distribution between PML and non-PML patients (P=0.87). Subsequent analyses of anti-JCV antibody index and PML risk were limited to patients with no prior IS use for the following reasons: there was a small number of PML patients with prior IS use and available anti-JCV antibody index data (n=19); underlying biology that may contribute to a difference in anti-JCV antibody index in patients with prior IS is complex and not well understood; and pooling patient populations might underestimate the risk of PML in patients with prior IS exposure.

Figure 2B:
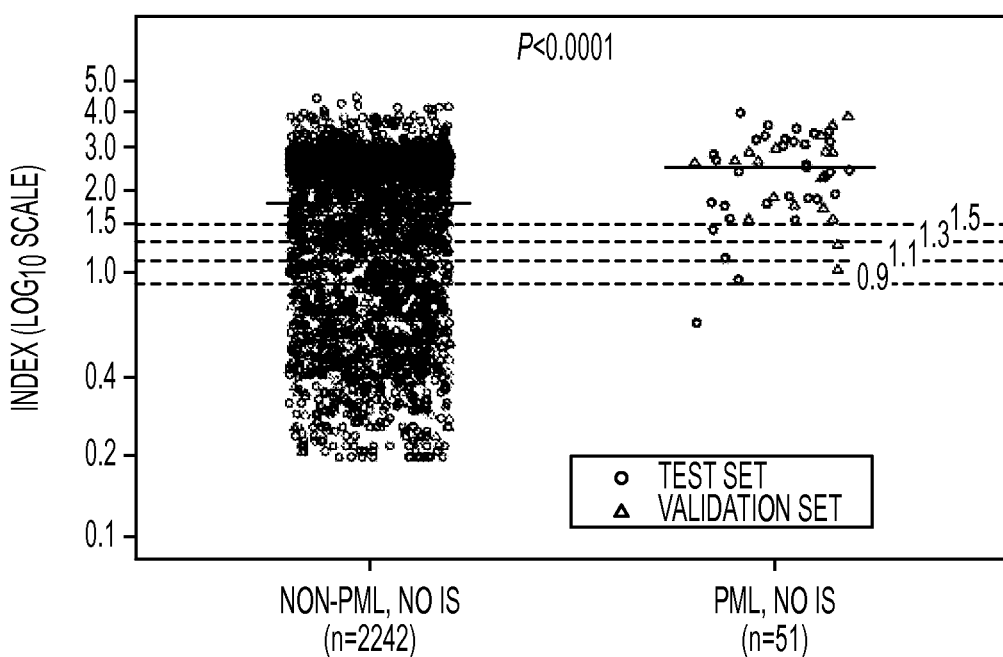

Scatter plot representation of anti-JCV antibody index data for the combined test and validation data sets of patients with no prior IS treatment highlight the significantly higher index distribution (P<0.0001) for PML patients compared with non-PML patients, with only 1 of 51 PML cases having index <0.9 and 6 of 51 PML cases having index <1.5 (FIG. 2B). Results were consistent after removing 239 patients who were not treated with natalizumab from the non-PML group; thus, natalizumab-treated patients with no prior IS who developed PML (n=51) had significantly higher anti-JCV antibody index distribution compared with non-PML patients (n=2003) (P<0.0001; data not shown).

Anti-JCV Antibody Index Threshold and PML Risk

Table 1 shows the proportions of natalizumab-treated PML (n=51) and non-PML patients (n=2242) without prior IS use from the combined test and validation data sets who fell below a range of anti-JCV antibody index thresholds.

TABLE 1

Proportions of anti-JCV antibody positive non-PML and PML patients with no prior IS use by index threshold

| Index threshold | Percentage non-PML below | 95% CI | Percentage PML below | 95% CI | OR | P value |
|---|---|---|---|---|---|---|
| ≤0.7 | 21.1 | 19.5-22.7 | 0.6 | 0.1-3.9 | 45.6 | <0.001 |
| ≤0.9 | 28.2 | 26.5-30.1 | 1.7 | 0.2-10.9 | 22.9 | 0.002 |
| ≤1.1 | 33.6 | 31.8-35.6 | 4.4 | 1.4-12.9 | 11.1 | <0.001 |
| ≤1.3 | 37.9 | 36.0-39.9 | 7.5 | 3.0-17.6 | 7.5 | <0.001 |
| ≤1.5 | 42.9 | 41.0-44.9 | 10.1 | 4.5-21.2 | 6.7 | <0.001 |

Data for patients with no prior IS use: 2242 non-PML patients and 51 patients using all available anti-JCV antibody index data at least 6 months prior to PML diagnosis. A total of 5547 samples were analyzed by repeated measures with predicted probabilities, ORs, and P values estimated from generalized estimating equations with a logit link. An exchangeable correlation structure was assumed.
CI = confidence interval.

Using the combined test and validation data sets, PML risk estimates for anti-JCV antibody positive patients with no prior IS use were generated for each index threshold over the range of 0.9 to 1.5 (Table 2). For anti-JCV antibody positive patients with no prior IS use and an anti-JCV antibody index below the threshold and in the range between 0.9 and 1.5, the risk of PML was lower compared with the total population of anti-JCV antibody positive patients with no prior IS use, as per the current algorithm (Bloomgren G, Richman S, Hotermans C, et al. N Engl J Med. 2012; 366:1870-1880; Biogen Idec Inc. Medical Information Website. medinfo.biogenidec.com/medinfo. Accessed Mar. 20, 2013). For patients with an anti-JCV antibody index >1.5, the risk of PML was higher compared with the total population of anti-JCV antibody positive patients with no prior IS use, as per the current algorithm (Bloomgren G, Richman S, Hotermans C, et al. N Engl J Med. 2012; 366:1870-1880; Biogen Idec Inc. Medical Information Website. medinfo.biogenidec.com/medinfo. Accessed Mar. 20, 2013).

TABLE 2

PML risk estimates by index threshold in anti-JCV antibody positive patients with no prior IS use

| | PML risk estimates per 1000 patients (no prior IS use) | | |
|---|---|---|---|
| Index result | 1-24 months (95% CI) | 25-48 months (95% CI) | 49-72 months (95% CI) |
| ≤0.9 | 0.1 (0-0.41) | 0.3 (0.04-1.13) | 0.4 (0.01-2.15) |
| ≤1.1 | 0.1 (0-0.34) | 0.7 (0.21-1.53) | 0.7 (0.08-2.34) |
| ≤1.3 | 0.1 (0.01-0.39) | 1.0 (0.48-1.98) | 1.2 (0.31-2.94) |
| ≤1.5 | 0.1 (0.03-0.42) | 1.2 (0.64-2.15) | 1.3 (0.41-2.96) |
| >1.5 | 1.0 (0.64-1.41) | 8.1 (6.64-9.8) | 8.5 (6.22-11.38) |

PML risk estimates for anti-JCV antibody index thresholds were calculated based on the current PML risk stratification algorithm (from September 2012) and predicted probabilities shown in Table 1 for the population at or below that particular index (0.9-1.5) and for the population above an index of 1.5. For index thresholds below 0.9, patient numbers were insufficient to allow for calculation of risk estimates.

Longitudinal Stability of Anti-JCV Antibody Index

Longitudinal data were available every 6 months over a period of 18 months for 553 anti-JCV antibody negative patients at baseline who had no prior IS use. Over a period of 18 months, 87% of patients who tested anti-JCV antibody negative at baseline remained anti-JCV antibody negative at subsequent testing (Table 3). Over a period of 18 months, 96% of patients who tested anti-JCV antibody negative at baseline remained below the anti-JCV antibody index threshold of 0.9. Over a period of 18 months, 69% (51 of 74) patients who changed serostatus from negative at baseline to having ≥1 positive sample remained consistently below the anti-JCV antibody index threshold of 0.9. Approximately 4% of patients who tested anti-JCV antibody negative at baseline had ≥1 sample above the anti-JCV antibody index threshold of 0.9 over a period of 18 months. Approximately 2% of patients who tested anti-JCV antibody negative at baseline had ≥2 consecutive samples above the anti-JCV antibody index threshold of 0.9 over a period of 18 months.

TABLE 3

Anti-JCV antibody index over a period of 18 months for patients who were anti-JCV antibody negative at baseline (n = 553)

| | Index threshold | | |
|---|---|---|---|
| | 0.9 | 1.2 | 1.5 |
| Percentage at consistently lower risk | 95.8% | 96.0% | 96.6% |
| Consistently negative | 86.6% | 86.6% | 86.6% |
| ≥1 positive sample but low anti-JCV antibody index (consistently below threshold) | 9.2% | 9.4% | 9.9% |
| Percentage at higher risk | | | |
| Ever high (≥1 sample above index threshold) | 4.2% | 4.0% | 3.4% |
| Consistently high (≥2 consecutive samples above index threshold) | 2.2% | 2.0% | 1.6% |

Includes longitudinal samples collected every 6 months from 553 anti-JCV antibody negative patients at baseline who had no prior IS use and were followed over a period of 18 months in AFFIRM and STRATIFY-I.

Figure 3:
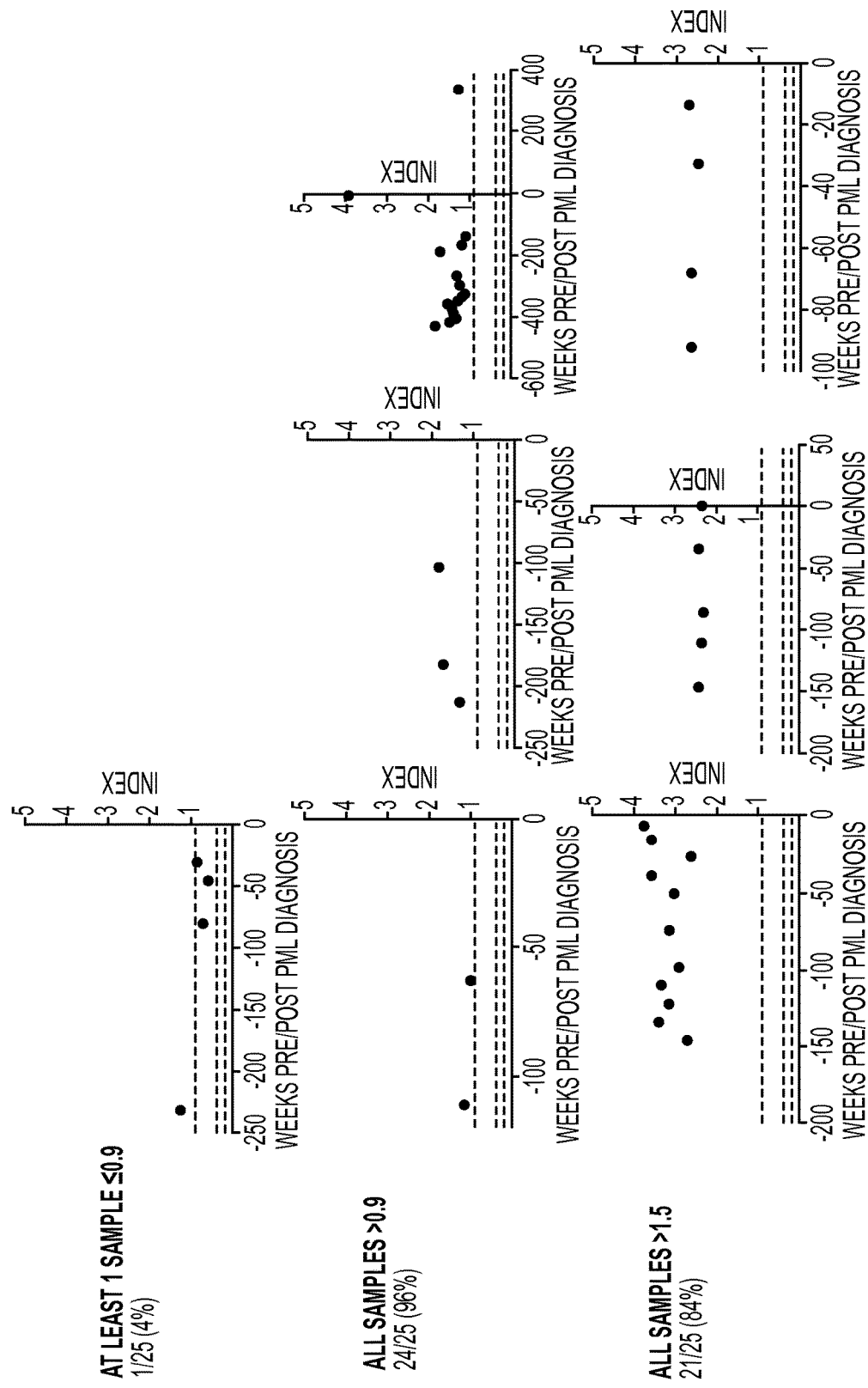
FIG. 3 is a schematic diagram depicting the approximate incidence of PML stratified by anti-JCV antibody sero status, prior immunosuppressant use, and natalizumab treatment duration. Data from 25 PML cases in patients with no IS use and ≥2 pre-PML samples available at least 6 months prior to PML diagnosis.

Twenty-five natalizumab-treated MS patients who developed PML had no prior IS use and ≥2 pre-PML samples at least 6 months prior to PML diagnosis. One patient (4%) had 3 samples with an anti-JCV antibody index <0.9, 2 of which were collected within 12 months of PML diagnosis (FIG. 3). For the remaining 24 patients (96%), all samples had an anti-JCV antibody index >0.9, and for 21 of 25 (84%) patients, all samples had an anti-JCV antibody index >1.5.

Therefore, anti-JCV antibody index may further differentiate PML risk for anti-JCV antibody positive MS patients. In natalizumab-treated patients with no prior IS use, a higher anti-JCV antibody index correlates with an increased PML risk. Furthermore, most patients who are anti-JCV antibody negative at baseline remain consistently negative or change to lower index anti-JCV antibody positive status. For example, in the combined AFFIRM and STRATIFY-1 cohorts, of those patients who tested anti-JCV antibody negative at baseline, 87% remained consistently negative and 96% remained consistently at lower risk (anti-JCV antibody index ≤0.9) over a period of 18 months. These analyses may potentially better inform PML risk in patients who seroconvert or test intermittently positive. Longitudinal pre-PML samples demonstrate consistently positive anti-JCV antibody status and a high anti-JCV antibody index over time. Ninety-six percent (24/25) of natalizumab-treated MS patients who developed PML and had 2 or more samples available had all pre-PML samples with an index above 0.9.

Other embodiments are in the claims.

What is claimed is:

1. A method of treating a subject in need thereof with an anti-VLA-4 therapy, the method comprising:
   a) determining an anti-JC virus (JCV) antibody titer in two or more biological samples obtained from the subject over a period of time, wherein the titer is determined to be at or above a pre-determined level in a first biological sample of the two or more biological samples and below the pre-determined level in a second subsequent biological sample of the two or more biological samples; and
   b) administering the anti-VLA-4 therapy to the subject, thereby treating the subject with the anti-VLA-4 therapy, wherein the subject suffers from multiple sclerosis, a relapsing form of multiple sclerosis or inflammatory bowel disease.

2. The method of claim 1, wherein the pre-determined level is 0.9.

3. The method of claim 1, wherein the pre-determined level is 1.5.

4. The method of claim 1, wherein the period of time is 6 months.

5. The method of claim 1, wherein the period of time is 12 months.

6. The method of claim 1, wherein the period of time is 18 months.

7. The method of claim 1, wherein the two or more samples are consecutive samples.

8. The method of claim 1, wherein the patient has received the anti-VLA-4 therapy during the period of time.

9. The method of claim 1, wherein the anti-VLA-4 therapy is comprises an anti-VLA-4 antibody or fragment thereof.

10. The method of claim 9, wherein the anti-VLA-4 antibody or fragment thereof is natalizumab or an antigen-binding fragment thereof.

11. The method of claim 9, wherein the anti-VLA-4 antibody or fragment thereof is natalizumab.

12. The method of claim 1, wherein the subject has a negative prior immunosuppressant exposure classification.

13. The method of claim 1, wherein the subject the subject has been free of a non-anti-VLA-4 immunosuppressant therapy for a period within 1, 3, or 5 years.

14. The method of claim 1, wherein the subject has been free of a non-anti-VLA-4 immunosuppressant therapy for the lifetime of the subject.

15. The method of claim 1, wherein the subject suffers from multiple sclerosis.

16. The method of claim 1, wherein the subject suffers from relapsing remitting multiple sclerosis.

17. The method of claim 1, wherein the subject suffers from inflammatory bowel disease.

18. The method of claim 17, wherein the inflammatory bowel disease is Crohn's disease.

19. The method of claim 17, wherein the inflammatory bowel disease is ulcerative colitis.

20. The method of claim 1, wherein the method further comprises determining the subject has one or more factors that indicate the subject is at an increased risk of progressive multifocal leukoencephalopathy (PML) and the method further comprises performing enhanced monitoring of the subject as compared to a subject determined not to have an increased risk of PML.

21. The method of claim 1, wherein the anti-JCV antibody titer is determined to be above 0 in the two or more samples and the method comprises performing enhanced monitoring of the subject as compared to a subject determined to have a negative anti-JCV antibody status.

22. The method of claim 21, wherein the subject has received prior treatment with an anti-VLA-4 therapy for 24 months or less, has not received prior therapy with an immunosuppressant, is determined to have an anti-JCV antibody titer of greater than 0, and the method further comprises performing enhanced monitoring of the subject as compared to a subject determined to have a negative anti-JCV antibody status.

23. The method of claim 20, wherein the subject has received an anti-VLA-4 therapy for longer than 24 months and the method comprises performing enhanced monitoring of the subject determined to have received anti-VLA-4 therapy for less than 24 months.

24. The method of claim 20, wherein the subject has a positive prior immunosuppressant exposure classification and the method comprises performing enhanced monitoring of the subject as compared to a subject that has a negative prior immunosuppressant exposure classification.

25. The method of claim 20, wherein the enhanced monitoring comprises performing MRI scans to identify brain lesions due to PML.

26. The method of claim 20, wherein the enhanced monitoring comprises performing increased frequency of tests to identify the presence of JCV in the subject.

* * * * *